US012715914B2

(12) United States Patent
Kwan et al.

(10) Patent No.: US 12,715,914 B2
(45) Date of Patent: Aug. 25, 2026

(54) IL-17 BINDING PROTEINS, COMPOSITIONS, AND METHODS OF USE THEREOF

(71) Applicant: Paragon Therapeutics, Inc., Waltham, MA (US)

(72) Inventors: Byron Hua Kwan, Bothell, WA (US); Daniel Rios, Boston, MA (US); Jacob Cole Milligan, Vista, CA (US); Jason Zee Seug Oh, Shrewsbury, MA (US); Hussam Hisham Shaheen, Dorado, PR (US); Roberto Di Niro, Santa Fe, NM (US); Fortunato Ferrara, Santa Fe, NM (US); Michael Frank Erasmus, Santa Fe, NM (US); Luis Antonio Rodriguez-Carnero, Santa Fe, NM (US)

(73) Assignee: Paragon Therapeutics, Inc., Waltham, MA (US)

( * ) Notice: Subject to any disclaimer, the term of this patent is extended or adjusted under 35 U.S.C. 154(b) by 0 days.

(21) Appl. No.: 19/555,125

(22) Filed: Mar. 3, 2026

(65) Prior Publication Data

US 2026/0176349 A1 Jun. 25, 2026

Related U.S. Application Data

(63) Continuation of application No. 19/324,344, filed on Sep. 10, 2025.

(60) Provisional application No. 63/767,149, filed on Mar. 5, 2025, provisional application No. 63/693,684, filed on Sep. 11, 2024.

(51) Int. Cl.
*C07K 16/24* (2006.01)
*A61K 39/00* (2006.01)

(52) U.S. Cl.
CPC ...... *C07K 16/244* (2013.01); *A61K 2039/505* (2013.01); *C07K 2317/24* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS 7,838,638 B2 11/2010 Allan et al.
7,931,900 B2 4/2011 Christie et al.
8,003,099 B2 8/2011 Auer et al.
8,012,476 B2 9/2011 Dall'Acqua et al.
8,057,794 B2 11/2011 Rapecki et al.
8,137,671 B2 3/2012 Masternak et al.
8,231,875 B2 7/2012 Adams et al.
8,303,953 B2 11/2012 Adams et al.
8,329,431 B2 12/2012 Adams et al.
8,435,761 B2 5/2013 Rapecki et al.
8,580,265 B2 11/2013 Adams et al.
8,617,847 B2 12/2013 Adams et al.
8,679,494 B2 3/2014 Ceska et al.
8,715,669 B2 5/2014 Masternak et al.
8,790,642 B2 7/2014 Chen et al.
8,865,167 B2 10/2014 Adams et al.
9,034,600 B2 5/2015 Adams et al.
9,045,537 B2 6/2015 Ceska et al.
9,376,491 B2 6/2016 Corvari et al.
9,714,292 B2 7/2017 Auer et al.
9,771,420 B2 9/2017 Ceska et al.
9,890,219 B2 2/2018 Adams et al.
9,920,120 B2 3/2018 Yu et al.
9,988,446 B2 6/2018 Adams et al.
10,017,568 B2 7/2018 Rommelaere et al.
10,112,994 B2 10/2018 Giulianotti et al.
10,208,349 B2 2/2019 Platt et al.
10,308,723 B2 6/2019 Adams et al.
10,329,346 B2 6/2019 Auer et al.
10,358,460 B2 7/2019 Bassett et al.
10,487,136 B2 11/2019 Bilgischer et al.
10,526,384 B2 1/2020 Hinner et al.
10,676,522 B2 6/2020 Grant et al.
11,236,391 B2 2/2022 Townsend et al.
11,384,136 B2 7/2022 Bilgischer et al.
11,466,324 B2 10/2022 Platt et al.
11,492,396 B2 11/2022 Glatt et al.
11,634,485 B2 4/2023 Corvari et al.
11,667,704 B2 6/2023 Hu et al.
11,857,625 B2 1/2024 Durran et al.
11,919,950 B2 3/2024 Adams et al.
11,999,772 B2 6/2024 Adams et al.
12,275,777 B2 4/2025 Bilgischer et al.
12,319,742 B1 6/2025 De Silva et al.
2010/0266595 A1 10/2010 Kolumam et al.
2010/0266609 A1 10/2010 Adams et al.
2014/0044732 A1 2/2014 Adams et al.

(Continued)

FOREIGN PATENT DOCUMENTS

WO 2009/136286 A2 11/2009
WO 2012/095662 A1 7/2012

(Continued)

OTHER PUBLICATIONS

International Search Report and Written Opinion, PCT/US2025/045659, dated Mar. 19, 2026, 22 pages.
Dall'Acqua, W. et al., "Properties of Human IgG1s Engineered for Enhanced Binding to the Neonatal Fc Receptor (FcRn)," The Journal of Biological Chemistry, vol. 281 ( 33): 23514-23524 (2006).
International Search Report and Written Opinion, PCT/US2024/035060, dated Jan. 13, 2025, 14 pages.

(Continued)

*Primary Examiner* — Gary B Nickol
(74) *Attorney, Agent, or Firm* — Nelson Mullins Riley & Scarborough LLP; Jane E. Remillard, Esq.; Jill Gorny Sloper, Esq.

(57) ABSTRACT

IL-17-binding proteins, related compositions, and related methods of use.

21 Claims, 12 Drawing Sheets

Specification includes a Sequence Listing.

(56) References Cited

U.S. PATENT DOCUMENTS

| | | | |
|---|---|---|---|
| 2014/0186355 | A1 | 7/2014 | Adams et al. |
| 2015/0147331 | A1 | 5/2015 | Adams et al. |
| 2016/0251429 | A1 | 9/2016 | Adams et al. |
| 2017/0081400 | A1 | 3/2017 | Poulton et al. |
| 2017/0275355 | A1 | 9/2017 | Adams et al. |
| 2017/0334985 | A1 | 11/2017 | Wu et al. |
| 2018/0037646 | A1 | 2/2018 | Ceska et al. |
| 2018/0201673 | A1 | 7/2018 | Linnik |
| 2018/0312584 | A1 | 11/2018 | Deperalta et al. |
| 2018/0327446 | A1 | 11/2018 | Fong et al. |
| 2018/0346561 | A1 | 12/2018 | Adams et al. |
| 2018/0356429 | A1 | 12/2018 | Morimoto et al. |
| 2020/0140537 | A1 | 5/2020 | Blakely et al. |
| 2020/0277366 | A1 | 9/2020 | Adams et al. |
| 2020/0405855 | A1 | 12/2020 | Grogan et al. |
| 2021/0106683 | A1 | 4/2021 | Durran et al. |
| 2021/0324111 | A1 | 10/2021 | Bhatta et al. |
| 2022/0073581 | A1 | 3/2022 | Adams et al. |
| 2023/0087378 | A1 | 3/2023 | Khan et al. |
| 2023/0279093 | A1 | 9/2023 | Glatt et al. |
| 2023/0287100 | A1 | 9/2023 | Glatt et al. |
| 2024/0123065 | A1 | 4/2024 | Durran et al. |
| 2024/0352083 | A1 | 10/2024 | Adams et al. |
| 2024/0376191 | A1 | 11/2024 | Adams et al. |
| 2025/0042988 | A1 | 2/2025 | Reich |
| 2025/0197475 | A1 | 6/2025 | Smith et al. |
| 2025/0304683 | A1 | 10/2025 | Vemuri et al. |
| 2025/0304684 | A1 | 10/2025 | Vemuri et al. |
| 2026/0070969 | A1 | 3/2026 | Kwan et al. |

FOREIGN PATENT DOCUMENTS

| | | | |
|---|---|---|---|
| WO | 2014161570 | A1 | 10/2014 |
| WO | 2016160976 | A2 | 10/2016 |
| WO | 2017/072183 | A1 | 5/2017 |
| WO | 2019027828 | A1 | 2/2019 |
| WO | 2020/157305 | A1 | 8/2020 |
| WO | 2021060425 | A1 | 4/2021 |
| WO | 2023/203549 | A1 | 10/2023 |
| WO | 2024/141567 | A1 | 7/2024 |
| WO | 2024/218708 | A2 | 10/2024 |
| WO | 2024263945 | A2 | 12/2024 |
| WO | 2025/137159 | A1 | 6/2025 |
| WO | 2025/144089 | A1 | 7/2025 |
| WO | 2025/238133 | A1 | 11/2025 |

OTHER PUBLICATIONS

Kwan, B. et al. "Characterization of ORKA-002, a Novel Extended Half-life Monoclonal Antibody Targeting IL-17A/F for the Treatment of Psoriasis and Other Indications," American Academy of Dermatology (AAD) meeting, Poster Presentation, Mar. 7-11, 2025, 1 page.

Kwan, B. et al. "Characterization of ORKA-002, a Novel Extended Half-life Monoclonal Antibody Targeting IL-17A/F for the Treatment of Psoriasis and Other Indications," Society for Investigative Dermatology (SID) meeting, Poster Presenation, May 7-10, 2025, 1 page.

Ma, H. et al., "Generation and characterization of QLS22001, a humanized monoclonal antibody that neutralizes IL-17A and IL-17F with an extended half-life" International Immmunopharmacology, vol. 117:1-8 (2023).

Oruka Corporate Deck, Apr. 3, 2024, 31 pages.

Oruka Corporate Deck, May 2024, 30 pages.

Oruka Corporate Deck, Aug. 9, 2024, 31 pages.

Oruka Corporate Deck, Sep. 24, 2024, 31 pages.

Oruka Corporate Deck, Sep. 25, 2024, 31 pages.

Oruka Corporate Deck, Jan. 9, 2025, 35 pages.

Oruka Corporate Deck, Mar. 6, 2025, 33 pages.

Oruka Corporate Deck, May 20, 2025, 34 pages.

Oruka Corporate Deck, Jul. 20, 2025, 35 pages.

Robbie, G. et al., "A Novel Investigational Fc-Modified Humanized Monoclonal Antibody, Motavizumab-YTE, Has an Extended Half-Life in Healthy Adults," Antimicrobial Agents and Chemotherapy, vol. 57(12): 6147-6153 (2013).

Rocca, A. et al., "Passive Immunoprophylaxis against Respiratory Syncytial Virus in Children: Where Are We Now?," Int. J. Mol. Sci.., vol. 22 (3703) 22 pages (2021).

Saunders, K., "Conceptual Approaches to Modulating Antibody Effector Functions and Circulation Half-Life," Frontiers in Immunology, vol. 10 (Article 1296): 20 pages (2019).

SEQUENCE LISTING

```
Sequence total quantity: 311
SEQ ID NO: 1             moltype = AA  length = 5
FEATURE                  Location/Qualifiers
source                   1..5
                         mol_type = protein
                         organism = synthetic construct
SEQUENCE: 1
DYSMA                                                              5

SEQ ID NO: 2             moltype = AA  length = 16
FEATURE                  Location/Qualifiers
source                   1..16
                         mol_type = protein
                         organism = synthetic construct
SEQUENCE: 2
TIGPSGDTYY RDSVKG                                                  16

SEQ ID NO: 3             moltype = AA  length = 16
FEATURE                  Location/Qualifiers
source                   1..16
                         mol_type = protein
                         organism = synthetic construct
SEQUENCE: 3
PPQYYEGSIP RLWPAH                                                  16

SEQ ID NO: 4             moltype = AA  length = 11
FEATURE                  Location/Qualifiers
source                   1..11
                         mol_type = protein
                         organism = synthetic construct
SEQUENCE: 4
RADESVRTLM H                                                       11

SEQ ID NO: 5             moltype = AA  length = 7
FEATURE                  Location/Qualifiers
source                   1..7
                         mol_type = protein
                         organism = synthetic construct
SEQUENCE: 5
LVSNSEI                                                            7

SEQ ID NO: 6             moltype = AA  length = 9
FEATURE                  Location/Qualifiers
source                   1..9
                         mol_type = protein
```

```
                       organism = synthetic construct
SEQUENCE: 6
LQTHSYPYT                                                                  9

SEQ ID NO: 7           moltype = AA  length = 8
FEATURE                Location/Qualifiers
source                 1..8
                       mol_type = protein
                       organism = synthetic construct
SEQUENCE: 7
GFPFSDYS                                                                   8

SEQ ID NO: 8           moltype = AA  length = 7
FEATURE                Location/Qualifiers
source                 1..7
                       mol_type = protein
                       organism = synthetic construct
SEQUENCE: 8
IGPSGDT                                                                    7

SEQ ID NO: 9           moltype = AA  length = 18
FEATURE                Location/Qualifiers
source                 1..18
                       mol_type = protein
                       organism = synthetic construct
SEQUENCE: 9
ASPPQYYEGS IPRLWPAH                                                        18

SEQ ID NO: 10          moltype = AA  length = 6
FEATURE                Location/Qualifiers
source                 1..6
                       mol_type = protein
                       organism = synthetic construct
SEQUENCE: 10
ESVRTL                                                                     6

SEQ ID NO: 11          moltype = AA  length = 7
FEATURE                Location/Qualifiers
source                 1..7
                       mol_type = protein
                       organism = synthetic construct
SEQUENCE: 11
GFPFSDY                                                                    7

SEQ ID NO: 12          moltype = AA  length = 5
FEATURE                Location/Qualifiers
source                 1..5
                       mol_type = protein
                       organism = synthetic construct
SEQUENCE: 12
GPSGD                                                                      5

SEQ ID NO: 13          moltype = AA  length = 14
FEATURE                Location/Qualifiers
source                 1..14
                       mol_type = protein
                       organism = synthetic construct
SEQUENCE: 13
PQYYEGSIPR LWPA                                                            14

SEQ ID NO: 14          moltype = AA  length = 7
FEATURE                Location/Qualifiers
source                 1..7
                       mol_type = protein
                       organism = synthetic construct
SEQUENCE: 14
DESVRTL                                                                    7

SEQ ID NO: 15          moltype = AA  length = 6
FEATURE                Location/Qualifiers
source                 1..6
                       mol_type = protein
                       organism = synthetic construct
SEQUENCE: 15
THSYPY                                                                     6

SEQ ID NO: 16          moltype = AA  length = 124
FEATURE                Location/Qualifiers
source                 1..124
```

```
                         mol_type = protein
                         organism = synthetic construct
SEQUENCE: 16
EVQLVESGGG LVQPGGSLRL SCAASGFPFS DYSMAWVRQA PGKGLEWVAT IGPSGDTYYR  60
DSVKGRFTIS RDNAKNSLYL QMNSLRAEDT AVYYCASPPQ YYEGSIPRLW PAHWGQGTLV  120
TVSS                                                               124

SEQ ID NO: 17            moltype = AA  length = 107
FEATURE                  Location/Qualifiers
source                   1..107
                         mol_type = protein
                         organism = synthetic construct
SEQUENCE: 17
AIQLTQSPSS LSASVGDRVT ITCRADESVR TLMHWYQQKP GKAPKLLIYL VSNSEIGVPD  60
RFSGSGSGTD FRLTISSLQP EDFATYYCLQ THSYPYTFGQ GTKVEIK                107

SEQ ID NO: 18            moltype = AA  length = 107
FEATURE                  Location/Qualifiers
source                   1..107
                         mol_type = protein
                         organism = synthetic construct
SEQUENCE: 18
DIQLTQSPSS LSASVGDRVT ITCRADESVR TLMHWYQQKP GKAPKLLIYL VSNSEIGVPD  60
RFSGSGSGTD FRLTISSLQP EDFATYYCLQ THSYPYTFGQ GTKVEIK                107

SEQ ID NO: 19            moltype = AA  length = 16
FEATURE                  Location/Qualifiers
source                   1..16
                         mol_type = protein
                         organism = synthetic construct
SEQUENCE: 19
TITGSGSTYY RDSVKG                                                  16

SEQ ID NO: 20            moltype = AA  length = 16
FEATURE                  Location/Qualifiers
source                   1..16
                         mol_type = protein
                         organism = synthetic construct
SEQUENCE: 20
PPQYYEGSIV RLWPAH                                                  16

SEQ ID NO: 21            moltype = AA  length = 9
FEATURE                  Location/Qualifiers
source                   1..9
                         mol_type = protein
                         organism = synthetic construct
SEQUENCE: 21
AQSYSMPWT                                                          9

SEQ ID NO: 22            moltype = AA  length = 7
FEATURE                  Location/Qualifiers
source                   1..7
                         mol_type = protein
                         organism = synthetic construct
SEQUENCE: 22
ITGSGST                                                            7

SEQ ID NO: 23            moltype = AA  length = 18
FEATURE                  Location/Qualifiers
source                   1..18
                         mol_type = protein
                         organism = synthetic construct
SEQUENCE: 23
ASPPQYYEGS IVRLWPAH                                                18

SEQ ID NO: 24            moltype = AA  length = 5
FEATURE                  Location/Qualifiers
source                   1..5
                         mol_type = protein
                         organism = synthetic construct
SEQUENCE: 24
TGSGS                                                              5

SEQ ID NO: 25            moltype = AA  length = 14
FEATURE                  Location/Qualifiers
source                   1..14
                         mol_type = protein
                         organism = synthetic construct
SEQUENCE: 25
```

```
PQYYEGSIVR LWPA                                                   14

SEQ ID NO: 26           moltype = AA  length = 6
FEATURE                 Location/Qualifiers
source                  1..6
                        mol_type = protein
                        organism = synthetic construct
SEQUENCE: 26
SYSMPW                                                            6

SEQ ID NO: 27           moltype = AA  length = 124
FEATURE                 Location/Qualifiers
source                  1..124
                        mol_type = protein
                        organism = synthetic construct
SEQUENCE: 27
EVQLVESGGG LVQPGGSLRL SCAASGFPFS DYSMAWVRQA PGKGLEWVAT ITGSGSTYYR  60
DSVKGRFTIS RDNAKNSLYL QMNSLRAEDT AVYYCASPPQ YYEGSIVRLW PAHWGQGTLV  120
TVSS                                                              124

SEQ ID NO: 28           moltype = AA  length = 107
FEATURE                 Location/Qualifiers
source                  1..107
                        mol_type = protein
                        organism = synthetic construct
SEQUENCE: 28
DIQLTQSPSS LSASVGDRVT ITCRADESVR TLMHWYQQKP GKAPKLLIYL VSNSEIGVPD  60
RFSGSGSGTD FRLTISSLQP EDFATYYCAQ SYSMPWTFGQ GTKVEIK               107

SEQ ID NO: 29           moltype = AA  length = 5
FEATURE                 Location/Qualifiers
source                  1..5
                        mol_type = protein
                        organism = synthetic construct
SEQUENCE: 29
DYYMA                                                             5

SEQ ID NO: 30           moltype = AA  length = 17
FEATURE                 Location/Qualifiers
source                  1..17
                        mol_type = protein
                        organism = synthetic construct
SEQUENCE: 30
TISGSGGTTY YRDSVKG                                                17

SEQ ID NO: 31           moltype = AA  length = 16
FEATURE                 Location/Qualifiers
source                  1..16
                        mol_type = protein
                        organism = synthetic construct
SEQUENCE: 31
PPQYYEGSIP RLWFAH                                                 16

SEQ ID NO: 32           moltype = AA  length = 8
FEATURE                 Location/Qualifiers
source                  1..8
                        mol_type = protein
                        organism = synthetic construct
SEQUENCE: 32
GFRFSDYY                                                          8

SEQ ID NO: 33           moltype = AA  length = 8
FEATURE                 Location/Qualifiers
source                  1..8
                        mol_type = protein
                        organism = synthetic construct
SEQUENCE: 33
ISGSGGTT                                                          8

SEQ ID NO: 34           moltype = AA  length = 18
FEATURE                 Location/Qualifiers
source                  1..18
                        mol_type = protein
                        organism = synthetic construct
SEQUENCE: 34
ASPPQYYEGS IPRLWFAH                                               18

SEQ ID NO: 35           moltype = AA  length = 7
FEATURE                 Location/Qualifiers
```

```
source                  1..7
                        mol_type = protein
                        organism = synthetic construct
SEQUENCE: 35
GFRFSDY                                                                7

SEQ ID NO: 36           moltype = AA  length = 6
FEATURE                 Location/Qualifiers
source                  1..6
                        mol_type = protein
                        organism = synthetic construct
SEQUENCE: 36
SGSGGT                                                                 6

SEQ ID NO: 37           moltype = AA  length = 14
FEATURE                 Location/Qualifiers
source                  1..14
                        mol_type = protein
                        organism = synthetic construct
SEQUENCE: 37
PQYYEGSIPR LWFA                                                        14

SEQ ID NO: 38           moltype = AA  length = 125
FEATURE                 Location/Qualifiers
source                  1..125
                        mol_type = protein
                        organism = synthetic construct
SEQUENCE: 38
EVQLVESGGG LVQPGGSLRL SCAASGFRFS DYYMAWVRQA PGKGLEWVAT ISGSGGTTYY  60
RDSVKGRFTI SRDNAKNSLY LQMNSLRAED TAVYYCASPP QYYEGSIPRL WFAHWGQGTL  120
VTVSS                                                                  125

SEQ ID NO: 39           moltype = AA  length = 5
FEATURE                 Location/Qualifiers
source                  1..5
                        mol_type = protein
                        organism = synthetic construct
SEQUENCE: 39
SYGMA                                                                  5

SEQ ID NO: 40           moltype = AA  length = 16
FEATURE                 Location/Qualifiers
source                  1..16
                        mol_type = protein
                        organism = synthetic construct
SEQUENCE: 40
TIDAAGDTYY RDSVKG                                                      16

SEQ ID NO: 41           moltype = AA  length = 16
FEATURE                 Location/Qualifiers
source                  1..16
                        mol_type = protein
                        organism = synthetic construct
SEQUENCE: 41
PPQTYEGSIY RLWFAH                                                      16

SEQ ID NO: 42           moltype = AA  length = 11
FEATURE                 Location/Qualifiers
source                  1..11
                        mol_type = protein
                        organism = synthetic construct
SEQUENCE: 42
RADESVKTLM H                                                           11

SEQ ID NO: 43           moltype = AA  length = 9
FEATURE                 Location/Qualifiers
source                  1..9
                        mol_type = protein
                        organism = synthetic construct
SEQUENCE: 43
QQTYSAPHT                                                              9

SEQ ID NO: 44           moltype = AA  length = 8
FEATURE                 Location/Qualifiers
source                  1..8
                        mol_type = protein
                        organism = synthetic construct
SEQUENCE: 44
GFTFPSYG                                                               8
```

```
SEQ ID NO: 45          moltype = AA  length = 7
FEATURE                Location/Qualifiers
source                 1..7
                       mol_type = protein
                       organism = synthetic construct
SEQUENCE: 45
IDAAGDT                                                              7

SEQ ID NO: 46          moltype = AA  length = 18
FEATURE                Location/Qualifiers
source                 1..18
                       mol_type = protein
                       organism = synthetic construct
SEQUENCE: 46
AAPPQTYEGS IYRLWFAH                                                  18

SEQ ID NO: 47          moltype = AA  length = 6
FEATURE                Location/Qualifiers
source                 1..6
                       mol_type = protein
                       organism = synthetic construct
SEQUENCE: 47
ESVKTL                                                               6

SEQ ID NO: 48          moltype = AA  length = 7
FEATURE                Location/Qualifiers
source                 1..7
                       mol_type = protein
                       organism = synthetic construct
SEQUENCE: 48
GFTFPSY                                                              7

SEQ ID NO: 49          moltype = AA  length = 5
FEATURE                Location/Qualifiers
source                 1..5
                       mol_type = protein
                       organism = synthetic construct
SEQUENCE: 49
DAAGD                                                                5

SEQ ID NO: 50          moltype = AA  length = 14
FEATURE                Location/Qualifiers
source                 1..14
                       mol_type = protein
                       organism = synthetic construct
SEQUENCE: 50
PQTYEGSIYR LWFA                                                      14

SEQ ID NO: 51          moltype = AA  length = 7
FEATURE                Location/Qualifiers
source                 1..7
                       mol_type = protein
                       organism = synthetic construct
SEQUENCE: 51
DESVKTL                                                              7

SEQ ID NO: 52          moltype = AA  length = 6
FEATURE                Location/Qualifiers
source                 1..6
                       mol_type = protein
                       organism = synthetic construct
SEQUENCE: 52
TYSAPH                                                               6

SEQ ID NO: 53          moltype = AA  length = 124
FEATURE                Location/Qualifiers
source                 1..124
                       mol_type = protein
                       organism = synthetic construct
SEQUENCE: 53
EVQLVESGGG LVQPGGSLRL SCAASGFTFP SYGMAWVRQA PGKGLEWVAT IDAAGDTYYR  60
DSVKGRFTIS RDNAKNSLYL QMNSLRAEDT AVYYCAAPPQ TYEGSIYRLW FAHWGQGTLV  120
TVSS                                                                 124

SEQ ID NO: 54          moltype = AA  length = 107
FEATURE                Location/Qualifiers
source                 1..107
                       mol_type = protein
```

```
                        organism = synthetic construct
SEQUENCE: 54
DIQLTQSPSS LSASVGDRVT ITCRADESVK TLMHWYQQKP GKAPKLLIYL VSNSEIGVPD  60
RFSGSGSGTD FRLTISSLQP EDFATYYCQQ TYSAPHTFGQ GTKVEIK               107

SEQ ID NO: 55           moltype = AA  length = 5
FEATURE                 Location/Qualifiers
source                  1..5
                        mol_type = protein
                        organism = synthetic construct
SEQUENCE: 55
TYAMA                                                             5

SEQ ID NO: 56           moltype = AA  length = 17
FEATURE                 Location/Qualifiers
source                  1..17
                        mol_type = protein
                        organism = synthetic construct
SEQUENCE: 56
TIRGSGESTY YRDSVKG                                                17

SEQ ID NO: 57           moltype = AA  length = 16
FEATURE                 Location/Qualifiers
source                  1..16
                        mol_type = protein
                        organism = synthetic construct
SEQUENCE: 57
PPQYYEGSID RLWFAH                                                 16

SEQ ID NO: 58           moltype = AA  length = 9
FEATURE                 Location/Qualifiers
source                  1..9
                        mol_type = protein
                        organism = synthetic construct
SEQUENCE: 58
LQTYSYPFT                                                         9

SEQ ID NO: 59           moltype = AA  length = 8
FEATURE                 Location/Qualifiers
source                  1..8
                        mol_type = protein
                        organism = synthetic construct
SEQUENCE: 59
GFPFSTYA                                                          8

SEQ ID NO: 60           moltype = AA  length = 8
FEATURE                 Location/Qualifiers
source                  1..8
                        mol_type = protein
                        organism = synthetic construct
SEQUENCE: 60
IRGSGEST                                                          8

SEQ ID NO: 61           moltype = AA  length = 18
FEATURE                 Location/Qualifiers
source                  1..18
                        mol_type = protein
                        organism = synthetic construct
SEQUENCE: 61
ASPPQYYEGS IDRLWFAH                                               18

SEQ ID NO: 62           moltype = AA  length = 7
FEATURE                 Location/Qualifiers
source                  1..7
                        mol_type = protein
                        organism = synthetic construct
SEQUENCE: 62
GFPFSTY                                                           7

SEQ ID NO: 63           moltype = AA  length = 6
FEATURE                 Location/Qualifiers
source                  1..6
                        mol_type = protein
                        organism = synthetic construct
SEQUENCE: 63
RGSGES                                                            6

SEQ ID NO: 64           moltype = AA  length = 14
FEATURE                 Location/Qualifiers
```

```
source                  1..14
                        mol_type = protein
                        organism = synthetic construct
SEQUENCE: 64
PQYYEGSIDR LWFA                                                         14

SEQ ID NO: 65           moltype = AA  length = 6
FEATURE                 Location/Qualifiers
source                  1..6
                        mol_type = protein
                        organism = synthetic construct
SEQUENCE: 65
TYSYPF                                                                  6

SEQ ID NO: 66           moltype = AA  length = 125
FEATURE                 Location/Qualifiers
source                  1..125
                        mol_type = protein
                        organism = synthetic construct
SEQUENCE: 66
EVQLVESGGG LVQPGGSLRL SCAASGFPFS TYAMAWVRQA PGKGLEWVAT IRGSGESTYY  60
RDSVKGRFTI SRDNAKNSLY LQMNSLRAED TAVYYCASPP QYYEGSIDRL WFAHWGQGTL  120
VTVSS                                                                   125

SEQ ID NO: 67           moltype = AA  length = 107
FEATURE                 Location/Qualifiers
source                  1..107
                        mol_type = protein
                        organism = synthetic construct
SEQUENCE: 67
AIQLTQSPSS LSASVGDRVT ITCRADESVR TLMHWYQQKP GKAPKLLIYL VSNSEIGVPD  60
RFSGSGSGTD FRLTISSLQP EDFATYYCLQ TYSYPFTFGQ GTKVEIK                    107

SEQ ID NO: 68           moltype = AA  length = 107
FEATURE                 Location/Qualifiers
source                  1..107
                        mol_type = protein
                        organism = synthetic construct
SEQUENCE: 68
DIQLTQSPSS LSASVGDRVT ITCRADESVR TLMHWYQQKP GKAPKLLIYL VSNSEIGVPD  60
RFSGSGSGTD FRLTISSLQP EDFATYYCLQ TYSYPFTFGQ GTKVEIK                    107

SEQ ID NO: 69           moltype = AA  length = 5
FEATURE                 Location/Qualifiers
source                  1..5
                        mol_type = protein
                        organism = synthetic construct
SEQUENCE: 69
DYNMA                                                                   5

SEQ ID NO: 70           moltype = AA  length = 17
FEATURE                 Location/Qualifiers
source                  1..17
                        mol_type = protein
                        organism = synthetic construct
SEQUENCE: 70
TITYEGRNTY YRDSVKG                                                      17

SEQ ID NO: 71           moltype = AA  length = 16
FEATURE                 Location/Qualifiers
source                  1..16
                        mol_type = protein
                        organism = synthetic construct
SEQUENCE: 71
PPQYYEGSIY RLWFAH                                                       16

SEQ ID NO: 72           moltype = AA  length = 9
FEATURE                 Location/Qualifiers
source                  1..9
                        mol_type = protein
                        organism = synthetic construct
SEQUENCE: 72
QQTWSDPWT                                                               9

SEQ ID NO: 73           moltype = AA  length = 8
FEATURE                 Location/Qualifiers
source                  1..8
                        mol_type = protein
                        organism = synthetic construct
```

```
SEQUENCE: 73
GFTFSDYN                                                            8

SEQ ID NO: 74          moltype = AA  length = 8
FEATURE                Location/Qualifiers
source                 1..8
                       mol_type = protein
                       organism = synthetic construct
SEQUENCE: 74
ITYEGRNT                                                            8

SEQ ID NO: 75          moltype = AA  length = 18
FEATURE                Location/Qualifiers
source                 1..18
                       mol_type = protein
                       organism = synthetic construct
SEQUENCE: 75
ASPPQYYEGS IYRLWFAH                                                 18

SEQ ID NO: 76          moltype = AA  length = 7
FEATURE                Location/Qualifiers
source                 1..7
                       mol_type = protein
                       organism = synthetic construct
SEQUENCE: 76
GFTFSDY                                                             7

SEQ ID NO: 77          moltype = AA  length = 6
FEATURE                Location/Qualifiers
source                 1..6
                       mol_type = protein
                       organism = synthetic construct
SEQUENCE: 77
TYEGRN                                                              6

SEQ ID NO: 78          moltype = AA  length = 14
FEATURE                Location/Qualifiers
source                 1..14
                       mol_type = protein
                       organism = synthetic construct
SEQUENCE: 78
PQYYEGSIYR LWFA                                                     14

SEQ ID NO: 79          moltype = AA  length = 6
FEATURE                Location/Qualifiers
source                 1..6
                       mol_type = protein
                       organism = synthetic construct
SEQUENCE: 79
TWSDPW                                                              6

SEQ ID NO: 80          moltype = AA  length = 125
FEATURE                Location/Qualifiers
source                 1..125
                       mol_type = protein
                       organism = synthetic construct
SEQUENCE: 80
EVQLVESGGG LVQPGGSLRL SCAASGFTFS DYNMAWVRQA PGKGLEWVAT ITYEGRNTYY  60
RDSVKGRFTI SRDNAKNSLY LQMNSLRAED TAVYYCASPP QYYEGSIYRL WFAHWGQGTL  120
VTVSS                                                               125

SEQ ID NO: 81          moltype = AA  length = 107
FEATURE                Location/Qualifiers
source                 1..107
                       mol_type = protein
                       organism = synthetic construct
SEQUENCE: 81
DIQLTQSPSS LSASVGDRVT ITCRADESVR TLMHWYQQKP GKAPKLLIYL VSNSEIGVPD  60
RFSGSGSGTD FRLTISSLQP EDFATYYCQQ TWSDPWTFGQ GTKVEIK                 107

SEQ ID NO: 82          moltype = AA  length = 107
FEATURE                Location/Qualifiers
source                 1..107
                       mol_type = protein
                       organism = synthetic construct
SEQUENCE: 82
DIQMTQSPSS LSASVGDRVT ITCRADESVR TLMHWYQQKP GKAPKLLIYL VSNSEIGVPD  60
RFSGSGSGTD FRLTISSLQP EDFATYYCQQ TWSDPWTFGQ GTKVEIK                 107
```

```
SEQ ID NO: 83           moltype = AA  length = 107
FEATURE                 Location/Qualifiers
source                  1..107
                        mol_type = protein
                        organism = synthetic construct
SEQUENCE: 83
AIQLTQSPSS LSASVGDRVT ITCRADESVR TLMHWYQQKP GKAPKLLIYL VSNSEIGVPD  60
RFSGSGSGTD FRLTISSLQP EDFATYYCQQ TWSDPWTFGQ GTKVEIK                107

SEQ ID NO: 84           moltype = AA  length = 329
FEATURE                 Location/Qualifiers
source                  1..329
                        mol_type = protein
                        organism = Homo sapiens
SEQUENCE: 84
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                    329

SEQ ID NO: 85           moltype = AA  length = 327
FEATURE                 Location/Qualifiers
source                  1..327
                        mol_type = protein
                        organism = Homo sapiens
SEQUENCE: 85
ASTKGPSVFP LAPCSRSTSE STAALGCLVK DYFPEPVTVS WNSGALTSGV HTFPAVLQSS  60
GLYSLSSVVT VPSSSLGTKT YTCNVDHKPS NTKVDKRVES KYGPPCPSCP APEFLGGPSV  120
FLFPPKPKDT LMISRTPEVT CVVVDVSQED PEVQFNWYVD GVEVHNAKTK PREEQFNSTY  180
RVVSVLTVLH QDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVMHE ALHNHYTQKS LSLSLGK                                      327

SEQ ID NO: 86           moltype = AA  length = 325
FEATURE                 Location/Qualifiers
source                  1..325
                        mol_type = protein
                        organism = Homo sapiens
SEQUENCE: 86
ASTKGPSVFP LAPCSRSTSE STAALGCLVK DYFPEPVTVS WNSGALTSGV HTFPAVLQSS  60
GLYSLSSVVT VPSSNFGTQT YTCNVDHKPS NTKVDKTVER KCCVECPPCP APPVAGPSVF  120
LFPPKPKDTL MISRTPEVTC VVVDVSHEDP EVQFNWYVDG VEVHNAKTKP REEQFNSTFR  180
VVSVLTVVHQ DWLNGKEYKC KVSNKGLPAP IEKTISKTKG QPREPQVYTL PPSREEMTKN  240
QVSLTCLVKG FYPSDIAVEW ESNGQPENNY KTTPPMLDSD GSFFLYSKLT VDKSRWQQGN  300
VFSCSVMHEA LHNHYTQKSL SLSPG                                        325

SEQ ID NO: 87           moltype = AA  length = 327
FEATURE                 Location/Qualifiers
source                  1..327
                        mol_type = protein
                        organism = synthetic construct
SEQUENCE: 87
ASTKGPSVFP LAPCSRSTSE STAALGCLVK DYFPEPVTVS WNSGALTSGV HTFPAVLQSS  60
GLYSLSSVVT VPSSSLGTKT YTCNVDHKPS NTKVDKRVES KYGPPCPPCP APEFLGGPSV  120
FLFPPKPKDT LMISRTPEVT CVVVDVSQED PEVQFNWYVD GVEVHNAKTK PREEQFNSTY  180
RVVSVLTVLH QDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVMHE ALHNHYTQKS LSLSLGK                                      327

SEQ ID NO: 88           moltype = AA  length = 327
FEATURE                 Location/Qualifiers
source                  1..327
                        mol_type = protein
                        organism = synthetic construct
SEQUENCE: 88
ASTKGPSVFP LAPCSRSTSE STAALGCLVK DYFPEPVTVS WNSGALTSGV HTFPAVLQSS  60
GLYSLSSVVT VPSSSLGTKT YTCNVDHKPS NTKVDKRVES KYGPPCPPCP APEELGGPSV  120
FLFPPKPKDT LMISRTPEVT CVVVDVSQED PEVQFNWYVD GVEVHNAKTK PREEQFNSTY  180
RVVSVLTVLH QDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVMHE ALHNHYTQKS LSLSLGK                                      327

SEQ ID NO: 89           moltype = AA  length = 329
FEATURE                 Location/Qualifiers
source                  1..329
                        mol_type = protein
                        organism = synthetic construct
```

```
SEQUENCE: 89
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYA  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                   329

SEQ ID NO: 90           moltype = AA  length = 329
FEATURE                 Location/Qualifiers
source                  1..329
                        mol_type = protein
                        organism = synthetic construct
SEQUENCE: 90
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVAVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                   329

SEQ ID NO: 91           moltype = AA  length = 329
FEATURE                 Location/Qualifiers
source                  1..329
                        mol_type = protein
                        organism = synthetic construct
SEQUENCE: 91
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                   329

SEQ ID NO: 92           moltype = AA  length = 329
FEATURE                 Location/Qualifiers
source                  1..329
                        mol_type = protein
                        organism = synthetic construct
SEQUENCE: 92
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELAGA  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                   329

SEQ ID NO: 93           moltype = AA  length = 329
FEATURE                 Location/Qualifiers
source                  1..329
                        mol_type = protein
                        organism = synthetic construct
SEQUENCE: 93
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGA  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                   329

SEQ ID NO: 94           moltype = AA  length = 329
FEATURE                 Location/Qualifiers
source                  1..329
                        mol_type = protein
                        organism = synthetic construct
SEQUENCE: 94
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LGAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                   329

SEQ ID NO: 95           moltype = AA  length = 329
FEATURE                 Location/Qualifiers
source                  1..329
                        mol_type = protein
                        organism = synthetic construct
SEQUENCE: 95
```

```
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLYITREP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                   329

SEQ ID NO: 96          moltype = AA  length = 329
FEATURE                Location/Qualifiers
source                 1..329
                       mol_type = protein
                       organism = synthetic construct
SEQUENCE: 96
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLYITREP EVTCVVVDVS HEDPEVKFNW YVDGVEVHNA KTKPREEQYA  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                   329

SEQ ID NO: 97          moltype = AA  length = 329
FEATURE                Location/Qualifiers
source                 1..329
                       mol_type = protein
                       organism = synthetic construct
SEQUENCE: 97
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLYITREP EVTCVVVAVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                   329

SEQ ID NO: 98          moltype = AA  length = 329
FEATURE                Location/Qualifiers
source                 1..329
                       mol_type = protein
                       organism = synthetic construct
SEQUENCE: 98
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGG  120
PSVFLFPPKP KDTLYITREP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                   329

SEQ ID NO: 99          moltype = AA  length = 329
FEATURE                Location/Qualifiers
source                 1..329
                       mol_type = protein
                       organism = synthetic construct
SEQUENCE: 99
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELAGA  120
PSVFLFPPKP KDTLYITREP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                   329

SEQ ID NO: 100         moltype = AA  length = 329
FEATURE                Location/Qualifiers
source                 1..329
                       mol_type = protein
                       organism = synthetic construct
SEQUENCE: 100
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGA  120
PSVFLFPPKP KDTLYITREP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                   329

SEQ ID NO: 101         moltype = AA  length = 329
FEATURE                Location/Qualifiers
source                 1..329
                       mol_type = protein
                       organism = synthetic construct
SEQUENCE: 101
ASTKGPSVFP LAPSSKSTSG GTAALGCLVK DYFPEPVTVS WNSGALTSGV HTFPAVLQSS  60
```

```
GLYSLSSVVT VPSSSLGTQT YICNVNHKPS NTKVDKKVEP KSCDKTHTCP PCPAPEAAGG  120
PSVFLFPPKP KDTLYITREP EVTCVVVDVS HEDPEVKFNW YVDGVEVHNA KTKPREEQYN  180
STYRVVSVLT VLHQDWLNGK EYKCKVSNKA LGAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                    329

SEQ ID NO: 102          moltype = AA  length = 329
FEATURE                 Location/Qualifiers
source                  1..329
                        mol_type = protein
                        organism = synthetic construct
SEQUENCE: 102
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHSHYT QKSLSLSPG                                    329

SEQ ID NO: 103          moltype = AA  length = 329
FEATURE                 Location/Qualifiers
source                  1..329
                        mol_type = protein
                        organism = synthetic construct
SEQUENCE: 103
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYA  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHSHYT QKSLSLSPG                                    329

SEQ ID NO: 104          moltype = AA  length = 329
FEATURE                 Location/Qualifiers
source                  1..329
                        mol_type = protein
                        organism = synthetic construct
SEQUENCE: 104
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVAVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHSHYT QKSLSLSPG                                    329

SEQ ID NO: 105          moltype = AA  length = 329
FEATURE                 Location/Qualifiers
source                  1..329
                        mol_type = protein
                        organism = synthetic construct
SEQUENCE: 105
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHSHYT QKSLSLSPG                                    329

SEQ ID NO: 106          moltype = AA  length = 329
FEATURE                 Location/Qualifiers
source                  1..329
                        mol_type = protein
                        organism = synthetic construct
SEQUENCE: 106
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELAGA  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHSHYT QKSLSLSPG                                    329

SEQ ID NO: 107          moltype = AA  length = 329
FEATURE                 Location/Qualifiers
source                  1..329
                        mol_type = protein
                        organism = synthetic construct
SEQUENCE: 107
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGA  120
```

```
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHSHYT QKSLSLSPG                                    329

SEQ ID NO: 108          moltype = AA  length = 329
FEATURE                 Location/Qualifiers
source                  1..329
                        mol_type = protein
                        organism = synthetic construct
SEQUENCE: 108
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LGAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHSHYT QKSLSLSPG                                    329

SEQ ID NO: 109          moltype = AA  length = 329
FEATURE                 Location/Qualifiers
source                  1..329
                        mol_type = protein
                        organism = synthetic construct
SEQUENCE: 109
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VDHHDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHSHYT QKSLSLSPG                                    329

SEQ ID NO: 110          moltype = AA  length = 329
FEATURE                 Location/Qualifiers
source                  1..329
                        mol_type = protein
                        organism = synthetic construct
SEQUENCE: 110
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYA  180
STYRVVSVLT VDHHDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHSHYT QKSLSLSPG                                    329

SEQ ID NO: 111          moltype = AA  length = 329
FEATURE                 Location/Qualifiers
source                  1..329
                        mol_type = protein
                        organism = synthetic construct
SEQUENCE: 111
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVAVS HEDPEVKFNW YVDGVEVHNA KTKPREEQYN  180
STYRVVSVLT VDHHDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHSHYT QKSLSLSPG                                    329

SEQ ID NO: 112          moltype = AA  length = 329
FEATURE                 Location/Qualifiers
source                  1..329
                        mol_type = protein
                        organism = synthetic construct
SEQUENCE: 112
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGG  120
PSVFLFPPKP KDTLMISRTP EVTCVVVDVS HEDPEVKFNW YVDGVEVHNA KTKPREEQYN  180
STYRVVSVLT VDHHDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHSHYT QKSLSLSPG                                    329

SEQ ID NO: 113          moltype = AA  length = 329
FEATURE                 Location/Qualifiers
source                  1..329
                        mol_type = protein
                        organism = synthetic construct
SEQUENCE: 113
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELAGA  120
PSVFLFPPKP KDTLMISRTP EVTCVVVDVS HEDPEVKFNW YVDGVEVHNA KTKPREEQYN  180
```

```
STYRVVSVLT VDHHDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHSHYT QKSLSLSPG                                    329

SEQ ID NO: 114          moltype = AA  length = 329
FEATURE                 Location/Qualifiers
source                  1..329
                        mol_type = protein
                        organism = synthetic construct
SEQUENCE: 114
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGA  120
PSVFLFPPKP KDTLMISRTP EVTCVVVDVS HEDPEVKFNW YVDGVEVHNA KTKPREEQYN  180
STYRVVSVLT VDHHDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHSHYT QKSLSLSPG                                    329

SEQ ID NO: 115          moltype = AA  length = 329
FEATURE                 Location/Qualifiers
source                  1..329
                        mol_type = protein
                        organism = synthetic construct
SEQUENCE: 115
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGG  120
PSVFLFPPKP KDTLMISRTP EVTCVVVDVS HEDPEVKFNW YVDGVEVHNA KTKPREEQYN  180
STYRVVSVLT VDHHDWLNGK EYKCKVSNKA LGAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHSHYT QKSLSLSPG                                    329

SEQ ID NO: 116          moltype = AA  length = 327
FEATURE                 Location/Qualifiers
source                  1..327
                        mol_type = protein
                        organism = synthetic construct
SEQUENCE: 116
ASTKGPSVFP LAPCSRSTSE STAALGCLVK DYFPEPVTVS WNSGALTSGV HTFPAVLQSS  60
GLYSLSSVVT VPSSSLGTKT YTCNVDHKPS NTKVDKRVES KYGPPCPSCP APEFLGGPSV  120
FLFPPKPKDT LYITREPEVT CVVVDVSQED PEVQFNWYVD GVEVHNAKTK PREEQFNSTY  180
RVVSVLTVLH QDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVMHE ALHNHYTQKS LSLSLGK                                      327

SEQ ID NO: 117          moltype = AA  length = 327
FEATURE                 Location/Qualifiers
source                  1..327
                        mol_type = protein
                        organism = synthetic construct
SEQUENCE: 117
ASTKGPSVFP LAPCSRSTSE STAALGCLVK DYFPEPVTVS WNSGALTSGV HTFPAVLQSS  60
GLYSLSSVVT VPSSSLGTKT YTCNVDHKPS NTKVDKRVES KYGPPCPPCP APEFLGGPSV  120
FLFPPKPKDT LYITREPEVT CVVVDVSQED PEVQFNWYVD GVEVHNAKTK PREEQFNSTY  180
RVVSVLTVLH QDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVMHE ALHNHYTQKS LSLSLGK                                      327

SEQ ID NO: 118          moltype = AA  length = 327
FEATURE                 Location/Qualifiers
source                  1..327
                        mol_type = protein
                        organism = synthetic construct
SEQUENCE: 118
ASTKGPSVFP LAPCSRSTSE STAALGCLVK DYFPEPVTVS WNSGALTSGV HTFPAVLQSS  60
GLYSLSSVVT VPSSSLGTKT YTCNVDHKPS NTKVDKRVES KYGPPCPPCP APEELGGPSV  120
FLFPPKPKDT LYITREPEVT CVVVDVSQED PEVQFNWYVD GVEVHNAKTK PREEQFNSTY  180
RVVSVLTVLH QDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVMHE ALHNHYTQKS LSLSLGK                                      327

SEQ ID NO: 119          moltype = AA  length = 327
FEATURE                 Location/Qualifiers
source                  1..327
                        mol_type = protein
                        organism = synthetic construct
SEQUENCE: 119
ASTKGPSVFP LAPCSRSTSE STAALGCLVK DYFPEPVTVS WNSGALTSGV HTFPAVLQSS  60
GLYSLSSVVT VPSSSLGTKT YTCNVDHKPS NTKVDKRVES KYGPPCPSCP APEFLGGPSV  120
FLFPPKPKDT LMISRTPEVT CVVVDVSQED PEVQFNWYVD GVEVHNAKTK PREEQFNSTY  180
RVVSVLTVLH QDWLNGKEYK CKVSNKGLPS SIEKTISKAK GQPREPQVYT LPPSQEEMTK  240
```

```
NQVSLTCLVK GFYPSDIAVE WESNGQPENN YKTTPPVLDS DGSFFLYSRL TVDKSRWQEG  300
NVFSCSVLHE ALHSHYTQKS LSLSLGK                                     327

SEQ ID NO: 120          moltype = AA  length = 327
FEATURE                 Location/Qualifiers
source                  1..327
                        mol_type = protein
                        organism = synthetic construct
SEQUENCE: 120
ASTKGPSVFP LAPCSRSTSE STAALGCLVK DYFPEPVTVS WNSGALTSGV HTFPAVLQSS  60
GLYSLSSVVT VPSSSLGTKT YTCNVDHKPS NTKVDKRVES KYGPPCPPCP APEFLGGPSV  120
FLFPPKPKDT LMISRTPEVT CVVVDVSQED PEVQFNWYVD GVEVHNAKTK PREEQFNSTY  180
RVVSVLTVLH QDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVLHE ALHSHYTQKS LSLSLGK                                     327

SEQ ID NO: 121          moltype = AA  length = 327
FEATURE                 Location/Qualifiers
source                  1..327
                        mol_type = protein
                        organism = synthetic construct
SEQUENCE: 121
ASTKGPSVFP LAPCSRSTSE STAALGCLVK DYFPEPVTVS WNSGALTSGV HTFPAVLQSS  60
GLYSLSSVVT VPSSSLGTKT YTCNVDHKPS NTKVDKRVES KYGPPCPPCP APEELGGPSV  120
FLFPPKPKDT LMISRTPEVT CVVVDVSQED PEVQFNWYVD GVEVHNAKTK PREEQFNSTY  180
RVVSVLTVLH QDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVLHE ALHSHYTQKS LSLSLGK                                     327

SEQ ID NO: 122          moltype = AA  length = 327
FEATURE                 Location/Qualifiers
source                  1..327
                        mol_type = protein
                        organism = synthetic construct
SEQUENCE: 122
ASTKGPSVFP LAPCSRSTSE STAALGCLVK DYFPEPVTVS WNSGALTSGV HTFPAVLQSS  60
GLYSLSSVVT VPSSSLGTKT YTCNVDHKPS NTKVDKRVES KYGPPCPSCP APEFLGGPSV  120
FLFPPKPKDT LMISRTPEVT CVVVDVSQED PEVQFNWYVD GVEVHNAKTK PREEQFNSTY  180
RVVSVLTVDH HDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVMHE ALHSHYTQKS LSLSLGK                                     327

SEQ ID NO: 123          moltype = AA  length = 327
FEATURE                 Location/Qualifiers
source                  1..327
                        mol_type = protein
                        organism = synthetic construct
SEQUENCE: 123
ASTKGPSVFP LAPCSRSTSE STAALGCLVK DYFPEPVTVS WNSGALTSGV HTFPAVLQSS  60
GLYSLSSVVT VPSSSLGTKT YTCNVDHKPS NTKVDKRVES KYGPPCPPCP APEFLGGPSV  120
FLFPPKPKDT LMISRTPEVT CVVVDVSQED PEVQFNWYVD GVEVHNAKTK PREEQFNSTY  180
RVVSVLTVDH HDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVMHE ALHSHYTQKS LSLSLGK                                     327

SEQ ID NO: 124          moltype = AA  length = 327
FEATURE                 Location/Qualifiers
source                  1..327
                        mol_type = protein
                        organism = synthetic construct
SEQUENCE: 124
ASTKGPSVFP LAPCSRSTSE STAALGCLVK DYFPEPVTVS WNSGALTSGV HTFPAVLQSS  60
GLYSLSSVVT VPSSSLGTKT YTCNVDHKPS NTKVDKRVES KYGPPCPPCP APEELGGPSV  120
FLFPPKPKDT LMISRTPEVT CVVVDVSQED PEVQFNWYVD GVEVHNAKTK PREEQFNSTY  180
RVVSVLTVDH HDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVMHE ALHSHYTQKS LSLSLGK                                     327

SEQ ID NO: 125          moltype = AA  length = 325
FEATURE                 Location/Qualifiers
source                  1..325
                        mol_type = protein
                        organism = synthetic construct
SEQUENCE: 125
ASTKGPSVFP LAPCSRSTSE STAALGCLVK DYFPEPVTVS WNSGALTSGV HTFPAVLQSS  60
GLYSLSSVVT VPSSNFGTQT YTCNVDHKPS NTKVDKTVER KCCVECPPCP APPVAGPSVF  120
LFPPKPKDTL YITREPEVTC VVVDVSHEDP EVQFNWYVDG VEVHNAKTKP REEQFNSTFR  180
VVSVLTVVHQ DWLNGKEYKC KVSNKGLPAP IEKTISKTKG QPREPQVYTL PPSREEMTKN  240
QVSLTCLVKG FYPSDIAVEW ESNGQPENNY KTTPPMLDSD GSFFLYSKLT VDKSRWQQGN  300
```

```
VFSCSVMHEA LHNHYTQKSL SLSPG                                  325

SEQ ID NO: 126          moltype = AA  length = 325
FEATURE                 Location/Qualifiers
source                  1..325
                        mol_type = protein
                        organism = synthetic construct
SEQUENCE: 126
ASTKGPSVFP LAPCSRSTSE STAALGCLVK DYFPEPVTVS WNSGALTSGV HTFPAVLQSS  60
GLYSLSSVVT VPSSNFGTQT YTCNVDHKPS NTKVDKTVER KCCVECPPCP APPVAGPSVF  120
LFPPKPKDTL MISRTPEVTC VVVDVSHEDP EVQFNWYVDG VEVHNAKTKP REEQFNSTFR  180
VVSVLTVVHQ DWLNGKEYKC KVSNKGLPAP IEKTISKTKG QPREPQVYTL PPSREEMTKN  240
QVSLTCLVKG FYPSDIAVEW ESNGQPENNY KTTPPMLDSD GSFFLYSKLT VDKSRWQQGN  300
VFSCSVLHEA LHSHYTQKSL SLSPG                                  325

SEQ ID NO: 127          moltype = AA  length = 325
FEATURE                 Location/Qualifiers
source                  1..325
                        mol_type = protein
                        organism = synthetic construct
SEQUENCE: 127
ASTKGPSVFP LAPCSRSTSE STAALGCLVK DYFPEPVTVS WNSGALTSGV HTFPAVLQSS  60
GLYSLSSVVT VPSSNFGTQT YTCNVDHKPS NTKVDKTVER KCCVECPPCP APPVAGPSVF  120
LFPPKPKDTL MISRTPEVTC VVVDVSHEDP EVQFNWYVDG VEVHNAKTKP REEQFNSTFR  180
VVSVLTVDHH DWLNGKEYKC KVSNKGLPAP IEKTISKTKG QPREPQVYTL PPSREEMTKN  240
QVSLTCLVKG FYPSDIAVEW ESNGQPENNY KTTPPMLDSD GSFFLYSKLT VDKSRWQQGN  300
VFSCSVMHEA LHSHYTQKSL SLSPG                                  325

SEQ ID NO: 128          moltype = AA  length = 327
FEATURE                 Location/Qualifiers
source                  1..327
                        mol_type = protein
                        organism = synthetic construct
SEQUENCE: 128
ASTKGPSVFP LAPCSRSTSE STAALGCLVK DYFPEPVTVS WNSGALTSGV HTFPAVLQSS  60
GLYSLSSVVT VPSSSLGTKT YTCNVDHKPS NTKVDKRVES KYGPPCPPCP APEFLGGPSV  120
FLFPPKPKDT LMISRTPEVT CVVVDVSQED PEVQFNWYVD GVEVHNAKTK PREEQFNSTY  180
RVVSVLTVLH QDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVMHE ALHNHYTQKS LSLSLGK                                327

SEQ ID NO: 129          moltype = AA  length = 329
FEATURE                 Location/Qualifiers
source                  1..329
                        mol_type = protein
                        organism = synthetic construct
SEQUENCE: 129
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHAHYT QKSLSLSPG                              329

SEQ ID NO: 130          moltype = AA  length = 329
FEATURE                 Location/Qualifiers
source                  1..329
                        mol_type = protein
                        organism = synthetic construct
SEQUENCE: 130
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYA  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHAHYT QKSLSLSPG                              329

SEQ ID NO: 131          moltype = AA  length = 329
FEATURE                 Location/Qualifiers
source                  1..329
                        mol_type = protein
                        organism = synthetic construct
SEQUENCE: 131
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVAVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHAHYT QKSLSLSPG                              329
```

```
SEQ ID NO: 132          moltype = AA  length = 329
FEATURE                 Location/Qualifiers
source                  1..329
                        mol_type = protein
                        organism = synthetic construct
SEQUENCE: 132
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHAHYT QKSLSLSPG                                  329

SEQ ID NO: 133          moltype = AA  length = 329
FEATURE                 Location/Qualifiers
source                  1..329
                        mol_type = protein
                        organism = synthetic construct
SEQUENCE: 133
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELAGA  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHAHYT QKSLSLSPG                                  329

SEQ ID NO: 134          moltype = AA  length = 329
FEATURE                 Location/Qualifiers
source                  1..329
                        mol_type = protein
                        organism = synthetic construct
SEQUENCE: 134
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGA  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHAHYT QKSLSLSPG                                  329

SEQ ID NO: 135          moltype = AA  length = 329
FEATURE                 Location/Qualifiers
source                  1..329
                        mol_type = protein
                        organism = synthetic construct
SEQUENCE: 135
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LGAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHAHYT QKSLSLSPG                                  329

SEQ ID NO: 136          moltype = AA  length = 329
FEATURE                 Location/Qualifiers
source                  1..329
                        mol_type = protein
                        organism = synthetic construct
SEQUENCE: 136
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHAHYT QKSLSLSPG                                  329

SEQ ID NO: 137          moltype = AA  length = 329
FEATURE                 Location/Qualifiers
source                  1..329
                        mol_type = protein
                        organism = synthetic construct
SEQUENCE: 137
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYA  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHAHYT QKSLSLSPG                                  329
```

```
SEQ ID NO: 138          moltype = AA  length = 329
FEATURE                 Location/Qualifiers
source                  1..329
                        mol_type = protein
                        organism = synthetic construct
SEQUENCE: 138
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVAVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHAHYT QKSLSLSPG                                329

SEQ ID NO: 139          moltype = AA  length = 329
FEATURE                 Location/Qualifiers
source                  1..329
                        mol_type = protein
                        organism = synthetic construct
SEQUENCE: 139
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHAHYT QKSLSLSPG                                329

SEQ ID NO: 140          moltype = AA  length = 329
FEATURE                 Location/Qualifiers
source                  1..329
                        mol_type = protein
                        organism = synthetic construct
SEQUENCE: 140
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELAGA  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHAHYT QKSLSLSPG                                329

SEQ ID NO: 141          moltype = AA  length = 329
FEATURE                 Location/Qualifiers
source                  1..329
                        mol_type = protein
                        organism = synthetic construct
SEQUENCE: 141
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGA  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHAHYT QKSLSLSPG                                329

SEQ ID NO: 142          moltype = AA  length = 329
FEATURE                 Location/Qualifiers
source                  1..329
                        mol_type = protein
                        organism = synthetic construct
SEQUENCE: 142
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LGAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHAHYT QKSLSLSPG                                329

SEQ ID NO: 143          moltype = AA  length = 329
FEATURE                 Location/Qualifiers
source                  1..329
                        mol_type = protein
                        organism = synthetic construct
SEQUENCE: 143
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHWHYT QKSLSLSPG                                329

SEQ ID NO: 144          moltype = AA  length = 329
```

```
FEATURE                Location/Qualifiers
source                 1..329
                       mol_type = protein
                       organism = synthetic construct
SEQUENCE: 144
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYA  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHWHYT QKSLSLSPG                                   329

SEQ ID NO: 145         moltype = AA  length = 329
FEATURE                Location/Qualifiers
source                 1..329
                       mol_type = protein
                       organism = synthetic construct
SEQUENCE: 145
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVAVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHWHYT QKSLSLSPG                                   329

SEQ ID NO: 146         moltype = AA  length = 329
FEATURE                Location/Qualifiers
source                 1..329
                       mol_type = protein
                       organism = synthetic construct
SEQUENCE: 146
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHWHYT QKSLSLSPG                                   329

SEQ ID NO: 147         moltype = AA  length = 329
FEATURE                Location/Qualifiers
source                 1..329
                       mol_type = protein
                       organism = synthetic construct
SEQUENCE: 147
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELAGA  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHWHYT QKSLSLSPG                                   329

SEQ ID NO: 148         moltype = AA  length = 329
FEATURE                Location/Qualifiers
source                 1..329
                       mol_type = protein
                       organism = synthetic construct
SEQUENCE: 148
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGA  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHWHYT QKSLSLSPG                                   329

SEQ ID NO: 149         moltype = AA  length = 329
FEATURE                Location/Qualifiers
source                 1..329
                       mol_type = protein
                       organism = synthetic construct
SEQUENCE: 149
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LGAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHWHYT QKSLSLSPG                                   329

SEQ ID NO: 150         moltype = AA  length = 329
FEATURE                Location/Qualifiers
```

```
source                  1..329
                        mol_type = protein
                        organism = synthetic construct
SEQUENCE: 150
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRDP EVTCVVVDVS HEDPEVKFNW YVDGVEVHNA KTKPREEQYN  180
STYRVVSVLQ VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                   329

SEQ ID NO: 151          moltype = AA  length = 329
FEATURE                 Location/Qualifiers
source                  1..329
                        mol_type = protein
                        organism = synthetic construct
SEQUENCE: 151
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRDP EVTCVVVDVS HEDPEVKFNW YVDGVEVHNA KTKPREEQYA  180
STYRVVSVLQ VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                   329

SEQ ID NO: 152          moltype = AA  length = 329
FEATURE                 Location/Qualifiers
source                  1..329
                        mol_type = protein
                        organism = synthetic construct
SEQUENCE: 152
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRDP EVTCVVVAVS HEDPEVKFNW YVDGVEVHNA KTKPREEQYN  180
STYRVVSVLQ VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                   329

SEQ ID NO: 153          moltype = AA  length = 329
FEATURE                 Location/Qualifiers
source                  1..329
                        mol_type = protein
                        organism = synthetic construct
SEQUENCE: 153
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGG  120
PSVFLFPPKP KDTLMISRDP EVTCVVVDVS HEDPEVKFNW YVDGVEVHNA KTKPREEQYN  180
STYRVVSVLQ VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                   329

SEQ ID NO: 154          moltype = AA  length = 329
FEATURE                 Location/Qualifiers
source                  1..329
                        mol_type = protein
                        organism = synthetic construct
SEQUENCE: 154
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELAGA  120
PSVFLFPPKP KDTLMISRDP EVTCVVVDVS HEDPEVKFNW YVDGVEVHNA KTKPREEQYN  180
STYRVVSVLQ VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                   329

SEQ ID NO: 155          moltype = AA  length = 329
FEATURE                 Location/Qualifiers
source                  1..329
                        mol_type = protein
                        organism = synthetic construct
SEQUENCE: 155
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGA  120
PSVFLFPPKP KDTLMISRDP EVTCVVVDVS HEDPEVKFNW YVDGVEVHNA KTKPREEQYN  180
STYRVVSVLQ VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                   329

SEQ ID NO: 156          moltype = AA  length = 329
FEATURE                 Location/Qualifiers
source                  1..329
```

```
                        mol_type = protein
                        organism = synthetic construct
SEQUENCE: 156
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGG  120
PSVFLFPPKP KDTLMISRDP EVTCVVVDVS HEDPEVKFNW YVDGVEVHNA KTKPREEQYN  180
STYRVVSVLQ VLHQDWLNGK EYKCKVSNKA LGAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                    329

SEQ ID NO: 157          moltype = AA  length = 329
FEATURE                 Location/Qualifiers
source                  1..329
                        mol_type = protein
                        organism = synthetic construct
SEQUENCE: 157
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRDP EVTCVVVDVS HEDPEVKFNW YVDGVEVHNA KTKPREEQYN  180
STYRVVSVLW VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                    329

SEQ ID NO: 158          moltype = AA  length = 329
FEATURE                 Location/Qualifiers
source                  1..329
                        mol_type = protein
                        organism = synthetic construct
SEQUENCE: 158
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRDP EVTCVVVDVS HEDPEVKFNW YVDGVEVHNA KTKPREEQYA  180
STYRVVSVLW VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                    329

SEQ ID NO: 159          moltype = AA  length = 329
FEATURE                 Location/Qualifiers
source                  1..329
                        mol_type = protein
                        organism = synthetic construct
SEQUENCE: 159
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRDP EVTCVVVAVS HEDPEVKFNW YVDGVEVHNA KTKPREEQYN  180
STYRVVSVLW VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                    329

SEQ ID NO: 160          moltype = AA  length = 329
FEATURE                 Location/Qualifiers
source                  1..329
                        mol_type = protein
                        organism = synthetic construct
SEQUENCE: 160
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGG  120
PSVFLFPPKP KDTLMISRDP EVTCVVVDVS HEDPEVKFNW YVDGVEVHNA KTKPREEQYN  180
STYRVVSVLW VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                    329

SEQ ID NO: 161          moltype = AA  length = 329
FEATURE                 Location/Qualifiers
source                  1..329
                        mol_type = protein
                        organism = synthetic construct
SEQUENCE: 161
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELAGA  120
PSVFLFPPKP KDTLMISRDP EVTCVVVDVS HEDPEVKFNW YVDGVEVHNA KTKPREEQYN  180
STYRVVSVLW VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                    329

SEQ ID NO: 162          moltype = AA  length = 329
FEATURE                 Location/Qualifiers
source                  1..329
                        mol_type = protein
```

```
                         organism = synthetic construct
SEQUENCE: 162
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGA  120
PSVFLFPPKP KDTLMISRDP EVTCVVVDVS HEDPEVKFNW YVDGVEVHNA KTKPREEQYN  180
STYRVVSVLW VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                   329

SEQ ID NO: 163           moltype = AA  length = 329
FEATURE                  Location/Qualifiers
source                   1..329
                         mol_type = protein
                         organism = synthetic construct
SEQUENCE: 163
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGG  120
PSVFLFPPKP KDTLMISRDP EVTCVVVDVS HEDPEVKFNW YVDGVEVHNA KTKPREEQYN  180
STYRVVSVLW VLHQDWLNGK EYKCKVSNKA LGAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                   329

SEQ ID NO: 164           moltype = AA  length = 329
FEATURE                  Location/Qualifiers
source                   1..329
                         mol_type = protein
                         organism = synthetic construct
SEQUENCE: 164
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLYISRDP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                   329

SEQ ID NO: 165           moltype = AA  length = 329
FEATURE                  Location/Qualifiers
source                   1..329
                         mol_type = protein
                         organism = synthetic construct
SEQUENCE: 165
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLYISRDP EVTCVVVDVS HEDPEVKFNW YVDGVEVHNA KTKPREEQYA  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                   329

SEQ ID NO: 166           moltype = AA  length = 329
FEATURE                  Location/Qualifiers
source                   1..329
                         mol_type = protein
                         organism = synthetic construct
SEQUENCE: 166
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLYISRDP EVTCVVVAVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                   329

SEQ ID NO: 167           moltype = AA  length = 329
FEATURE                  Location/Qualifiers
source                   1..329
                         mol_type = protein
                         organism = synthetic construct
SEQUENCE: 167
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGG  120
PSVFLFPPKP KDTLYISRDP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                   329

SEQ ID NO: 168           moltype = AA  length = 329
FEATURE                  Location/Qualifiers
source                   1..329
                         mol_type = protein
                         organism = synthetic construct
```

```
SEQUENCE: 168
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELAGA  120
PSVFLFPPKP KDTLYISRDP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                   329

SEQ ID NO: 169          moltype = AA  length = 329
FEATURE                 Location/Qualifiers
source                  1..329
                        mol_type = protein
                        organism = synthetic construct
SEQUENCE: 169
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGA  120
PSVFLFPPKP KDTLYISRDP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                   329

SEQ ID NO: 170          moltype = AA  length = 329
FEATURE                 Location/Qualifiers
source                  1..329
                        mol_type = protein
                        organism = synthetic construct
SEQUENCE: 170
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGG  120
PSVFLFPPKP KDTLYISRDP EVTCVVVDVS HEDPEVKFNW YVDGVEVHNA KTKPREEQYN  180
STYRVVSVLT VLHQDWLNGK EYKCKVSNKA LGAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                   329

SEQ ID NO: 171          moltype = AA  length = 329
FEATURE                 Location/Qualifiers
source                  1..329
                        mol_type = protein
                        organism = synthetic construct
SEQUENCE: 171
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLQ VLHVDWLNGK EYKCKVSNKA LPAPIEKTIS KAKGQPREPQ VYTLPPSRDE  240
LTKNQVSLTC LVKGFYPSDI VVEWESNGQP ENNYKTTPPV LDSDGSFFLY SKLTVDKSRW  300
QQGNVFSCSV MHEALHNHYT QKSLSLSPG                                   329

SEQ ID NO: 172          moltype = AA  length = 329
FEATURE                 Location/Qualifiers
source                  1..329
                        mol_type = protein
                        organism = synthetic construct
SEQUENCE: 172
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYA  180
STYRVVSVLQ VLHVDWLNGK EYKCKVSNKA LPAPIEKTIS KAKGQPREPQ VYTLPPSRDE  240
LTKNQVSLTC LVKGFYPSDI VVEWESNGQP ENNYKTTPPV LDSDGSFFLY SKLTVDKSRW  300
QQGNVFSCSV MHEALHNHYT QKSLSLSPG                                   329

SEQ ID NO: 173          moltype = AA  length = 329
FEATURE                 Location/Qualifiers
source                  1..329
                        mol_type = protein
                        organism = synthetic construct
SEQUENCE: 173
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVAVS HEDPEVKFNW YVDGVEVHNA KTKPREEQYN  180
STYRVVSVLQ VLHVDWLNGK EYKCKVSNKA LPAPIEKTIS KAKGQPREPQ VYTLPPSRDE  240
LTKNQVSLTC LVKGFYPSDI VVEWESNGQP ENNYKTTPPV LDSDGSFFLY SKLTVDKSRW  300
QQGNVFSCSV MHEALHNHYT QKSLSLSPG                                   329

SEQ ID NO: 174          moltype = AA  length = 329
FEATURE                 Location/Qualifiers
source                  1..329
                        mol_type = protein
                        organism = synthetic construct
SEQUENCE: 174
```

```
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGG  120
PSVFLFPPKP KDTLMISRTP EVTCVVVDVS HEDPEVKFNW YVDGVEVHNA KTKPREEQYN  180
STYRVVSVLQ VLHVDWLNGK EYKCKVSNKA LPAPIEKTIS KAKGQPREPQ VYTLPPSRDE  240
LTKNQVSLTC LVKGFYPSDI VVEWESNGQP ENNYKTTPPV LDSDGSFFLY SKLTVDKSRW  300
QQGNVFSCSV MHEALHNHYT QKSLSLSPG                                  329

SEQ ID NO: 175          moltype = AA  length = 329
FEATURE                 Location/Qualifiers
source                  1..329
                        mol_type = protein
                        organism = synthetic construct
SEQUENCE: 175
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELAGA  120
PSVFLFPPKP KDTLMISRTP EVTCVVVDVS HEDPEVKFNW YVDGVEVHNA KTKPREEQYN  180
STYRVVSVLQ VLHVDWLNGK EYKCKVSNKA LPAPIEKTIS KAKGQPREPQ VYTLPPSRDE  240
LTKNQVSLTC LVKGFYPSDI VVEWESNGQP ENNYKTTPPV LDSDGSFFLY SKLTVDKSRW  300
QQGNVFSCSV MHEALHNHYT QKSLSLSPG                                  329

SEQ ID NO: 176          moltype = AA  length = 329
FEATURE                 Location/Qualifiers
source                  1..329
                        mol_type = protein
                        organism = synthetic construct
SEQUENCE: 176
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGA  120
PSVFLFPPKP KDTLMISRTP EVTCVVVDVS HEDPEVKFNW YVDGVEVHNA KTKPREEQYN  180
STYRVVSVLQ VLHVDWLNGK EYKCKVSNKA LPAPIEKTIS KAKGQPREPQ VYTLPPSRDE  240
LTKNQVSLTC LVKGFYPSDI VVEWESNGQP ENNYKTTPPV LDSDGSFFLY SKLTVDKSRW  300
QQGNVFSCSV MHEALHNHYT QKSLSLSPG                                  329

SEQ ID NO: 177          moltype = AA  length = 329
FEATURE                 Location/Qualifiers
source                  1..329
                        mol_type = protein
                        organism = synthetic construct
SEQUENCE: 177
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGG  120
PSVFLFPPKP KDTLMISRTP EVTCVVVDVS HEDPEVKFNW YVDGVEVHNA KTKPREEQYN  180
STYRVVSVLQ VLHVDWLNGK EYKCKVSNKA LGAPIEKTIS KAKGQPREPQ VYTLPPSRDE  240
LTKNQVSLTC LVKGFYPSDI VVEWESNGQP ENNYKTTPPV LDSDGSFFLY SKLTVDKSRW  300
QQGNVFSCSV MHEALHNHYT QKSLSLSPG                                  329

SEQ ID NO: 178          moltype = AA  length = 329
FEATURE                 Location/Qualifiers
source                  1..329
                        mol_type = protein
                        organism = synthetic construct
SEQUENCE: 178
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRDP EVTCVVVDVS HEDPEVKFNW YVDGVEVDNA KTKPREEQYN  180
STYRVVSVLR VLHVDWLNGK EYKCKVSNKA LPAPIEKTIS KAKGQPREPQ VYTLPPSRDE  240
LTKNQVSLTC LVKGFYPSDI VVEWESNGQP ENNYKTTPPV LDSDGSFFLY SKLTVDKSRW  300
QQGNVFSCSV MHEALHNHYT QKSLSLSPG                                  329

SEQ ID NO: 179          moltype = AA  length = 329
FEATURE                 Location/Qualifiers
source                  1..329
                        mol_type = protein
                        organism = synthetic construct
SEQUENCE: 179
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRDP EVTCVVVDVS HEDPEVKFNW YVDGVEVDNA KTKPREEQYA  180
STYRVVSVLR VLHVDWLNGK EYKCKVSNKA LPAPIEKTIS KAKGQPREPQ VYTLPPSRDE  240
LTKNQVSLTC LVKGFYPSDI VVEWESNGQP ENNYKTTPPV LDSDGSFFLY SKLTVDKSRW  300
QQGNVFSCSV MHEALHNHYT QKSLSLSPG                                  329

SEQ ID NO: 180          moltype = AA  length = 329
FEATURE                 Location/Qualifiers
source                  1..329
                        mol_type = protein
                        organism = synthetic construct
SEQUENCE: 180
ASTKGPSVFP LAPSSKSTSG GTAALGCLVK DYFPEPVTVS WNSGALTSGV HTFPAVLQSS  60
```

```
GLYSLSSVVT VPSSSLGTQT YICNVNHKPS NTKVDKKVEP KSCDKTHTCP PCPAPELLGG  120
PSVFLFPPKP KDTLMISRDP EVTCVVVAVS HEDPEVKFNW YVDGVEVDNA KTKPREEQYN  180
STYRVVSVLR VLHVDWLNGK EYKCKVSNKA LPAPIEKTIS KAKGQPREPQ VYTLPPSRDE  240
LTKNQVSLTC LVKGFYPSDI VVEWESNGQP ENNYKTTPPV LDSDGSFFLY SKLTVDKSRW  300
QQGNVFSCSV MHEALHNHYT QKSLSLSPG                                  329

SEQ ID NO: 181         moltype = AA  length = 329
FEATURE                Location/Qualifiers
source                 1..329
                       mol_type = protein
                       organism = synthetic construct
SEQUENCE: 181
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGG  120
PSVFLFPPKP KDTLMISRDP EVTCVVVDVS HEDPEVKFNW YVDGVEVDNA KTKPREEQYN  180
STYRVVSVLR VLHVDWLNGK EYKCKVSNKA LPAPIEKTIS KAKGQPREPQ VYTLPPSRDE  240
LTKNQVSLTC LVKGFYPSDI VVEWESNGQP ENNYKTTPPV LDSDGSFFLY SKLTVDKSRW  300
QQGNVFSCSV MHEALHNHYT QKSLSLSPG                                  329

SEQ ID NO: 182         moltype = AA  length = 329
FEATURE                Location/Qualifiers
source                 1..329
                       mol_type = protein
                       organism = synthetic construct
SEQUENCE: 182
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELAGA  120
PSVFLFPPKP KDTLMISRDP EVTCVVVDVS HEDPEVKFNW YVDGVEVDNA KTKPREEQYN  180
STYRVVSVLR VLHVDWLNGK EYKCKVSNKA LPAPIEKTIS KAKGQPREPQ VYTLPPSRDE  240
LTKNQVSLTC LVKGFYPSDI VVEWESNGQP ENNYKTTPPV LDSDGSFFLY SKLTVDKSRW  300
QQGNVFSCSV MHEALHNHYT QKSLSLSPG                                  329

SEQ ID NO: 183         moltype = AA  length = 329
FEATURE                Location/Qualifiers
source                 1..329
                       mol_type = protein
                       organism = synthetic construct
SEQUENCE: 183
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGA  120
PSVFLFPPKP KDTLMISRDP EVTCVVVDVS HEDPEVKFNW YVDGVEVDNA KTKPREEQYN  180
STYRVVSVLR VLHVDWLNGK EYKCKVSNKA LPAPIEKTIS KAKGQPREPQ VYTLPPSRDE  240
LTKNQVSLTC LVKGFYPSDI VVEWESNGQP ENNYKTTPPV LDSDGSFFLY SKLTVDKSRW  300
QQGNVFSCSV MHEALHNHYT QKSLSLSPG                                  329

SEQ ID NO: 184         moltype = AA  length = 329
FEATURE                Location/Qualifiers
source                 1..329
                       mol_type = protein
                       organism = synthetic construct
SEQUENCE: 184
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGG  120
PSVFLFPPKP KDTLMISRDP EVTCVVVDVS HEDPEVKFNW YVDGVEVDNA KTKPREEQYN  180
STYRVVSVLR VLHVDWLNGK EYKCKVSNKA LGAPIEKTIS KAKGQPREPQ VYTLPPSRDE  240
LTKNQVSLTC LVKGFYPSDI VVEWESNGQP ENNYKTTPPV LDSDGSFFLY SKLTVDKSRW  300
QQGNVFSCSV MHEALHNHYT QKSLSLSPG                                  329

SEQ ID NO: 185         moltype = AA  length = 329
FEATURE                Location/Qualifiers
source                 1..329
                       mol_type = protein
                       organism = synthetic construct
SEQUENCE: 185
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHRDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHNHYT QKSLSLSPG                                  329

SEQ ID NO: 186         moltype = AA  length = 327
FEATURE                Location/Qualifiers
source                 1..327
                       mol_type = protein
                       organism = synthetic construct
SEQUENCE: 186
ASTKGPSVFP LAPCSRSTSE STAALGCLVK DYFPEPVTVS WNSGALTSGV HTFPAVLQSS  60
GLYSLSSVVT VPSSSLGTKT YTCNVDHKPS NTKVDKRVES KYGPPCPSCP APEFLGGPSV  120
```

```
FLFPPKPKDT LMISRTPEVT CVVVDVSQED PEVQFNWYVD GVEVHNAKTK PREEQFNSTY  180
RVVSVLTVLH RDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVLHE ALHNHYTQKS LSLSLGK                                     327

SEQ ID NO: 187          moltype = AA  length = 327
FEATURE                 Location/Qualifiers
source                  1..327
                        mol_type = protein
                        organism = synthetic construct
SEQUENCE: 187
ASTKGPSVFP LAPCSRSTSE STAALGCLVK DYFPEPVTVS WNSGALTSGV HTFPAVLQSS  60
GLYSLSSVVT VPSSSLGTKT YTCNVDHKPS NTKVDKRVES KYGPPCPPCP APEFLGGPSV  120
FLFPPKPKDT LMISRTPEVT CVVVDVSQED PEVQFNWYVD GVEVHNAKTK PREEQFNSTY  180
RVVSVLTVLH RDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVLHE ALHNHYTQKS LSLSLGK                                     327

SEQ ID NO: 188          moltype = AA  length = 327
FEATURE                 Location/Qualifiers
source                  1..327
                        mol_type = protein
                        organism = synthetic construct
SEQUENCE: 188
ASTKGPSVFP LAPCSRSTSE STAALGCLVK DYFPEPVTVS WNSGALTSGV HTFPAVLQSS  60
GLYSLSSVVT VPSSSLGTKT YTCNVDHKPS NTKVDKRVES KYGPPCPPCP APEELGGPSV  120
FLFPPKPKDT LMISRTPEVT CVVVDVSQED PEVQFNWYVD GVEVHNAKTK PREEQFNSTY  180
RVVSVLTVLH RDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVLHE ALHNHYTQKS LSLSLGK                                     327

SEQ ID NO: 189          moltype = AA  length = 324
FEATURE                 Location/Qualifiers
source                  1..324
                        mol_type = protein
                        organism = synthetic construct
SEQUENCE: 189
ASTKGPSVFP LAPCSRSTSE STAALGCLVK DYFPEPVTVS WNSGALTSGV HTFPAVLQSS  60
GLYSLSSVVT VPSSNFGTQT YTCNVDHKPS NTKVDKTVER KCCVECPPCP APPVAGPSVF  120
LFPPKPKDTL MISRTPEVTC VVVDVSHEDP EVQFNWYVDG VEVHNAKTKP REEQFNSTFR  180
VVSVLTVVHR DWLNGKEYKC KVSNKGLPAP IEKTISKTKG QPREPQVYTL PPSREEMTKN  240
QVSLTCLVKG FYPSDIAVEW ESNGQPENNY KTTPPMLDSD GSFFLYSKLT VDKSRWQQGN  300
VFSCSVLHEA LHNHYTQKSL SLSP                                        324

SEQ ID NO: 190          moltype = AA  length = 329
FEATURE                 Location/Qualifiers
source                  1..329
                        mol_type = protein
                        organism = synthetic construct
SEQUENCE: 190
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYA  180
STYRVVSVLT VLHRDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHNHYT QKSLSLSPG                                   329

SEQ ID NO: 191          moltype = AA  length = 329
FEATURE                 Location/Qualifiers
source                  1..329
                        mol_type = protein
                        organism = synthetic construct
SEQUENCE: 191
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVAVS HEDPEVKFNW YVDGVEVHNA KTKPREEQYN  180
STYRVVSVLT VLHRDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHNHYT QKSLSLSPG                                   329

SEQ ID NO: 192          moltype = AA  length = 329
FEATURE                 Location/Qualifiers
source                  1..329
                        mol_type = protein
                        organism = synthetic construct
SEQUENCE: 192
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGG  120
PSVFLFPPKP KDTLMISRTP EVTCVVVDVS HEDPEVKFNW YVDGVEVHNA KTKPREEQYN  180
```

```
STYRVVSVLT VLHRDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHNHYT QKSLSLSPG                                    329

SEQ ID NO: 193          moltype = AA  length = 329
FEATURE                 Location/Qualifiers
source                  1..329
                        mol_type = protein
                        organism = synthetic construct
SEQUENCE: 193
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELAGA  120
PSVFLFPPKP KDTLMISRTP EVTCVVVDVS HEDPEVKFNW YVDGVEVHNA KTKPREEQYN  180
STYRVVSVLT VLHRDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHNHYT QKSLSLSPG                                    329

SEQ ID NO: 194          moltype = AA  length = 329
FEATURE                 Location/Qualifiers
source                  1..329
                        mol_type = protein
                        organism = synthetic construct
SEQUENCE: 194
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGA  120
PSVFLFPPKP KDTLMISRTP EVTCVVVDVS HEDPEVKFNW YVDGVEVHNA KTKPREEQYN  180
STYRVVSVLT VLHRDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHNHYT QKSLSLSPG                                    329

SEQ ID NO: 195          moltype = AA  length = 329
FEATURE                 Location/Qualifiers
source                  1..329
                        mol_type = protein
                        organism = synthetic construct
SEQUENCE: 195
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGG  120
PSVFLFPPKP KDTLMISRTP EVTCVVVDVS HEDPEVKFNW YVDGVEVHNA KTKPREEQYN  180
STYRVVSVLT VLHRDWLNGK EYKCKVSNKA LGAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHNHYT QKSLSLSPG                                    329

SEQ ID NO: 196          moltype = AA  length = 453
FEATURE                 Location/Qualifiers
source                  1..453
                        mol_type = protein
                        organism = synthetic construct
SEQUENCE: 196
EVQLVESGGG LVQPGGSLRL SCAASGFPFS DYSMAWVRQA PGKGLEWVAT IGPSGDTYYR  60
DSVKGRFTIS RDNAKNSLYL QMNSLRAEDT AVYYCASPPQ YYEGSIPRLW PAHWGQGTLV  120
TVSSASTKGP SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK KVEPKSCDKT HTCPPCPAPE  240
LLGGPSVFLF PPKPKDTLYI TREPEVTCVV VDVSHEDPEV KFNWYVDGVE VHNAKTKPRE  300
EQYNSTYRVV SVLTVLHQDW LNGKEYKCKV SNKALPAPIE KTISKAKGQP REPQVYTLPP  360
SRDELTKNQV SLTCLVKGFY PSDIAVEWES NGQPENNYKT TPPVLDSDGS FFLYSKLTVD  420
KSRWQQGNVF SCSVMHEALH NHYTQKSLSL SPG                               453

SEQ ID NO: 197          moltype = AA  length = 214
FEATURE                 Location/Qualifiers
source                  1..214
                        mol_type = protein
                        organism = synthetic construct
SEQUENCE: 197
AIQLTQSPSS LSASVGDRVT ITCRADESVR TLMHWYQQKP GKAPKLLIYL VSNSEIGVPD  60
RFSGSGSGTD FRLTISSLQP EDFATYYCLQ THSYPYTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 198          moltype = AA  length = 453
FEATURE                 Location/Qualifiers
source                  1..453
                        mol_type = protein
                        organism = synthetic construct
SEQUENCE: 198
EVQLVESGGG LVQPGGSLRL SCAASGFPFS DYSMAWVRQA PGKGLEWVAT IGPSGDTYYR  60
DSVKGRFTIS RDNAKNSLYL QMNSLRAEDT AVYYCASPPQ YYEGSIPRLW PAHWGQGTLV  120
TVSSASTKGP SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK KVEPKSCDKT HTCPPCPAPE  240
```

```
LLGGPSVFLF PPKPKDTLYI TREPEVTCVV VDVSHEDPEV KFNWYVDGVE VHNAKTKPRE  300
EQYNSTYRVV SVLTVLHQDW LNGKEYKCKV SNKALPAPIE KTISKAKGQP REPQVYTLPP  360
SRDELTKNQV SLTCLVKGFY PSDIAVEWES NGQPENNYKT TPPVLDSDGS FFLYSKLTVD  420
KSRWQQGNVF SCSVMHEALH NHYTQKSLSL SPG                              453

SEQ ID NO: 199         moltype = AA  length = 214
FEATURE                Location/Qualifiers
source                 1..214
                       mol_type = protein
                       organism = synthetic construct
SEQUENCE: 199
DIQLTQSPSS LSASVGDRVT ITCRADESVR TLMHWYQQKP GKAPKLLIYL VSNSEIGVPD  60
RFSGSGSGTD FRLTISSLQP EDFATYYCLQ THSYPYTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 200         moltype = AA  length = 453
FEATURE                Location/Qualifiers
source                 1..453
                       mol_type = protein
                       organism = synthetic construct
SEQUENCE: 200
EVQLVESGGG LVQPGGSLRL SCAASGFPFS DYSMAWVRQA PGKGLEWVAT ITGSGSTYYR  60
DSVKGRFTIS RDNAKNSLYL QMNSLRAEDT AVYYCASPPQ YYEGSIVRLW PAHWGQGTLV  120
TVSSASTKGP SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK KVEPKSCDKT HTCPPCPAPE  240
LLGGPSVFLF PPKPKDTLYI TREPEVTCVV VDVSHEDPEV KFNWYVDGVE VHNAKTKPRE  300
EQYNSTYRVV SVLTVLHQDW LNGKEYKCKV SNKALPAPIE KTISKAKGQP REPQVYTLPP  360
SRDELTKNQV SLTCLVKGFY PSDIAVEWES NGQPENNYKT TPPVLDSDGS FFLYSKLTVD  420
KSRWQQGNVF SCSVMHEALH NHYTQKSLSL SPG                              453

SEQ ID NO: 201         moltype = AA  length = 214
FEATURE                Location/Qualifiers
source                 1..214
                       mol_type = protein
                       organism = synthetic construct
SEQUENCE: 201
DIQLTQSPSS LSASVGDRVT ITCRADESVR TLMHWYQQKP GKAPKLLIYL VSNSEIGVPD  60
RFSGSGSGTD FRLTISSLQP EDFATYYCAQ SYSMPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 202         moltype = AA  length = 454
FEATURE                Location/Qualifiers
source                 1..454
                       mol_type = protein
                       organism = synthetic construct
SEQUENCE: 202
EVQLVESGGG LVQPGGSLRL SCAASGFRFS DYYMAWVRQA PGKGLEWVAT ISGSGGTTYY  60
RDSVKGRFTI SRDNAKNSLY LQMNSLRAED TAVYYCASPP QYYEGSIPRL WFAHWGQGTL  120
VTVSSASTKG PSVFPLAPSS KSTSGGTAAL GCLVKDYFPE PVTVSWNSGA LTSGVHTFPA  180
VLQSSGLYSL SSVVTVPSSS LGTQTYICNV NHKPSNTKVD KKVEPKSCDK THTCPPCPAP  240
ELLGGPSVFL FPPKPKDTLY ITREPEVTCV VVDVSHEDPE VKFNWYVDGV EVHNAKTKPR  300
EEQYNSTYRV VSVLTVLHQD WLNGKEYKCK VSNKALPAPI EKTISKAKGQ PREPQVYTLP  360
PSRDELTKNQ VSLTCLVKGF YPSDIAVEWE SNGQPENNYK TTPPVLDSDG SFFLYSKLTV  420
DKSRWQQGNV FSCSVMHEAL HNHYTQKSLS LSPG                              454

SEQ ID NO: 203         moltype = AA  length = 214
FEATURE                Location/Qualifiers
source                 1..214
                       mol_type = protein
                       organism = synthetic construct
SEQUENCE: 203
AIQLTQSPSS LSASVGDRVT ITCRADESVR TLMHWYQQKP GKAPKLLIYL VSNSEIGVPD  60
RFSGSGSGTD FRLTISSLQP EDFATYYCLQ THSYPYTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 204         moltype = AA  length = 454
FEATURE                Location/Qualifiers
source                 1..454
                       mol_type = protein
                       organism = synthetic construct
SEQUENCE: 204
EVQLVESGGG LVQPGGSLRL SCAASGFRFS DYYMAWVRQA PGKGLEWVAT ISGSGGTTYY  60
RDSVKGRFTI SRDNAKNSLY LQMNSLRAED TAVYYCASPP QYYEGSIPRL WFAHWGQGTL  120
VTVSSASTKG PSVFPLAPSS KSTSGGTAAL GCLVKDYFPE PVTVSWNSGA LTSGVHTFPA  180
VLQSSGLYSL SSVVTVPSSS LGTQTYICNV NHKPSNTKVD KKVEPKSCDK THTCPPCPAP  240
ELLGGPSVFL FPPKPKDTLY ITREPEVTCV VVDVSHEDPE VKFNWYVDGV EVHNAKTKPR  300
```

```
EEQYNSTYRV VSVLTVLHQD WLNGKEYKCK VSNKALPAPI EKTISKAKGQ PREPQVYTLP  360
PSRDELTKNQ VSLTCLVKGF YPSDIAVEWE SNGQPENNYK TTPPVLDSDG SFFLYSKLTV  420
DKSRWQQGNV FSCSVMHEAL HNHYTQKSLS LSPG                              454

SEQ ID NO: 205          moltype = AA  length = 214
FEATURE                 Location/Qualifiers
source                  1..214
                        mol_type = protein
                        organism = synthetic construct
SEQUENCE: 205
DIQLTQSPSS LSASVGDRVT ITCRADESVR TLMHWYQQKP GKAPKLLIYL VSNSEIGVPD  60
RFSGSGSGTD FRLTISSLQP EDFATYYCLQ THSYPYTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 206          moltype = AA  length = 453
FEATURE                 Location/Qualifiers
source                  1..453
                        mol_type = protein
                        organism = synthetic construct
SEQUENCE: 206
EVQLVESGGG LVQPGGSLRL SCAASGFTFP SYGMAWVRQA PGKGLEWVAT IDAAGDTYYR  60
DSVKGRFTIS RDNAKNSLYL QMNSLRAEDT AVYYCAAPPQ TYEGSIYRLW FAHWGQGTLV  120
TVSSASTKGP SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK KVEPKSCDKT HTCPPCPAPE  240
LLGGPSVFLF PPKPKDTLYI TREPEVTCVV VDVSHEDPEV KFNWYVDGVE VHNAKTKPRE  300
EQYNSTYRVV SVLTVLHQDW LNGKEYKCKV SNKALPAPIE KTISKAKGQP REPQVYTLPP  360
SRDELTKNQV SLTCLVKGFY PSDIAVEWES NGQPENNYKT TPPVLDSDGS FFLYSKLTVD  420
KSRWQQGNVF SCSVMHEALH NHYTQKSLSL SPG                               453

SEQ ID NO: 207          moltype = AA  length = 214
FEATURE                 Location/Qualifiers
source                  1..214
                        mol_type = protein
                        organism = synthetic construct
SEQUENCE: 207
DIQLTQSPSS LSASVGDRVT ITCRADESVK TLMHWYQQKP GKAPKLLIYL VSNSEIGVPD  60
RFSGSGSGTD FRLTISSLQP EDFATYYCQQ TYSAPHTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 208          moltype = AA  length = 454
FEATURE                 Location/Qualifiers
source                  1..454
                        mol_type = protein
                        organism = synthetic construct
SEQUENCE: 208
EVQLVESGGG LVQPGGSLRL SCAASGFPFS TYAMAWVRQA PGKGLEWVAT IRGSGESTYY  60
RDSVKGRFTI SRDNAKNSLY LQMNSLRAED TAVYYCASPP QYYEGSIDRL WFAHWGQGTL  120
VTVSSASTKG PSVFPLAPSS KSTSGGTAAL GCLVKDYFPE PVTVSWNSGA LTSGVHTFPA  180
VLQSSGLYSL SSVVTVPSSS LGTQTYICNV NHKPSNTKVD KKVEPKSCDK THTCPPCPAP  240
ELLGGPSVFL FPPKPKDTLY ITREPEVTCV VVDVSHEDPE VKFNWYVDGV EVHNAKTKPR  300
EEQYNSTYRV VSVLTVLHQD WLNGKEYKCK VSNKALPAPI EKTISKAKGQ PREPQVYTLP  360
PSRDELTKNQ VSLTCLVKGF YPSDIAVEWE SNGQPENNYK TTPPVLDSDG SFFLYSKLTV  420
DKSRWQQGNV FSCSVMHEAL HNHYTQKSLS LSPG                              454

SEQ ID NO: 209          moltype = AA  length = 214
FEATURE                 Location/Qualifiers
source                  1..214
                        mol_type = protein
                        organism = synthetic construct
SEQUENCE: 209
AIQLTQSPSS LSASVGDRVT ITCRADESVR TLMHWYQQKP GKAPKLLIYL VSNSEIGVPD  60
RFSGSGSGTD FRLTISSLQP EDFATYYCLQ TYSYPFTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 210          moltype =   length =
SEQUENCE: 210
000

SEQ ID NO: 211          moltype =   length =
SEQUENCE: 211
000

SEQ ID NO: 212          moltype =   length =
SEQUENCE: 212
000
```

SEQ ID NO: 213 moltype = length =
SEQUENCE: 213
000

SEQ ID NO: 214 moltype = length =
SEQUENCE: 214
000

SEQ ID NO: 215 moltype = length =
SEQUENCE: 215
000

SEQ ID NO: 216 moltype = length =
SEQUENCE: 216
000

SEQ ID NO: 217 moltype = length =
SEQUENCE: 217
000

SEQ ID NO: 218 moltype = length =
SEQUENCE: 218
000

SEQ ID NO: 219 moltype = length =
SEQUENCE: 219
000

SEQ ID NO: 220 moltype = length =
SEQUENCE: 220
000

SEQ ID NO: 221 moltype = length =
SEQUENCE: 221
000

SEQ ID NO: 222 moltype = length =
SEQUENCE: 222
000

SEQ ID NO: 223 moltype = length =
SEQUENCE: 223
000

SEQ ID NO: 224 moltype = length =
SEQUENCE: 224
000

SEQ ID NO: 225 moltype = length =
SEQUENCE: 225
000

SEQ ID NO: 226 moltype = length =
SEQUENCE: 226
000

SEQ ID NO: 227 moltype = length =
SEQUENCE: 227
000

SEQ ID NO: 228 moltype = length =
SEQUENCE: 228
000

SEQ ID NO: 229 moltype = length =
SEQUENCE: 229
000

SEQ ID NO: 230 moltype = length =
SEQUENCE: 230
000

SEQ ID NO: 231 moltype = length =
SEQUENCE: 231
000

SEQ ID NO: 232 moltype = length =
SEQUENCE: 232
000

SEQ ID NO: 233 moltype = length =
SEQUENCE: 233
000

SEQ ID NO: 234 moltype = length =
SEQUENCE: 234
000

SEQ ID NO: 235 moltype = length =
SEQUENCE: 235
000

SEQ ID NO: 236 moltype = length =
SEQUENCE: 236
000

SEQ ID NO: 237 moltype = length =
SEQUENCE: 237
000

SEQ ID NO: 238 moltype = length =
SEQUENCE: 238
000

SEQ ID NO: 239 moltype = length =
SEQUENCE: 239
000

SEQ ID NO: 240 moltype = length =
SEQUENCE: 240
000

SEQ ID NO: 241 moltype = length =
SEQUENCE: 241
000

SEQ ID NO: 242 moltype = length =
SEQUENCE: 242
000

SEQ ID NO: 243 moltype = length =
SEQUENCE: 243
000

SEQ ID NO: 244 moltype = length =
SEQUENCE: 244
000

SEQ ID NO: 245 moltype = length =
SEQUENCE: 245
000

SEQ ID NO: 246 moltype = length =
SEQUENCE: 246
000

SEQ ID NO: 247 moltype = length =
SEQUENCE: 247
000

SEQ ID NO: 248 moltype = length =
SEQUENCE: 248
000

SEQ ID NO: 249 moltype = length =
SEQUENCE: 249
000

SEQ ID NO: 250 moltype = length =
SEQUENCE: 250
000

SEQ ID NO: 251 moltype = length =
SEQUENCE: 251
000

SEQ ID NO: 252 moltype = length =
SEQUENCE: 252

000

SEQ ID NO: 253 moltype = length =
SEQUENCE: 253
000

SEQ ID NO: 254 moltype = length =
SEQUENCE: 254
000

SEQ ID NO: 255 moltype = length =
SEQUENCE: 255
000

SEQ ID NO: 256 moltype = length =
SEQUENCE: 256
000

SEQ ID NO: 257 moltype = length =
SEQUENCE: 257
000

SEQ ID NO: 258 moltype = length =
SEQUENCE: 258
000

SEQ ID NO: 259 moltype = length =
SEQUENCE: 259
000

SEQ ID NO: 260 moltype = length =
SEQUENCE: 260
000

SEQ ID NO: 261 moltype = length =
SEQUENCE: 261
000

SEQ ID NO: 262 moltype = length =
SEQUENCE: 262
000

SEQ ID NO: 263 moltype = length =
SEQUENCE: 263
000

SEQ ID NO: 264 moltype = length =
SEQUENCE: 264
000

SEQ ID NO: 265 moltype = length =
SEQUENCE: 265
000

SEQ ID NO: 266 moltype = length =
SEQUENCE: 266
000

SEQ ID NO: 267 moltype = length =
SEQUENCE: 267
000

SEQ ID NO: 268 moltype = length =
SEQUENCE: 268
000

SEQ ID NO: 269 moltype = length =
SEQUENCE: 269
000

SEQ ID NO: 270 moltype = length =
SEQUENCE: 270
000

SEQ ID NO: 271 moltype = length =
SEQUENCE: 271
000

SEQ ID NO: 272 moltype = length =

SEQUENCE: 272
000

SEQ ID NO: 273 moltype = length =
SEQUENCE: 273
000

SEQ ID NO: 274 moltype = length =
SEQUENCE: 274
000

SEQ ID NO: 275 moltype = length =
SEQUENCE: 275
000

SEQ ID NO: 276 moltype = length =
SEQUENCE: 276
000

SEQ ID NO: 277 moltype = length =
SEQUENCE: 277
000

SEQ ID NO: 278 moltype = length =
SEQUENCE: 278
000

SEQ ID NO: 279 moltype = length =
SEQUENCE: 279
000

SEQ ID NO: 280 moltype = length =
SEQUENCE: 280
000

SEQ ID NO: 281 moltype = length =
SEQUENCE: 281
000

SEQ ID NO: 282 moltype = length =
SEQUENCE: 282
000

SEQ ID NO: 283 moltype = length =
SEQUENCE: 283
000

SEQ ID NO: 284 moltype = length =
SEQUENCE: 284
000

SEQ ID NO: 285 moltype = length =
SEQUENCE: 285
000

SEQ ID NO: 286 moltype = length =
SEQUENCE: 286
000

SEQ ID NO: 287 moltype = length =
SEQUENCE: 287
000

SEQ ID NO: 288 moltype = length =
SEQUENCE: 288
000

SEQ ID NO: 289 moltype = length =
SEQUENCE: 289
000

SEQ ID NO: 290 moltype = length =
SEQUENCE: 290
000

SEQ ID NO: 291 moltype = length =
SEQUENCE: 291
000

```
SEQ ID NO: 292          moltype =   length =
SEQUENCE: 292
000

SEQ ID NO: 293          moltype =   length =
SEQUENCE: 293
000

SEQ ID NO: 294          moltype =   length =
SEQUENCE: 294
000

SEQ ID NO: 295          moltype =   length =
SEQUENCE: 295
000

SEQ ID NO: 296          moltype =   length =
SEQUENCE: 296
000

SEQ ID NO: 297          moltype =   length =
SEQUENCE: 297
000

SEQ ID NO: 298          moltype =   length =
SEQUENCE: 298
000

SEQ ID NO: 299          moltype =   length =
SEQUENCE: 299
000

SEQ ID NO: 300          moltype = AA  length = 454
FEATURE                 Location/Qualifiers
source                  1..454
                        mol_type = protein
                        organism = synthetic construct
SEQUENCE: 300
EVQLVESGGG LVQPGGSLRL SCAASGFPFS TYAMAWVRQA PGKGLEWVAT IRGSGESTYY  60
RDSVKGRFTI SRDNAKNSLY LQMNSLRAED TAVYYCASPP QYYEGSIDRL WFAHWGQGTL  120
VTVSSASTKG PSVFPLAPSS KSTSGGTAAL GCLVKDYFPE PVTVSWNSGA LTSGVHTFPA  180
VLQSSGLYSL SSVVTVPSSS LGTQTYICNV NHKPSNTKVD KKVEPKSCDK THTCPPCPAP  240
ELLGGPSVFL FPPKPKDTLY ITREPEVTCV VVDVSHEDPE VKFNWYVDGV EVHNAKTKPR  300
EEQYNSTYRV VSVLTVLHQD WLNGKEYKCK VSNKALPAPI EKTISKAKGQ PREPQVYTLP  360
PSRDELTKNQ VSLTCLVKGF YPSDIAVEWE SNGQPENNYK TTPPVLDSDG SFFLYSKLTV  420
DKSRWQQGNV FSCSVMHEAL HNHYTQKSLS LSPG                              454

SEQ ID NO: 301          moltype = AA  length = 214
FEATURE                 Location/Qualifiers
source                  1..214
                        mol_type = protein
                        organism = synthetic construct
SEQUENCE: 301
DIQLTQSPSS LSASVGDRVT ITCRADESVR TLMHWYQQKP GKAPKLLIYL VSNSEIGVPD  60
RFSGSGSGTD FRLTISSLQP EDFATYYCLQ TYSYPFTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 302          moltype = AA  length = 454
FEATURE                 Location/Qualifiers
source                  1..454
                        mol_type = protein
                        organism = synthetic construct
SEQUENCE: 302
EVQLVESGGG LVQPGGSLRL SCAASGFTFS DYNMAWVRQA PGKGLEWVAT ITYEGRNTYY  60
RDSVKGRFTI SRDNAKNSLY LQMNSLRAED TAVYYCASPP QYYEGSIYRL WFAHWGQGTL  120
VTVSSASTKG PSVFPLAPSS KSTSGGTAAL GCLVKDYFPE PVTVSWNSGA LTSGVHTFPA  180
VLQSSGLYSL SSVVTVPSSS LGTQTYICNV NHKPSNTKVD KKVEPKSCDK THTCPPCPAP  240
ELLGGPSVFL FPPKPKDTLY ITREPEVTCV VVDVSHEDPE VKFNWYVDGV EVHNAKTKPR  300
EEQYNSTYRV VSVLTVLHQD WLNGKEYKCK VSNKALPAPI EKTISKAKGQ PREPQVYTLP  360
PSRDELTKNQ VSLTCLVKGF YPSDIAVEWE SNGQPENNYK TTPPVLDSDG SFFLYSKLTV  420
DKSRWQQGNV FSCSVMHEAL HNHYTQKSLS LSPG                              454

SEQ ID NO: 303          moltype = AA  length = 214
FEATURE                 Location/Qualifiers
source                  1..214
                        mol_type = protein
                        organism = synthetic construct
SEQUENCE: 303
```

```
DIQLTQSPSS LSASVGDRVT ITCRADESVR TLMHWYQQKP GKAPKLLIYL VSNSEIGVPD  60
RFSGSGSGTD FRLTISSLQP EDFATYYCQQ TWSDPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 304         moltype = AA  length = 454
FEATURE                Location/Qualifiers
source                 1..454
                       mol_type = protein
                       organism = synthetic construct
SEQUENCE: 304
EVQLVESGGG LVQPGGSLRL SCAASGFTFS DYNMAWVRQA PGKGLEWVAT ITYEGRNTYY  60
RDSVKGRFTI SRDNAKNSLY LQMNSLRAED TAVYYCASPP QYYEGSIYRL WFAHWGQGTL  120
VTVSSASTKG PSVFPLAPSS KSTSGGTAAL GCLVKDYFPE PVTVSWNSGA LTSGVHTFPA  180
VLQSSGLYSL SSVVTVPSSS LGTQTYICNV NHKPSNTKVD KKVEPKSCDK THTCPPCPAP  240
ELLGGPSVFL FPPKPKDTLY ITREPEVTCV VVDVSHEDPE VKFNWYVDGV EVHNAKTKPR  300
EEQYNSTYRV VSVLTVLHQD WLNGKEYKCK VSNKALPAPI EKTISKAKGQ PREPQVYTLP  360
PSRDELTKNQ VSLTCLVKGF YPSDIAVEWE SNGQPENNYK TTPPVLDSDG SFFLYSKLTV  420
DKSRWQQGNV FSCSVMHEAL HNHYTQKSLS LSPG                              454

SEQ ID NO: 305         moltype = AA  length = 214
FEATURE                Location/Qualifiers
source                 1..214
                       mol_type = protein
                       organism = synthetic construct
SEQUENCE: 305
DIQMTQSPSS LSASVGDRVT ITCRADESVR TLMHWYQQKP GKAPKLLIYL VSNSEIGVPD  60
RFSGSGSGTD FRLTISSLQP EDFATYYCQQ TWSDPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 306         moltype = AA  length = 454
FEATURE                Location/Qualifiers
source                 1..454
                       mol_type = protein
                       organism = synthetic construct
SEQUENCE: 306
EVQLVESGGG LVQPGGSLRL SCAASGFPFS DYSMAWVRQA PGKGLEWVAT IGPSGDTYYR  60
DSVKGRFTIS RDNAKNSLYL QMNSLRAEDT AVYYCASPPQ YYEGSIPRLW PAHWGQGTLV  120
TVSSASTKGP SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK KVEPKSCDKT HTCPPCPAPE  240
LLGGPSVFLF PPKPKDTLYI TREPEVTCVV VDVSHEDPEV KFNWYVDGVE VHNAKTKPRE  300
EQYNSTYRVV SVLTVLHQDW LNGKEYKCKV SNKALPAPIE KTISKAKGQP REPQVYTLPP  360
SRDELTKNQV SLTCLVKGFY PSDIAVEWES NGQPENNYKT TPPVLDSDGS FFLYSKLTVD  420
KSRWQQGNVF SCSVMHEALH NHYTQKSLSL SPGK                              454

SEQ ID NO: 307         moltype = AA  length = 454
FEATURE                Location/Qualifiers
source                 1..454
                       mol_type = protein
                       organism = synthetic construct
SEQUENCE: 307
EVQLVESGGG LVQPGGSLRL SCAASGFPFS DYSMAWVRQA PGKGLEWVAT ITGSGSTYYR  60
DSVKGRFTIS RDNAKNSLYL QMNSLRAEDT AVYYCASPPQ YYEGSIVRLW PAHWGQGTLV  120
TVSSASTKGP SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK KVEPKSCDKT HTCPPCPAPE  240
LLGGPSVFLF PPKPKDTLYI TREPEVTCVV VDVSHEDPEV KFNWYVDGVE VHNAKTKPRE  300
EQYNSTYRVV SVLTVLHQDW LNGKEYKCKV SNKALPAPIE KTISKAKGQP REPQVYTLPP  360
SRDELTKNQV SLTCLVKGFY PSDIAVEWES NGQPENNYKT TPPVLDSDGS FFLYSKLTVD  420
KSRWQQGNVF SCSVMHEALH NHYTQKSLSL SPGK                              454

SEQ ID NO: 308         moltype = AA  length = 455
FEATURE                Location/Qualifiers
source                 1..455
                       mol_type = protein
                       organism = synthetic construct
SEQUENCE: 308
EVQLVESGGG LVQPGGSLRL SCAASGFRFS DYYMAWVRQA PGKGLEWVAT ISGSGGTTYY  60
RDSVKGRFTI SRDNAKNSLY LQMNSLRAED TAVYYCASPP QYYEGSIPRL WFAHWGQGTL  120
VTVSSASTKG PSVFPLAPSS KSTSGGTAAL GCLVKDYFPE PVTVSWNSGA LTSGVHTFPA  180
VLQSSGLYSL SSVVTVPSSS LGTQTYICNV NHKPSNTKVD KKVEPKSCDK THTCPPCPAP  240
ELLGGPSVFL FPPKPKDTLY ITREPEVTCV VVDVSHEDPE VKFNWYVDGV EVHNAKTKPR  300
EEQYNSTYRV VSVLTVLHQD WLNGKEYKCK VSNKALPAPI EKTISKAKGQ PREPQVYTLP  360
PSRDELTKNQ VSLTCLVKGF YPSDIAVEWE SNGQPENNYK TTPPVLDSDG SFFLYSKLTV  420
DKSRWQQGNV FSCSVMHEAL HNHYTQKSLS LSPGK                             455

SEQ ID NO: 309         moltype = AA  length = 454
FEATURE                Location/Qualifiers
source                 1..454
```

```
                        mol_type = protein
                        organism = synthetic construct
SEQUENCE: 309
EVQLVESGGG LVQPGGSLRL SCAASGFTFP SYGMAWVRQA PGKGLEWVAT IDAAGDTYYR  60
DSVKGRFTIS RDNAKNSLYL QMNSLRAEDT AVYYCAAPPQ TYEGSIYRLW FAHWGQGTLV  120
TVSSASTKGP SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK KVEPKSCDKT HTCPPCPAPE  240
LLGGPSVFLF PPKPKDTLYI TREPEVTCVV VDVSHEDPEV KFNWYVDGVE VHNAKTKPRE  300
EQYNSTYRVV SVLTVLHQDW LNGKEYKCKV SNKALPAPIE KTISKAKGQP REPQVYTLPP  360
SRDELTKNQV SLTCLVKGFY PSDIAVEWES NGQPENNYKT TPPVLDSDGS FFLYSKLTVD  420
KSRWQQGNVF SCSVMHEALH NHYTQKSLSL SPGK                            454

SEQ ID NO: 310          moltype = AA  length = 455
FEATURE                 Location/Qualifiers
source                  1..455
                        mol_type = protein
                        organism = synthetic construct
SEQUENCE: 310
EVQLVESGGG LVQPGGSLRL SCAASGFPFS TYAMAWVRQA PGKGLEWVAT IRGSGESTYY  60
RDSVKGRFTI SRDNAKNSLY LQMNSLRAED TAVYYCASPP QYYEGSIDRL WFAHWGQGTL  120
VTVSSASTKG PSVFPLAPSS KSTSGGTAAL GCLVKDYFPE PVTVSWNSGA LTSGVHTFPA  180
VLQSSGLYSL SSVVTVPSSS LGTQTYICNV NHKPSNTKVD KKVEPKSCDK THTCPPCPAP  240
ELLGGPSVFL FPPKPKDTLY ITREPEVTCV VVDVSHEDPE VKFNWYVDGV EVHNAKTKPR  300
EEQYNSTYRV VSVLTVLHQD WLNGKEYKCK VSNKALPAPI EKTISKAKGQ PREPQVYTLP  360
PSRDELTKNQ VSLTCLVKGF YPSDIAVEWE SNGQPENNYK TTPPVLDSDG SFFLYSKLTV  420
DKSRWQQGNV FSCSVMHEAL HNHYTQKSLS LSPGK                           455

SEQ ID NO: 311          moltype = AA  length = 455
FEATURE                 Location/Qualifiers
source                  1..455
                        mol_type = protein
                        organism = synthetic construct
SEQUENCE: 311
EVQLVESGGG LVQPGGSLRL SCAASGFTFS DYNMAWVRQA PGKGLEWVAT ITYEGRNTYY  60
RDSVKGRFTI SRDNAKNSLY LQMNSLRAED TAVYYCASPP QYYEGSIYRL WFAHWGQGTL  120
VTVSSASTKG PSVFPLAPSS KSTSGGTAAL GCLVKDYFPE PVTVSWNSGA LTSGVHTFPA  180
VLQSSGLYSL SSVVTVPSSS LGTQTYICNV NHKPSNTKVD KKVEPKSCDK THTCPPCPAP  240
ELLGGPSVFL FPPKPKDTLY ITREPEVTCV VVDVSHEDPE VKFNWYVDGV EVHNAKTKPR  300
EEQYNSTYRV VSVLTVLHQD WLNGKEYKCK VSNKALPAPI EKTISKAKGQ PREPQVYTLP  360
PSRDELTKNQ VSLTCLVKGF YPSDIAVEWE SNGQPENNYK TTPPVLDSDG SFFLYSKLTV  420
DKSRWQQGNV FSCSVMHEAL HNHYTQKSLS LSPGK                           455
```

IL-17 BINDING PROTEINS, COMPOSITIONS, AND METHODS OF USE THEREOF

CROSS REFERENCE TO RELATED APPLICATIONS

This application is a Continuation of U.S. patent application Ser. No. 19/324,344 (filed Sep. 10, 2025), which application claims the benefit of and priority to U.S. Provisional Application No. 63/693,684 (filed Sep. 11, 2024) and U.S. Provisional Application No. 63/767,149 (filed Mar. 5, 2025), the entire disclosures of which are hereby incorporated by reference in their entirety for all purposes.

TECHNICAL FIELD

The present invention relates to IL-17-binding proteins, and related nucleic acids, expression vectors, host cells, pharmaceutical compositions, methods of making, and methods of use.

SEQUENCE LISTING

The instant application contains a Sequence Listing which has been submitted electronically in XML file format and is hereby incorporated by reference in its entirety. Said XML copy, created on Aug. 15, 2025, is named ORJ-074CN_Sequence-Listing.xml and is 257,193 bytes in size.

BACKGROUND

IL-17 cytokine family members (e.g., IL-17A and IL-17F) have diverse biological functions, promoting protective immunity against many pathogens but also driving inflammatory pathology during infection and autoimmunity. However, IL-17A and IL-17F are also associated or suspected to be associated with the pathogenesis of inflammatory diseases such as psoriasis, psoriatic arthritis (PsA), and hidradenitis suppurativa (HS).

Psoriasis is a chronic relapsing skin disorder which causes a rash with itchy, scaly patches, most commonly on the knees, elbows, trunk and scalp. Plaque psoriasis, the most common type of psoriasis, causes dry, itchy, raised skin patches (plaques) covered with scales. Plaques usually appear on the elbows, knees, lower back and scalp.

PsA refers to chronic inflammatory arthritis associated with psoriasis. About 1 in 20 individuals with psoriasis will develop arthritis along with psoriasis, and in about 75% of cases, psoriasis precedes the arthritis. PsA exhibits itself in a variety of ways, ranging from mild to severe arthritis, wherein the arthritis usually affects the fingers and the spine.

HS is a painful, chronic skin condition which causes skin abscesses and scarring on the skin. Pea- to marble-sized lumps form under the skin. These lumps can be painful and usually occur where skin rubs together, such as in the armpits, groin, and buttocks.

A need remains for improved therapeutics for autoimmune or inflammatory conditions such as psoriasis, PsA, and HS.

SUMMARY

The present invention addresses this need with IL-17 binding proteins, as well as related compositions and methods. In some embodiments, provided binding proteins and compositions exhibit improved therapeutic efficacy and/or half-lives relative to existing IL-17-targeting therapeutics.

In one aspect, provided are IL-17-binding proteins comprising a heavy chain variable domain ($V_H$) comprising complementarity-determining regions: (a) CDR-H1 comprising the amino acid sequence of SEQ ID NO: 1; CDR-H2 comprising the amino acid sequence of SEQ ID NO: 2; and CDR-H3 comprising the amino acid sequence of SEQ ID NO: 3; (b) CDR-H1 comprising the amino acid sequence of SEQ ID NO: 7; CDR-H2 comprising the amino acid sequence of SEQ ID NO: 8; and CDR-H3 comprising the amino acid sequence of SEQ ID NO: 9; or (c) CDR-H1 comprising the amino acid sequence of SEQ ID NO: 11; CDR-H2 comprising the amino acid sequence of SEQ ID NO: 12; and CDR-H3 comprising the amino acid sequence of SEQ ID NO: 13. In some embodiments, the $V_H$ comprises an amino acid sequence that is at least 85%, at least 90%, at least 95%, at least 96%, at least 97%, at least 98%, or at least 99% identical to that of SEQ ID NO: 16.

In some embodiments, provided IL-17 binding proteins further comprise a light chain variable domain ($V_L$) comprising complementarity-determining regions: (a) CDR-L1 comprising the amino acid sequence of SEQ ID NO: 4; CDR-L2 comprising the amino acid sequence of SEQ ID NO: 5; and CDR-L3 comprising the amino acid sequence of SEQ ID NO: 6; (b) CDR-L1 comprising the amino acid sequence of SEQ ID NO: 10; CDR-L2 comprising the amino acid sequence LVS; and CDR-L3 comprising the amino acid sequence of SEQ ID NO: 6; or (c) CDR-L1 comprising the amino acid sequence of SEQ ID NO: 14; CDR-L2 comprising the amino acid sequence LVS; and CDR-L3 comprising the amino acid sequence of SEQ ID NO: 15. In some embodiments, the $V_L$ comprises an amino acid sequence that is at least 85%, at least 90%, at least 95%, at least 96%, at least 97%, at least 98%, or at least 99% identical to that of SEQ ID NO: 17 or 18.

In some embodiments, provided are IL-17-binding proteins comprising a heavy chain variable domain ($V_H$) having the amino acid sequence of SEQ ID NO: 16 and a light chain variable domain (VL) having the amino acid sequence of SEQ ID NO: 17 or 18. In some embodiments, the IL-17-binding proteins comprise an Fc region comprising the M252Y/S254T/T256E (YTE) mutations. In some embodiments, the IL-17-binding proteins comprise a modified Fc region having the amino acid sequence of SEQ ID NO: 95.

In one aspect, provided are IL-17-binding proteins comprising a heavy chain variable domain ($V_H$) comprising complementarity-determining regions: (a) CDR-H1 comprising the amino acid sequence of SEQ ID NO: 1; CDR-H2 comprising the amino acid sequence of SEQ ID NO: 19; and CDR-H3 comprising the amino acid sequence of SEQ ID NO: 20; (b) CDR-H1 comprising the amino acid sequence of SEQ ID NO: 7; CDR-H2 comprising the amino acid sequence of SEQ ID NO: 22; and CDR-H3 comprising the amino acid sequence of SEQ ID NO: 23; or (c) CDR-H1 comprising the amino acid sequence of SEQ ID NO: 11; CDR-H2 comprising the amino acid sequence of SEQ ID NO: 24; and CDR-H3 comprising the amino acid sequence of SEQ ID NO: 25. In some embodiments, the $V_H$ comprises an amino acid sequence that is at least 85%, at least 90%, at least 95%, at least 96%, at least 97%, at least 98%, or at least 99% identical to that of SEQ ID NO: 27.

In some embodiments, provided IL-17-binding proteins of further comprise a light chain variable domain ($V_L$) comprising complementarity-determining regions: (a) CDR-L1 comprising the amino acid sequence of SEQ ID NO: 4; CDR-L2 comprising the amino acid sequence of SEQ ID NO: 5; and CDR-L3 comprising the amino acid sequence of SEQ ID NO: 21; (b) CDR-L1 comprising the amino acid sequence of SEQ ID NO: 10; CDR-L2 comprising the amino acid sequence LVS; and CDR-L3 comprising the amino acid sequence of SEQ ID NO: 21; or (c) CDR-L1 comprising the amino acid sequence of SEQ ID NO: 14; CDR-L2 comprising the amino acid sequence LVS; and CDR-L3 comprising the amino acid sequence of SEQ ID NO: 26. In some embodiments, the $V_L$ comprises an amino acid sequence that is at least 85%, at least 90%, at least 95%, at least 96%, at least 97%, at least 98%, or at least 99% identical to that of SEQ ID NO: 28.

In some embodiments, provided are IL-17-binding proteins comprising a heavy chain variable domain ($V_H$) having the amino acid sequence of SEQ ID NO: 27 and a light chain variable domain (VL) having the amino acid sequence of SEQ ID NO: 28. In some embodiments, the IL-17-binding proteins comprise an Fc region comprising the M252Y/S254T/T256E (YTE) mutations. In some embodiments, the IL-17-binding proteins comprise a modified Fc region having the amino acid sequence of SEQ ID NO: 95.

In one aspect, provided are IL-17-binding proteins comprising a heavy chain variable domain ($V_H$) comprising complementarity-determining regions: (a) CDR-H1 comprising the amino acid sequence of SEQ ID NO: 29; CDR-H2 comprising the amino acid sequence of SEQ ID NO: 30; and CDR-H3 comprising the amino acid sequence of SEQ ID NO: 31; (b) CDR-H1 comprising the amino acid sequence of SEQ ID NO: 32; CDR-H2 comprising the amino acid sequence of SEQ ID NO: 33; and CDR-H3 comprising the amino acid sequence of SEQ ID NO: 34; or (c) CDR-H1 comprising the amino acid sequence of SEQ ID NO: 35; CDR-H2 comprising the amino acid sequence of SEQ ID NO: 36; and CDR-H3 comprising the amino acid sequence of SEQ ID NO: 37. In some embodiments, the $V_H$ comprises an amino acid sequence that is at least 85%, at least 90%, at least 95%, at least 96%, at least 97%, at least 98%, or at least 99% identical to that of SEQ ID NO: 38.

In some embodiments, provided IL-17-binding proteins further comprise a light chain variable domain ($V_L$) comprising complementarity-determining regions: (a) CDR-L1 comprising the amino acid sequence of SEQ ID NO: 4; CDR-L2 comprising the amino acid sequence of SEQ ID NO: 5; and CDR-L3 comprising the amino acid sequence of SEQ ID NO: 6; (b) CDR-L1 comprising the amino acid sequence of SEQ ID NO: 10; CDR-L2 comprising the amino acid sequence LVS; and CDR-L3 comprising the amino acid sequence of SEQ ID NO: 6; or (c) CDR-L1 comprising the amino acid sequence of SEQ ID NO: 14; CDR-L2 comprising the amino acid sequence LVS; and CDR-L3 comprising the amino acid sequence of SEQ ID NO: 15. In some embodiments, the $V_L$ comprises an amino acid sequence that is at least 85%, at least 90%, at least 95%, at least 96%, at least 97%, at least 98%, or at least 99% identical to that of SEQ ID NO: 17 or 18.

In some embodiments, provided are IL-17-binding proteins comprising a heavy chain variable domain ($V_H$) having the amino acid sequence of SEQ ID NO: 38 and a light chain variable domain (VL) having the amino acid sequence of SEQ ID NO: 17 or 18. In some embodiments, the IL-17-binding proteins comprise an Fc region comprising the M252Y/S254T/T256E (YTE) mutations. In some embodiments, the IL-17-binding proteins comprise a modified Fc region having the amino acid sequence of SEQ ID NO: 95.

In one aspect, provided are IL-17-binding proteins comprising a heavy chain variable domain ($V_H$) comprising complementarity-determining regions: (a) CDR-H1 comprising the amino acid sequence of SEQ ID NO: 39; CDR-H2 comprising the amino acid sequence of SEQ ID NO: 40; and CDR-H3 comprising the amino acid sequence of SEQ ID NO: 41; (b) CDR-H1 comprising the amino acid sequence of SEQ ID NO: 44; CDR-H2 comprising the amino acid sequence of SEQ ID NO: 45; and CDR-H3 comprising the amino acid sequence of SEQ ID NO: 46; or (c) CDR-H1 comprising the amino acid sequence of SEQ ID NO: 48; CDR-H2 comprising the amino acid sequence of SEQ ID NO: 49; and CDR-H3 comprising the amino acid sequence of SEQ ID NO: 50. In some embodiments, the $V_H$ comprises an amino acid sequence that is at least 85%, at least 90%, at least 95%, at least 96%, at least 97%, at least 98%, or at least 99% identical to that of SEQ ID NO: 53.

In some embodiments, provided IL-17-binding proteins further comprise a light chain variable domain ($V_L$) comprising complementarity-determining regions: (a) CDR-L1 comprising the amino acid sequence of SEQ ID NO: 42; CDR-L2 comprising the amino acid sequence of SEQ ID NO: 5; and CDR-L3 comprising the amino acid sequence of SEQ ID NO: 43; (b) CDR-L1 comprising the amino acid sequence of SEQ ID NO: 47; CDR-L2 comprising the amino acid sequence LVS; and CDR-L3 comprising the amino acid sequence of SEQ ID NO: 43; or (c) CDR-L1 comprising the amino acid sequence of SEQ ID NO: 51; CDR-L2 comprising the amino acid sequence LVS; and CDR-L3 comprising the amino acid sequence of SEQ ID NO: 52. In some embodiments, the $V_L$ comprises an amino acid sequence that is at least 85%, at least 90%, at least 95%, at least 96%, at least 97%, at least 98%, or at least 99% identical to that of SEQ ID NO: 54.

In some embodiments, provided are IL-17-binding proteins comprising a heavy chain variable domain ($V_H$) having the amino acid sequence of SEQ ID NO: 53 and a light chain variable domain (VL) having the amino acid sequence of SEQ ID NO: 54. In some embodiments, the IL-17-binding proteins comprise an Fc region comprising the M252Y/S254T/T256E (YTE) mutations. In some embodiments, the IL-17-binding proteins comprise a modified Fc region having the amino acid sequence of SEQ ID NO: 95.

In one aspect, provided are IL-17-binding proteins comprising a heavy chain variable domain ($V_H$) comprising complementarity-determining regions: (a) CDR-H1 comprising the amino acid sequence of SEQ ID NO: 55; CDR-H2 comprising the amino acid sequence of SEQ ID NO: 56; and CDR-H3 comprising the amino acid sequence of SEQ ID NO: 57; (b) CDR-H1 comprising the amino acid sequence of SEQ ID NO: 59; CDR-H2 comprising the amino acid sequence of SEQ ID NO: 60; and CDR-H3 comprising the amino acid sequence of SEQ ID NO: 61; or (c) CDR-H1 comprising the amino acid sequence of SEQ ID NO: 62; CDR-H2 comprising the amino acid sequence of SEQ ID NO: 63; and CDR-H3 comprising the amino acid sequence of SEQ ID NO: 64. In some embodiments, the $V_H$ comprises an amino acid sequence that is at least 85%, at least 90%, at least 95%, at least 96%, at least 97%, at least 98%, or at least 99% identical to that of SEQ ID NO: 66.

In some embodiments, provided IL-17-binding proteins further comprise a light chain variable domain ($V_L$) comprising complementarity-determining regions: (a) CDR-L1 comprising the amino acid sequence of SEQ ID NO: 4; CDR-L2 comprising the amino acid sequence of SEQ ID NO: 5; and CDR-L3 comprising the amino acid sequence of SEQ ID NO: 58; (b) CDR-L1 comprising the amino acid sequence of SEQ ID NO: 10; CDR-L2 comprising the amino acid sequence LVS; and CDR-L3 comprising the amino acid sequence of SEQ ID NO: 58; or (c) CDR-L1 comprising the amino acid sequence of SEQ ID NO: 14; CDR-L2 comprising the amino acid sequence LVS; and CDR-L3 comprising the amino acid sequence of SEQ ID NO: 65. In some embodiments, the $V_L$ comprises an amino acid sequence that is at least 85%, at least 90%, at least 95%, at least 96%, at least 97%, at least 98%, or at least 99% identical to that of SEQ ID NO: 67 or 68.

In some embodiments, IL-17-binding protein comprising a heavy chain variable domain ($V_H$) having the amino acid sequence of SEQ ID NO: 66 and a light chain variable domain (VL) having the amino acid sequence of SEQ ID NO: 67 or 68. In some embodiments, the IL-17-binding proteins comprise an Fc region comprising the M252Y/S254T/T256E (YTE) mutations. In some embodiments, the IL-17-binding proteins comprise a modified Fc region having the amino acid sequence of SEQ ID NO: 95.

In one aspect, provided are IL-17-binding proteins comprising (a) a heavy chain variable domain ($V_H$) having an amino acid sequence that is at least 85%, at least 90%, at least 95%, at least 96%, at least 97%, at least 98%, or at least 99% identical to that of SEQ ID NO: 80 and comprising complementarity-determining regions: (i) CDR-H1 comprising the amino acid sequence of SEQ ID NO: 69; CDR-H2 comprising the amino acid sequence of SEQ ID NO: 70; and CDR-H3 comprising the amino acid sequence of SEQ ID NO: 71; (ii) CDR-H1 comprising the amino acid sequence of SEQ ID NO: 73; CDR-H2 comprising the amino acid sequence of SEQ ID NO: 74; and CDR-H3 comprising the amino acid sequence of SEQ ID NO: 75; or (iii) CDR-H1 comprising the amino acid sequence of SEQ ID NO: 76; CDR-H2 comprising the amino acid sequence of SEQ ID NO: 77; and CDR-H3 comprising the amino acid sequence of SEQ ID NO: 78; and (b) a light chain variable domain ($V_L$) comprising a light chain variable domain ($V_L$) (1) having an amino acid sequence that is at least 85%, at least 90%, at least 95%, at least 96%, at least 97%, at least 98%, or at least 99% identical to that of SEQ ID NO: 81 or 82; (2) comprising complementarity-determining regions: (i) CDR-L1 comprising the amino acid sequence of SEQ ID NO: 4; CDR-L2 comprising the amino acid sequence of SEQ ID NO: 5; and CDR-L3 comprising the amino acid sequence of SEQ ID NO: 72; (ii) CDR-L1 comprising the amino acid sequence of SEQ ID NO: 10; CDR-L2 comprising the amino acid sequence LVS; and CDR-L3 comprising the amino acid sequence of SEQ ID NO: 72; or (iii) CDR-L1 comprising the amino acid sequence of SEQ ID NO: 14; CDR-L2 comprising the amino acid sequence LVS; and CDR-L3 comprising the amino acid sequence of SEQ ID NO: 79; and (3) an aspartate or aspartic acid residue at a position corresponding to position 1 of SEQ ID NO: 81 or 82; and (4) optionally a methionine residue at a position corresponding to position 4 of SEQ ID NO: 81 or 82. In some embodiments, the $V_H$ comprises an amino acid sequence of SEQ ID NO: 80. In some embodiments, the $V_H$ comprises an amino acid sequence of SEQ ID NO: 81 or 82.

In some embodiments, provided are IL-17-binding proteins comprising a heavy chain variable domain ($V_H$) having the amino acid sequence of SEQ ID NO: 80 and a light chain variable domain (VL) having the amino acid sequence of SEQ ID NO: 81 or 82. In some embodiments, the IL-17-binding proteins comprise an Fc region comprising the M252Y/S254T/T256E (YTE) mutations. In some embodiments, the IL-17-binding proteins comprise a modified Fc region having the amino acid sequence of SEQ ID NO: 95.

In some embodiments, provided are IL-17-binding proteins comprising a heavy chain having the amino acid sequence of SEQ ID NO: 196 or 306 and a light chain having the amino acid sequence of SEQ ID NO: 197.

In some embodiments, provided are IL-17-binding proteins comprising a heavy chain having the amino acid sequence of SEQ ID NO: 198 or 306 and a light chain having the amino acid sequence of SEQ ID NO: 199.

In some embodiments, provided are IL-17-binding proteins comprising a heavy chain having the amino acid sequence of SEQ ID NO: 200 or 307 and a light chain having the amino acid sequence of SEQ ID NO: 201.

In some embodiments, provided are IL-17-binding proteins comprising a heavy chain having the amino acid sequence of SEQ ID NO: 202 or 308 and a light chain having the amino acid sequence of SEQ ID NO: 203.

In some embodiments, provided are IL-17-binding proteins comprising a heavy chain having the amino acid sequence of SEQ ID NO: 204 or 308 and a light chain having the amino acid sequence of SEQ ID NO: 205.

In some embodiments, provided are IL-17-binding proteins comprising a heavy chain having the amino acid sequence of SEQ ID NO: 206 or 309 and a light chain having the amino acid sequence of SEQ ID NO: 207.

In some embodiments, provided are IL-17-binding proteins comprising a heavy chain having the amino acid sequence of SEQ ID NO: 208 or 310 and a light chain having the amino acid sequence of SEQ ID NO: 209.

In some embodiments, provided are IL-17-binding proteins comprising a heavy chain having the amino acid sequence of SEQ ID NO: 300 or 310 and a light chain having the amino acid sequence of SEQ ID NO: 301.

In some embodiments, provided are IL-17-binding proteins comprising a heavy chain having the amino acid sequence of SEQ ID NO: 302 or 311 and a light chain having the amino acid sequence of SEQ ID NO: 303.

In some embodiments, provided are IL-17-binding proteins comprising a heavy chain having the amino acid sequence of SEQ ID NO: 304 or 311 and a light chain having the amino acid sequence of SEQ ID NO: 305.

In some embodiments, an IL-17 binding protein as provided herein is capable of binding to both IL-17A and IL-17F.

In some embodiments, the IL-17 binding protein is an antibody or antigen-binding fragment thereof, e.g., a human antibody or antigen-binding fragment thereof. In some embodiments, the antigen-binding fragment is a Fab, a F(ab')2, a Fab', a single-chain Fv (scFv), an Fv fragment, a Fd fragment, or a diabody.

In some embodiments, the antibody or antigen binding fragment thereof comprises an Fc region, e.g., an IgG1, IgG2, or IgG4 Fc region.

In some embodiments, the Fc region is a modified Fc region, for example, a modified Fc region comprises a half-life extending mutation or set of mutations, for example, a set of half-life extending mutations selected from the group consisting of M252Y/S254T/T256E (YTE), M428L/N434S (LS), M428L/N434A (LA), H433K/N434F (KF), and L309D/Q311H/N434S (DHS).

In some embodiments, the IL-17-binding proteins disclosed herein comprise an Fc region comprising the M252Y/S254T/T256E (YTE) mutations. In some embodiments, the IL-17-binding proteins disclosed herein comprise a modified Fc region having the amino acid sequence of SEQ ID NO: 95.

In some embodiments, the antibody or antigen binding fragment thereof has a half-life of at least about 25 days (e.g., 25 days, 26 days, 27 days, 28 days, 29 days, 30 days, 31 days, 32 days, or 33 days). In one embodiment, the antibody or antigen binding fragment thereof has a half-life of about 30 days. In one embodiment, the antibody or antigen binding fragment thereof has a half-life of about 31 days. In one embodiment, the antibody or antigen binding fragment thereof has a half-life of about 32 days.

In one aspect, provided are isolated nucleic acids encoding an IL-17-binding protein as disclosed herein.

In one aspect, provided are expression vector comprising isolated nucleic acids as disclosed herein.

In one aspect, provided are host cells comprising isolated nucleic acid molecules or expression vectors as disclosed herein.

In one aspect, provided are methods of producing the anti-IL17-binding proteins disclosed herein, comprising the step of culturing the host cells disclosed herein under suitable conditions to produce the IL-17-binding proteins.

In one aspect, provided are methods of producing IL-17-binding proteins comprising the steps of introducing to host cells the isolated nucleic acids disclosed herein, or the expression vectors disclosed herein, and culturing the host cells under suitable conditions to produce the IL-17-binding proteins.

In one aspect, provided are methods of detecting IL-17A, IL-17F, or IL-17A and IL-17F in a sample, comprising the steps of contacting the sample with the IL-17-binding proteins described herein, optionally conjugated with a detection label, and detecting the presence and/or quantity of IL-17A, IL-17F, or IL-17A and IL-17F in the sample.

In one aspect, provided are pharmaceutical compositions comprising an IL-17-binding protein as provided herein and a pharmaceutically acceptable carrier.

In one aspect, provided are methods comprising a step of administering to a subject in need thereof an effective amount of an IL-17-binding protein or a pharmaceutical composition as disclosed herein.

In some embodiments, the subject has an autoimmune or inflammatory condition, for example, the subject may have a disorder selected from the group consisting of psoriasis, psoriatic arthritis, axial spondyloarthritis, palmoplantar pustulosis, non-infectious uveitis, polymyalgia rheumatica, giant cell arteritis, juvenile idiopathic arthritis, dissecting cellulitis of the scalp, Behcet's disease, Netherton syndrome, *pityriasis rubra* pilaris, SAPHO (synovitis, acne, pustulosis, hyperostosis and osteitis) syndrome, and hidradenitis suppurativa.

In some embodiments, the subject has an inflammatory bowel disease, for example, ulcerative colitis or Crohn's disease.

In one aspect, provided are methods of treating an autoimmune or inflammatory condition in a subject comprising a step of administering to the subject a maintenance dose of an IL-17A/F binding protein or a pharmaceutical composition as disclosed herein, for example, every 16 weeks, every four months, three times a year, every 26 weeks, or every six months, or twice a year for a period of time sufficient to treat or ameliorate the autoimmune or inflammatory condition.

In some embodiments, the step of administering comprises systemic administration of the IL-17-binding protein, for example, by systemic administration comprising intravenous or subcutaneous administration.

In some embodiments, the subject is a primate, such as a human.

DETAILED DESCRIPTION OF CERTAIN EMBODIMENTS

Figure 1A:
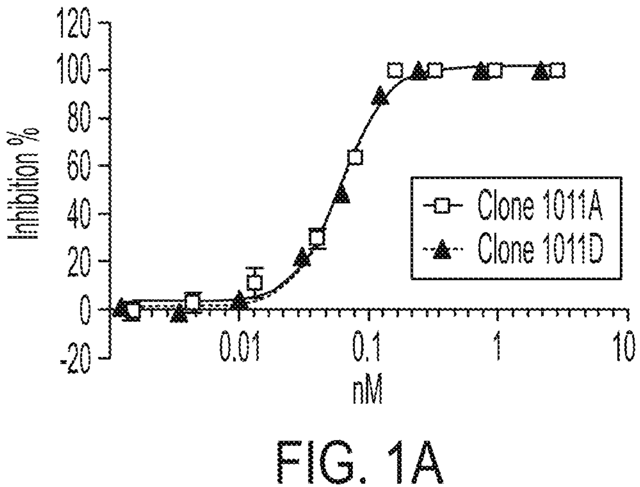
FIGS. 1A-1F are graphs showing percent inhibition of IL-17A induced activation of NFκB in a reporter cell line. Specifically, FIG. 1A (Clone 1011A and Clone 1011D), FIG. 1B (Clone 1161A and Clone 1116D), FIG. 1C (Clone 1182A and Clone 1182D), FIG. 1D (Clone 1114D), FIG. 1E (Clone 1181D), and FIG. 1F (IL-17 A/F Reference Ab) show percent inhibition of IL-17A induced activation of NFκB.

In various embodiments, provided are IL-17 binding proteins, nucleic acids encoding the same, compositions thereof, methods of producing thereof, and methods of use thereof.

Definitions

To facilitate an understanding of the present disclosure, a number of terms and phrases are defined below.

As used herein, all numerical values or numerical ranges include whole integers within or encompassing such ranges and fractions of the values or the integers within or encompassing ranges unless the context clearly indicates otherwise. Thus, for example, reference to a range of 90-100%, includes 91%, 92%, 93%, 94%, 95%, 95%, 96%, 97%, etc., as well as 91.1%, 91.2%, 91.3%, 91.4%, 91.5%, etc., 92.1%, 92.2%, 92.3%, 92.4%, 92.5%, etc., and so forth. In another example, reference to a range of 1-5,000-fold includes 1, 2, 3, 4, 5, 6, 7, 8, 9, 10, 11, 12, 13, 14, 15, 16, 17, 18, 19, 20, fold, etc., as well as 1.1, 1.2, 1.3, 1.4, 1.5, fold, etc., 2.1, 2.2, 2.3, 2.4, 2.5, fold, etc., and so forth.

The terms "a" and "an" as used herein mean "one or more" and include the plural unless the context is inappropriate.

As used herein, the terms "about," "approximately," and "comparable to," when used herein in reference to a value, refer to a value that is similar to the referenced value in the context of that referenced value. In general, those skilled in the art, familiar with the context, will appreciate the relevant degree of variance encompassed by "about," "approximately," and "comparable to" in that context. For example, in some embodiments, the terms "about," "approximately," and "comparable to" may encompass a range of values that fall within 25%, 20%, 19%, 18%, 17%, 16%, 15%, 14%, 13%, 12%, 11, 1%, 9%, 8%, 7%, 6%, 5%, 4%, 3%, 2%, 1%, or less of the referred value.

As used herein, unless otherwise indicated, the term "antibody" is understood to mean an intact antibody (e.g., an intact monoclonal antibody), or a fragment thereof, such as an Fc fragment of an antibody (e.g., an Fc fragment of a monoclonal antibody), or an antigen-binding fragment of an antibody (e.g., an antigen-binding fragment of a monoclonal antibody), including an intact antibody, antigen-binding fragment, or Fc fragment that has been modified, engineered, or chemically conjugated. In general, antibodies are multimeric proteins that contain four polypeptide chains. Two of the polypeptide chains are called immunoglobulin heavy chains (H chains), and two of the polypeptide chains are called immunoglobulin light chains (L chains). The immunoglobulin heavy and light chains are connected by an interchain disulfide bond. The immunoglobulin heavy chains are connected by interchain disulfide bonds. The immunoglobulin heavy chain and/or light chain comprises one or more variable domains. Typically, the light chain may consist of one variable region ($V_L$) and one constant region ($C_L$), and the heavy chain may consist of one variable region (V) and at least three constant regions ($C_H1$, $C_H2$ and $C_H3$). The variable regions determine the binding specificity of the antibody. Each variable region contains three hypervariable regions known as complementarity determining regions (CDRs) flanked by four relatively conserved regions known as framework regions (FRs). The extent of the FRs and CDRs has been defined (Kabat, E. A., et al. (1991) Sequences of Proteins of Immunological Interest, Fifth Edition, U.S. Department of Health and Human Services, NIH Publication No. 91-3242; and Chothia, C. et al. (1987) J. Mol. Biol. 196:901-917). The three CDRs in each variable region (e.g., light chain variable region or heavy chain variable region, with six CDRs total in a typical antibody format), referred to as CDR1, CDR2, and CDR3, collectively contribute to antibody binding specificity. Naturally occurring antibodies have been used as starting material for engineered antibodies, such as chimeric antibodies and humanized antibodies. Examples of antibody-based antigen-binding fragments include Fab, Fab', (Fab')2, Fv, single chain antibodies (e.g., scFv), minibodies, single-domain antibodies (e.g., $V_HH$ fragments), and diabodies. Examples of antibodies that have been modified or engineered include chimeric antibodies, humanized antibodies, and multispecific antibodies (e.g., bispecific antibodies). An example of a chemically conjugated antibody is an antibody conjugated to a toxin moiety.

"Antibody-dependent cell-mediated cytotoxicity" or "ADCC" refers to a form of cytotoxicity in which secreted Ig (immunoglobulin) bound onto Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. PNAS (USA) 95:652-656 (1998).

An "antigen-binding fragment" of an antibody, or "antibody fragment" comprises a portion of an intact antibody, which portion is still capable of antigen binding. In some embodiments, the antibody has a function in addition to that of antigen-binding, and an antigen-binding fragment retains that function. Typically, an antigen-binding fragment comprises the variable region of the antibody. Papain digestion of antibodies produce two identical antigen-binding fragments, called "Fab" fragments, and a residual "Fc" fragment, a designation reflecting the ability to crystallize readily. The Fab fragment consists of an entire light chain along with the variable region domain of the heavy chain ($V_H$), and the first constant domain of one heavy chain ($C_H1$). Each Fab fragment is monovalent with respect to antigen binding, i.e., it has a single antigen-binding site. Pepsin treatment of an antibody yields a single large $F(ab')_2$ fragment which roughly corresponds to two disulfide linked Fab fragments that is capable of cross-linking antigen. Fab' fragments differ from Fab fragments by having a few additional residues at the carboxy terminus of the $C_H1$ domain, including one or more cysteines from the antibody hinge region. Fab'-SH designates a Fab' in which the cysteine residue(s) of the constant domains bear a free thiol group. $F(ab')_2$ antibody fragments originally were produced as pairs of Fab' fragments having hinge cysteines between them. Other chemical couplings of antibody fragments are also known.

As used herein, the term "bivalent," when used in reference to a binding protein, such as an antibody or an antibody-based binding protein, means that the binding protein is capable of binding two molecules of the antigen to which it specifically binds.

As used herein, the term "chimeric antibody" refers to an antibody that has a portion of its heavy and/or light chain identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass.

A "complementarity determining region" (abbreviated "CDR") is a region of hypervariability interspersed within regions that are more conserved, termed "framework regions" (abbreviated "FR"). In some embodiments, the sequences of the framework regions are identical to the framework regions in human germline sequences. In some embodiments, the sequences of the framework regions are modified with respect to the human germline sequence.

As used herein, the phrase "complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g., as described in Gazzano-Santoro et al., J. Immunol. Methods 202:163 (1996), may be performed.

As used herein, the terms "decrease," "decreased," "increase," "increased," or "reduction," "reduced," (e.g., in reference to therapeutic outcomes or effects) have meanings relative to a reference level, as further explained herein.

As used herein, antibody "effector functions" refer to those biological activities attributable to the Fc region (a native sequence Fc region or amino acid sequence variant Fc region) of an antibody, and which typically vary with the antibody isotype. Examples of antibody effector functions include, but are not limited to, C1q binding and complement dependent cytotoxicity, Fc receptor binding, antibody-dependent cell-mediated cytotoxicity (ADCC), phagocytosis, down regulation of cell surface receptors (e.g., B cell receptor), and B cell activation.

As used herein, the phrases "effective amount" and "therapeutically effective amount" of an agent (e.g., a binding protein or as described herein) are used interchangeably and refer to an amount effective, at dosages and for periods of time necessary, to achieve a desired therapeutic result. An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof. An effective amount may vary according to factors such as the type of disease (e.g., disease state), age, sex, and/or weight of the individual, and the ability of a binding protein (or pharmaceutical composition thereof) to elicit a desired response in the individual. An effective amount may also be an amount for which any toxic or detrimental effects of the binding protein or pharmaceutical composition thereof are outweighed by therapeutically beneficial effects.

As used herein, the term "epitope" is an antigenic determinant that interacts with a specific antigen binding site in the variable region of an antibody molecule (or binding protein), known as the paratope, and which is comprised of the six complementary-determining regions of the antibody (or binding protein). A single antigen may have more than one epitope. Epitopes may be conformational or linear. A conformational epitope is comprised of spatially juxtaposed amino acids from different segments of a linear polypeptide chain. A linear epitope is comprised of adjacent amino acid residues in a polypeptide chain.

An "Fc chain" of a dimeric Fc as used herein refers to one of the two polypeptides forming the dimeric Fc region, i.e. a polypeptide comprising C-terminal constant regions of an immunoglobulin heavy chain, capable of stable association with another similar polypeptide. For example, an Fc chain of a dimeric IgG Fc comprises an IgG $C_H2$ and an IgG $C_H3$ constant domain sequence. An Fc chain or a dimeric Fc ("Fc region") can be of any of a variety of Ig classes, e.g., IgA, IgD, IgE, IgG, or IgM. These classes are also designated α, δ, ε, γ, and μ, respectively. Several of these may be further divided into subclasses (isotypes), e.g., IgG1, IgG2, IgG3, IgG4, IgAQ1, and IgA2.

The terms "Fc receptor" and "FcR" are used to describe a receptor that binds to the Fc region of an antibody. For example, an FcR can be a native sequence human FcR. Generally, an FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Immunoglobulins of other isotypes can also be bound by certain FcRs (see, e.g., Janeway et al., *Immuno Biology*: the immune system in health and disease, (Elsevier Science Ltd., NY) (4th ed., 1999)). Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (reviewed in Daëron, *Annu. Rev. Immunol.* 15:203-234 (1997)). FcRs are reviewed in Ravetch and Kinet, *Annu. Rev. Immunol* 9:457-92 (1991); Capel et al., *Immunomethods* 4:25-34 (1994); and de Haas et al., J. Lab. Clin. Med. 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976); and Kim et al., *J. Immunol.* 24:249 (1994)).

As used herein, the term "humanized," when used in reference to an antibody (or binding protein), refers to a form of a non-human (e.g., murine) antibody that is chimeric. A "humanized antibody" contains minimal sequences derived from non-human immunoglobulin. Typically, humanized antibodies are human immunoglobulins (recipient or acceptor antibody) in which hypervariable region residues of the recipient are replaced by hypervariable region residues from a non-human species (donor antibody) such as mouse, rat, rabbit or nonhuman primate having a desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance such as binding affinity. Generally, the humanized antibody will comprise substantially all of at least one, and typically two, variable domains, in which all or substantially all of the hypervariable loops correspond to those of a non-human immunoglobulin and all or substantially all of the framework regions are those of a human immunoglobulin sequence although the framework regions may include one or more amino acid substitutions that improve binding affinity. In some embodiments, no more than six amino acid substitutions in the heavy chain and no more than three amino acid substitutions are used in the light chain in the framework region. The humanized antibody optionally also will comprise at least a portion of an immunoglobulin constant region (e.g., Fc), typically that of a human immunoglobulin.

As used herein, the term "monovalent," when used in reference to a binding protein, such as an antibody or an antibody-based binding protein, means that the binding protein is only capable of binding a single molecule of the antigen to which it specifically binds, and thus is not capable of antigen crosslinking.

"Percent (%) identity" refers to the extent to which two sequences (nucleotide or amino acid) have the same residue at the same positions in an alignment. For example, "an amino acid sequence is X % identical to SEQ ID NO: Y" refers to % identity of the amino acid sequence to SEQ ID NO: Y and is elaborated as X % of residues in the amino acid sequence are identical to the residues of sequence disclosed in SEQ ID NO: Y. Generally, computer programs are employed for such calculations. Exemplary programs that compare and align pairs of sequences include ALIGN (Myers and Miller, 1988), FASTA (Pearson and Lipman, 1988; Pearson, 1990) and gapped BLAST (Altschul et al., 1997), BLASTP, BLASTN, or GCG (Devereux et al., 1984).

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see e.g., Martin, Remington's Pharmaceutical Sciences, 15th Ed., Mack Publ. Co., Easton, PA (1975).

As used herein, "polypeptide," which may be used interchangeably with "protein," refers to a string of at least two amino acids attached to one another by a peptide bond. In some embodiments, a polypeptide may include at least 3-5 amino acids, each of which is attached to others by way of at least one peptide bond. Those of ordinary skill in the art will appreciate that polypeptides can include one or more "non-natural" amino acids or other entities that nonetheless are capable of integrating into a polypeptide chain. In some embodiments, a polypeptide may be glycosylated, e.g., a polypeptide may contain one or more covalently linked sugar moieties. In some embodiments, a single "polypeptide" (e.g., an antibody polypeptide) may comprise two or more individual polypeptide chains, which may in some cases be linked to one another, for example by one or more disulfide bonds or other means.

In some instances, the present disclosure refers to a molecule that is used as a "reference," such as a "reference binding protein." Generally, such reference molecules are identical to the molecule against which it is being compared except for a key aspect, e.g., presence or absence of an Fc modification. In some embodiments, the reference molecules differ from the molecule against which it is being compared in more than one aspect.

As used herein, the phrase "reference level" generally refers to a level considered "normal" for comparison purposes, e.g., a level of an appropriate control. For example, in the context of half-life (e.g. serum half-life) of a protein (e.g., a binding protein) a reference level may refer to the half-life of a "reference binding protein" as described herein.

As used herein, the phrase "specifically binds" or "selectively binds" to a target (e.g., a IL-17 molecule, such as IL-17A and/or IL-17F), when referring to a binding protein as described herein, refers to a binding reaction by which the binding protein binds to the target with higher affinity, higher avidity and/or longer duration than it binds to a structurally different target. In typical embodiments, the binding protein has an affinity of at least 5-fold, 6-fold, 7-fold, 8-fold, 9-fold, 10-fold, 20-fold, 25-fold, 50-fold, 100-fold, 1,000-fold, 10,000-fold, or greater by a specific target compared to an unrelated target when tested under the same affinity assay conditions. The term "specific binding," "binds specifically to," or "is specific to" a particular target, as used herein, may be presented, for example, by a molecule that has an equilibrium dissociation constant $K_d$ for the target to which it binds, e.g., on the order of $10^{-5}$ M, $10^{-6}$ M, $10^{-7}$ M, $10^{-8}$ M, $10^{-9}$ M, $10^{-10}$ M, $10^{-11}$ M, or $10^{-12}$ M, or less. In some embodiments, a binding protein can specifically bind to an epitope on a target that is conserved between species (e.g., structurally conserved between species), e.g., conserved between human and non-human primate species (e.g., structurally conserved between human and non-human primate species). In some embodiments, a binding protein may bind exclusively to a given target, e.g., exclusively to IL-17 but not to other molecules.

The terms "subject," "recipient", "individual", "host", and "patient", are used interchangeably herein and in some embodiments, refer to any mammalian subject for whom diagnosis, treatment, or therapy is desired, particularly humans. "Mammal" for purposes of treatment refers to any animal classified as a mammal, including humans, domestic and farm animals, and laboratory, zoo, sports, or pet animals, such as dogs, horses, cats, cows, sheep, goats, pigs, mice, rats, rabbits, guinea pigs, monkeys etc. In some embodiments, the mammal is human.

As used herein, to "treat" a condition or "treatment" of the condition (e.g., the conditions described herein) is an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e., not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable. "Palliating" a disease, disorder, or condition means that the extent and/or undesirable clinical manifestations of the disease, disorder, or condition are lessened and/or time course of the progression is slowed or lengthened, as compared to the extent or time course in the absence of treatment.

The terms "variable domain" and "variable region" are used interchangeably and refer to the portions of the antibody (or binding protein) or immunoglobulin domains that exhibit variability in their sequence and that are involved in determining the specificity and binding affinity of a particular antibody. Variability is not evenly distributed throughout the variable domains of antibodies; it is concentrated in sub-domains of each of the heavy and light chain variable regions. These sub-domains are called "hypervariable regions" or "complementarity determining regions" (CDRs). The more conserved (i.e., non-hypervariable) portions of the variable domains are called the "framework" regions (FRM or FR) and provide a scaffold for the six CDRs in three-dimensional space to form an antigen-binding surface.

Throughout the description, where compositions are described as having, including, or comprising specific components, or where processes and methods are described as having, including, or comprising specific steps, it is contemplated that, additionally, there are compositions of the present disclosure that consist essentially of, or consist of, the recited components, and that there are processes and methods according to the present disclosure that consist essentially of, or consist of, the recited processing steps.

As a general matter, compositions specifying a percentage are by weight unless otherwise specified. Further, if a variable is not accompanied by a definition, then the previous definition of the variable controls.

IL-17 Binding Proteins

In one aspect, provided are binding proteins that are capable of binding to IL-17. In some embodiments, provided binding proteins are capable of binding, e.g., specifically binding, to both IL-17A and IL-17F ("IL-17A/F binding proteins"). In some embodiments, the IL-17 binding proteins provided herein are capable of specifically binding to IL-17A or IL-17A homodimer. In some embodiments, the IL-17 binding proteins provided herein are capable of specifically binding to IL-17F or IL-17F homodimer. In some embodiments, the IL-17 binding proteins provided herein are capable of specifically binding to IL-17AF heterodimer. In some embodiments, the IL-17 binding proteins provided herein do not specifically bind to other IL-17 isoforms such as IL-17C, IL-17D or IL-17E. In some embodiments, IL-17A/F binding proteins are capable of binding, e.g., specifically binding, to an epitope of human IL-17A and an epitope of human IL-17F. In some embodiments, IL-17A/F binding proteins are capable of binding an epitope that is specific to IL-17A and to IL-17F.

In some embodiments, the binding proteins are antibodies or fragments thereof. In some embodiments, the antibodies or fragments thereof are monoclonal antibodies or fragments thereof. In some embodiments, the antibodies or fragments thereof are chimeric antibodies or fragments thereof. In some embodiments, the antibodies or fragments thereof are humanized antibodies or fragments thereof. In some embodiments, the antibody fragments are antigen-binding fragments of the antibodies. In some embodiments, the antibodies or antigen-binding fragments thereof are human antibodies or antigen-binding fragments thereof.

Antigen-binding fragments may be, e.g., an scFv, a Fab, an scFab (single-chain Fab). As used herein, the term "scFv" is used in accordance with its common usage in the art to refer to a single chain in which the $V_H$ domain and the $V_L$ domain from an antibody are joined, typically via a linker. As used herein, the term "Fab fragment" is used in accordance with its common usage in the art. Fab fragments typically comprise an entire light chain ($V_L$ and $C_L$ domains), the variable region domain of the heavy chain ($V_H$), and the first constant domain of one heavy chain ($C_H1$).

In some embodiments, provided IL-17-binding proteins comprise a heavy chain variable domain comprises complementarity determining regions CDR-H1, CDR-H2, and CDR-H3 with sequences as shown in a table selected from any of Tables 1A-1F. In some embodiments, provided IL-17-binding proteins further comprise a light chain variable domain comprising complementarity determining regions CDR-L1, CDR-L2, and CDR-L3 with sequences as shown in the same table selected from any of Tables 1A-1F.

In some embodiments, provided IL-17-binding proteins comprise a heavy chain variable domain with a heavy chain variable sequence as shown in a table selected from any of Tables 1A-1F. In some embodiments, provided IL-17-binding proteins comprise a heavy chain variable domain which is a variant of the heavy chain variable sequence shown in a table selected from any of Tables 1A-1F, in that the heavy chain variable domain has (1) CDR-H1, CDR-H2, and CDR-H3 with sequences as shown in a table selected from any of Tables 1A-1F and (2) an amino acid sequence that is at least 85%, at least 87.5%, at least 90%, at least 91%, at least 92%, at least 93%, at least 94%, at least 95%, at least 96%, at least 9700, at least 98, or at least 990 identical to the amino acid sequence ofany of a heavy chain variable domain sequence shown in the same table selected from any of Tables A-1F.

In some embodiments, provided L-17-binding proteins comprise a heavy chain variable domain as described herein in a table selected from Tables 1A-1F and further comprise a light chain variable region which has (1) CDR-L1, CDR-L2, and CDR-L3 with sequences as shown in the same table selected from Tables 1A-1F and (2) an amino acid sequence that is at least 85%, at least 87.5%, at least 90%, at least 91%, at least 92%, at least 9300 at least 9400 at least 9500 at least 960%, at least 9700 at least 980%, or at least 9900 identical to the amino acid sequence of the light chain variable domain sequence shown in the same table selected from any of Tables 1A-1F.

TABLE 1A

Exemplary sequences of IL-17-binding proteins

| | Heavy chain sequences | Light chain sequences |
|---|---|---|
| | **CDR sequences - 1011 series antibodies** | |
| Kabat | CDR-H1: DYSMA (SEQ ID NO: 1)<br>CDR-H2: TIGPSGDTYYRDSVKG (SEQ ID NO: 2)<br>CDR-H3: PPQYYEGSIPRLWPAH (SEQ ID NO: 3) | CDR-L1: RADESVRTLMH (SEQ ID NO: 4)<br>CDR-L2: LVSNSEI (SEQ ID NO: 5)<br>CDR-L3: LQTHSYPYT (SEQ ID NO: 6) |
| IMGT | CDR-H1: GFPFSDYS (SEQ ID NO: 7)<br>CDR-H2: IGPSGDT (SEQ ID NO: 8)<br>CDR-H3: ASPPQYYEGSIPRLWPAH (SEQ ID NO: 9) | CDR-L1: ESVRTL (SEQ ID NO: 10)<br>CDR-L2: LVS<br>CDR-L3: LQTHSYPYT (SEQ ID NO: 6) |
| Chothia | CDR-H1: GFPFSDY (SEQ ID NO: 11)<br>CDR-H2: GPSGD (SEQ ID NO: 12)<br>CDR-H3: PQYYEGSIPRLWPA (SEQ ID NO: 13) | CDR-L1: DESVRTL (SEQ ID NO: 14)<br>CDR-L2: LVS<br>CDR-L3: THSYPY (SEQ ID NO: 15) |
| | **Variable Domain and Full H/L Chain Sequences** | |
| Clone 1011A | $V_H$ sequence:<br>EVQLVESGGGLVQPGGSLRLSCAAS<br>GFPFSDYSMAWVRQAPGKGLEWVAT<br>IGPSGDTYYRDSVKGRFTISRDNAK<br>NSLYLQMNSLRAEDTAVYYCASPPQ<br>YYEGSIPRLWPAHWGQGTLVTVSS<br>(SEQ ID NO: 16) | $V_L$ sequence:<br>AIQLTQSPSSLSASVGDRVTITCRA<br>DESVRTLMHWYQQKPGKAPKLLIYL<br>VSNSEIGVPDRFSGSGSGTDFRLTI<br>SSLQPEDFATYYCLQTHSYPYTFGQ<br>GTKVEIK<br>(SEQ ID NO: 17) |

TABLE 1A-continued

| Exemplary sequences of IL-17-binding proteins | | |
|---|---|---|
| | Heavy chain sequences | Light chain sequences |
| Clone 1011A | Heavy chain sequence: EVQLVESGGGLVQPGGSLRLSCAAS GFPFSDYSMAWVRQAPGKGLEWVAT IGPSGDTYYRDSVKGRFTISRDNAK NSLYLQMNSLRAEDTAVYYCASPPQ YYEGSIPRLWPAHWGQGTLVTVSSA STKGPSVFPLAPSSKSTSGGTAALG CLVKDYFPEPVTVSWNSGALTSGVH TFPAVLQSSGLYSLSSVVTVPSSSL GTQTYICNVNHKPSNTKVDKKVEPK SCDKTHTCPPCPAPELLGGPSVFLF PPKPKDTLYITREPEVTCVVVDVSH EDPEVKFNWYVDGVEVHNAKTKPRE EQYNSTYRVVSVLTVLHQDWLNGKE YKCKVSNKALPAPIEKTISKAKGQP REPQVYTLPPSRDELTKNQVSLTCL VKGFYPSDIAVEWESNGQPENNYKT TPPVLDSDGSFFLYSKLTVDKSRWQ QGNVFSCSVMHEALHNHYTQKSLSL SPG (SEQ ID NO: 196) | Light chain sequence: AIQLTQSPSSLSASVGDRVTITCRA DESVRTLMHWYQQKPGKAPKLLIYL VSNSEIGVPDRFSGSGSGTDFRLTI SSLQPEDFATYYCLQTHSYPYTFGQ GTKVEIKRTVAAPSVFIFPPSDEQL KSGTASVVCLLNNFYPREAKVQWKV DNALQSGNSQESVTEQDSKDSTYSL SSTLTLSKADYEKHKVYACEVTHQG LSSPVTKSFNRGEC (SEQ ID NO: 197) |
| Clone 1011D | $V_H$ sequence: EVQLVESGGGLVQPGGSLRLSCAAS GFPFSDYSMAWVRQAPGKGLEWVAT IGPSGDTYYRDSVKGRFTISRDNAK NSLYLQMNSLRAEDTAVYYCASPPQ YYEGSIPRLWPAHWGQGTLVTVSS (SEQ ID NO: 16) | $V_L$ sequence: DIQLTQSPSSLSASVGDRVTITCRA DESVRTLMHWYQQKPGKAPKLLIYL VSNSEIGVPDRFSGSGSGTDFRLTI SSLQPEDFATYYCLQTHSYPYTFGQ GTKVEIK (SEQ ID NO: 18) |
| Clone 1011D | Heavy chain sequence: EVQLVESGGGLVQPGGSLRLSCAAS GFPFSDYSMAWVRQAPGKGLEWVAT IGPSGDTYYRDSVKGRFTISRDNAK NSLYLQMNSLRAEDTAVYYCASPPQ YYEGSIPRLWPAHWGQGTLVTVSSA STKGPSVFPLAPSSKSTSGGTAALG CLVKDYFPEPVTVSWNSGALTSGVH TFPAVLQSSGLYSLSSVVTVPSSSL GTQTYICNVNHKPSNTKVDKKVEPK SCDKTHTCPPCPAPELLGGPSVFLF PPKPKDTLYITREPEVTCVVVDVSH EDPEVKFNWYVDGVEVHNAKTKPRE EQYNSTYRVVSVLTVLHQDWLNGKE YKCKVSNKALPAPIEKTISKAKGQP REPQVYTLPPSRDELTKNQVSLTCL VKGFYPSDIAVEWESNGQPENNYKT TPPVLDSDGSFFLYSKLTVDKSRWQ QGNVFSCSVMHEALHNHYTQKSLSL SPG (SEQ ID NO: 198) | Light chain sequence: DIQLTQSPSSLSASVGDRVTITCRA DESVRTLMHWYQQKPGKAPKLLIYL VSNSEIGVPDRFSGSGSGTDFRLTI SSLQPEDFATYYCLQTHSYPYTFGQ GTKVEIKRTVAAPSVFIFPPSDEQL KSGTASVVCLLNNFYPREAKVQWKV DNALQSGNSQESVTEQDSKDSTYSL SSTLTLSKADYEKHKVYACEVTHQG LSSPVTKSFNRGEC (SEQ ID NO: 199) |

In certain embodiments, the IL-17 binding protein comprises the heavy chain sequence of:

(SEQ ID NO: 306)
EVQLVESGGGLVQPGGSLRLSCAASGFPFSDYSMAWVRQAPGKGLEWVAT
IGPSGDTYYRDSVKGRFTISRDNAKNSLYLQMNSLRAEDTAVYYCASPPQ
YYEGSIPRLWPAHWGQGTLVTVSSASTKGPSVFPLAPSSKSTSGGTAALG
CLVKDYFPEPVTVSWNSGALTSGVHTFPAVLQSSGLYSLSSVVTVPSSSL
GTQTYICNVNHKPSNTKVDKKVEPKSCDKTHTCPPCPAPELLGGPSVFLF

-continued

PPKPKDTLYITREPEVTCVVVDVSHEDPEVKFNWYVDGVEVHNAKTKPRE
EQYNSTYRVVSVLTVLHQDWLNGKEYKCKVSNKALPAPIEKTISKAKGQP
REPQVYTLPPSRDELTKNQVSLTCLVKGFYPSDIAVEWESNGQPENNYKT
TPPVLDSDGSFFLYSKLTVDKSRWQQGNVFSCSVMHEALHNHYTQKSLSL
SPGK and the light chain sequence of SEQ ID NO: 197 or 199.

TABLE 1B

| Exemplary sequences of IL-17-binding proteins | | |
|---|---|---|
| | Heavy chain sequences | Light chain sequences |
| CDR sequences - 1114 series antibodies | | |
| Kabat | CDR-H1: DYSMA (SEQ ID NO: 1)<br>CDR-H2: TITGSGSTYYRDSVKG (SEQ ID NO: 19)<br>CDR-H3: PPQYYEGSIVRLWPAH (SEQ ID NO: 20) | CDR-L1: RADESVRTLMH (SEQ ID NO: 4)<br>CDR-L2: LVSNSEI (SEQ ID NO: 5)<br>CDR-L3: AQSYSMPWT (SEQ ID NO: 21) |
| IMGT | CDR-H1: GFPFSDYS (SEQ ID NO: 7)<br>CDR-H2: ITGSGST (SEQ ID NO: 22)<br>CDR-H3: ASPPQYYEGSIVRLWPAH (SEQ ID NO: 23) | CDR-L1: ESVRTL (SEQ ID NO: 10)<br>CDR-L2: LVS<br>CDR-L3: AQSYSMPWT (SEQ ID NO: 21) |
| Chothia | CDR-H1: GFPFSDY (SEQ ID NO: 11)<br>CDR-H2: TGSGS (SEQ ID NO: 24)<br>CDR-H3: PQYYEGSIVRLWPA (SEQ ID NO: 25) | CDR-L1: DESVRTL (SEQ ID NO: 14)<br>CDR-L2: LVS<br>CDR-L3: SYSMPW (SEQ ID NO: 26) |
| Variable Domain and Full H/L Chain Sequences | | |
| Clone 1114D | $V_H$ sequence:<br>EVQLVESGGGLVQPGGSLRLSCAAS GFPFSDYSMAWVRQAPGKGLEWVAT ITGSGSTYYRDSVKGRFTISRDNAK NSLYLQMNSLRAEDTAVYYCASPPQ YYEGSIVRLWPAHWGQGTLVTVSS (SEQ ID NO: 27) | $V_L$ sequence:<br>DIQLTQSPSSLSASVGDRVTITCRA DESVRTLMHWYQQKPGKAPKLLIYL VSNSEIGVPDRFSGSGSGTDFRLTI SSLQPEDFATYYCAQSYSMPWTFGQ GTKVEIK (SEQ ID NO: 28) |
| Clone 1114D | Heavy chain sequence:<br>EVQLVESGGGLVQPGGSLRLSCAAS GFPFSDYSMAWVRQAPGKGLEWVAT ITGSGSTYYRDSVKGRFTISRDNAK NSLYLQMNSLRAEDTAVYYCASPPQ YYEGSIVRLWPAHWGQGTLVTVSSA STKGPSVFPLAPSSKSTSGGTAALG CLVKDYFPEPVTVSWNSGALTSGVH TFPAVLQSSGLYSLSSVVTVPSSSL GTQTYICNVNHKPSNTKVDKKVEPK SCDKTHTCPPCPAPELLGGPSVFLF PPKPKDTLYITREPEVTCVVVDVSH EDPEVKFNWYVDGVEVHNAKTKPRE EQYNSTYRVVSVLTVLHQDWLNGKE YKCKVSNKALPAPIEKTISKAKGQP REPQVYTLPPSRDELTKNQVSLTCL VKGFYPSDIAVEWESNGQPENNYKT TPPVLDSDGSFFLYSKLTVDKSRWQ QGNVFSCSVMHEALHNHYTQKSLSL SPG (SEQ ID NO: 200) | Light chain sequence:<br>DIQLTQSPSSLSASVGDRVTITCRA DESVRTLMHWYQQKPGKAPKLLIYL VSNSEIGVPDRFSGSGSGTDfRLTI SSLQPEDFATYYCAQSYSMPWTFGQ GTKVEIKRTVAAPSVFIFPPSDEQL KSGTASVVCLLNNFYPREAKVQWKV DNALQSGNSQESVTEQDSKDSTYSL SSTLTLSKADYEKHKVYACEVTHQG LSSPVTKSfNRGEC (SEQ ID NO: 201) |

In certain embodiments, the IL-17 binding protein comprises the heavy chain sequence of:

(SEQ ID NO: 307)

```
EVQLVESGGGLVQPGGSLRLSCAASGFPFSDYSMAWVRQAPGKGLEWVAT
ITGSGSTYYRDSVKGRFTISRDNAKNSLYLQMNSLRAEDTAVYYCASPPQ
YYEGSIVRLWPAHWGQGTLVTVSSASTKGPSVFPLAPSSKSTSGGTAALG
CLVKDYFPEPVTVSWNSGALTSGVHTFPAVLQSSGLYSLSSVVTVPSSSL
GTQTYICNVNHKPSNTKVDKKVEPKSCDKTHTCPPCPAPELLGGPSVFLF
```

-continued

```
PPKPKDTLYITREPEVTCVVVDVSHEDPEVKfNWYVDGVEVHNAKTKPRE
EQYNSTYRVVSVLTVLHQDWLNGKEYKCKVSNKALPAPIEKTISKAKGQP
REPQVYTLPPSRDELTKNQVSLTCLVKGFYPSDIAVEWESNGQPENNYKT
TPPVLDSDGSFFLYSKLTVDKSRWQQGNVFSCSVMHEALHNHYTQKSLSL
SPGK
```

and the light chain sequence of SEQ ID NO: 201.

TABLE 1C

Exemplary sequences of IL-17-binding proteins

| | Heavy chain sequences | Light chain sequences |
|---|---|---|
| **CDR sequences - 1161 series antibodies** | | |
| Kabat | CDR-H1: DYYMA<br>(SEQ ID NO: 29)<br>CDR-H2: TISGSGGTTYYRDSVKG<br>(SEQ ID NO: 30)<br>CDR-H3: PPQYYEGSIPRLWFAH<br>(SEQ ID NO: 31) | CDR-L1: RADESVRTLMH<br>(SEQ ID NO: 4)<br>CDR-L2: LVSNSEI (SEQ ID NO: 5)<br>CDR-L3: LQTHSYPYT<br>(SEQ ID NO: 6) |
| IMGT | CDR-H1: GFRFSDYY<br>(SEQ ID NO: 32)<br>CDR-H2: ISGSGGTT<br>(SEQ ID NO: 33)<br>CDR-H3: ASPPQYYEGSIPRLWFAH<br>(SEQ ID NO: 34) | CDR-L1: ESVRTL (SEQ ID NO: 10)<br>CDR-L2: LVS<br>CDR-L3: LQTHSYPYT (SEQ ID NO: 6) |
| Chothia | CDR-H1: GFRFSDY<br>(SEQ ID NO: 35)<br>CDR-H2: SGSGGT (SEQ ID NO: 36)<br>CDR-H3: PQYYEGSIPRLWFA<br>(SEQ ID NO: 37) | CDR-L1: DESVRTL (SEQ ID NO: 14)<br>CDR-L2: LVS<br>CDR-L3: THSYPY (SEQ ID NO: 15) |
| **Variable Domain and Full H/L Chain Sequences** | | |
| Clone 1161A | $V_H$ sequence:<br>EVQLVESGGGLVQPGGSLRLSCAAS<br>GFRFSDYYMAWVRQAPGKGLEWVAT<br>ISGSGGTTYYRDSVKGRFTISRDNA<br>KNSLYLQMNSLRAEDTAVYYCASPP<br>QYYEGSIPRLWFAHWGQGTLVTVSS<br>(SEQ ID NO: 38) | $V_L$ sequence:<br>AIQLTQSPSSLSASVGDRVTITCRA<br>DESVRTLMHWYQQKPGKAPKLLIYL<br>VSNSEIGVPDRFSGSGSGTDFRLTI<br>SSLQPEDFATYYCLQTHSYPYTFGQ<br>GTKVEIK<br>(SEQ ID NO: 17) |
| Clone 1161A | Heavy chain sequence:<br>EVQLVESGGGLVQPGGSLRLSCAAS<br>GFRFSDYYMAWVRQAPGKGLEWVAT<br>ISGSGGTTYYRDSVKGRFTISRDNA<br>KNSLYLQMNSLRAEDTAVYYCASPP<br>QYYEGSIPRLWFAHWGQGTLVTVSS<br>ASTKGPSVFPLAPSSKSTSGGTAAL<br>GCLVKDYFPEPVTVSWNSGALTSGV<br>HTFPAVLQSSGLYSLSSVVTVPSSS<br>LGTQTYICNVNHKPSNTKVDKKVEP<br>KSCDKTHTCPPCPAPELLGGPSVFL<br>FPPKPKDTLYITREPEVTCVVVDVS<br>HEDPEVKFNWYVDGVEVHNAKTKPR<br>EEQYNSTYRVVSVLTVLHQDWLNGK<br>EYKCKVSNKALPAPIEKTISKAKGQ<br>PREPQVYTLPPSRDELTKNQVSLTC<br>LVKGFYPSDIAVEWESNGQPENNYK<br>TTPPVLDSDGSFFLYSKLTVDKSRW<br>QQGNVFSCSVMHEALHNHYTQKSLS<br>LSPG<br>(SEQ ID NO: 202) | Light chain sequence:<br>AIQLTQSPSSLSASVGDRVTITCRA<br>DESVRTLMHWYQQKPGKAPKLLIYL<br>VSNSEIGVPDRFSGSGSGTDFRLTI<br>SSLQPEDFATYYCLQTHSYPYTFGQ<br>GTKVEIKRTVAAPSVFIFPPSDEQL<br>KSGTASVVCLLNNFYPREAKVQWKV<br>DNALQSGNSQESVTEQDSKDSTYSL<br>SSTLTLSKADYEKHKVYACEVTHQG<br>LSSPVTKSFNRGEC<br>(SEQ ID NO: 203) |
| Clone 1161D | $V_H$ sequence:<br>EVQLVESGGGLVQPGGSLRLSCAAS<br>GFRFSDYYMAWVRQAPGKGLEWVAT<br>ISGSGGTTYYRDSVKGRFTISRDNA<br>KNSLYLQMNSLRAEDTAVYYCASPP<br>QYYEGSIPRLWFAHWGQGTLVTVSS<br>(SEQ ID NO: 38) | $V_L$ sequence:<br>DIQLTQSPSSLSASVGDRVTITCRA<br>DESVRTLMHWYQQKPGKAPKLLIYL<br>VSNSEIGVPDRFSGSGSGTDFRLTI<br>SSLQPEDFATYYCLQTHSYPYTFGQ<br>GTKVEIK<br>(SEQ ID NO: 18) |
| Clone 1161D | Heavy chain sequence:<br>EVQLVESGGGLVQPGGSLRLSCAAS<br>GFRFSDYYMAWVRQAPGKGLEWVAT<br>ISGSGGTTYYRDSVKGRFTISRDNA<br>KNSLYLQMNSLRAEDTAVYYCASPP<br>QYYEGSIPRLWFAHWGQGTLVTVSS<br>ASTKGPSVFPLAPSSKSTSGGTAAL<br>GCLVKDYFPEPVTVSWNSGALTSGV<br>HTFPAVLQSSGLYSLSSVVTVPSSS<br>LGTQTYICNVNHKPSNTKVDKKVEP<br>KSCDKTHTCPPCPAPELLGGPSVFL<br>FPPKPKDTLYITREPEVTCVVVDVS<br>HEDPEVKFNWYVDGVEVHNAKTKPR<br>EEQYNSTYRVVSVLTVLHQDWLNGK | Light chain sequence:<br>DIQLTQSPSSLSASVGDRVTITCRA<br>DESVRTLMHWYQQKPGKAPKLLIYL<br>VSNSEIGVPDRFSGSGSGTDFRLTI<br>SSLQPEDFATYYCLQTHSYPYTFGQ<br>GTKVEIKRTVAAPSVFIFPPSDEQL<br>KSGTASVVCLLNNFYPREAKVQWKV<br>DNALQSGNSQESVTEQDSKDSTYSL<br>SSTLTLSKADYEKHKVYACEVTHQG<br>LSSPVTKSFNRGEC<br>(SEQ ID NO: 205) |

TABLE 1C-continued

| Exemplary sequences of IL-17-binding proteins | |
|---|---|
| Heavy chain sequences | Light chain sequences |
| EYKCKVSNKALPAPIEKTISKAKGQ PREPQVYTLPPSRDELTKNQVSLTC LVKGFYPSDIAVEWESNGQPENNYK TTPPVLDSDGSFFLYSKLTVDKSRW QQGNVFSCSVMHEALHNHYTQKSLS LSPG (SEQ ID NO: 204) | |

In certain embodiments, the IL-17 binding protein comprises the heavy chain sequence of:

(SEQ ID NO: 308)

EVQLVESGGGLVQPGGSLRLSCAASGFRFSDYYMAWVRQAPGKGLEWVAT ISGSGGTTYYRDSVKGRFTISRDNAKNSLYLQMNSLRAEDTAVYYCASPP QYYEGSIPRLWFAHWGQGTLVTVSSASTKGPSVFPLAPSSKSTSGGTAAL GCLVKDYFPEPVTVSWNSGALTSGVHTFPAVLQSSGLYSLSSVVTVPSSS LGTQTYICNVNHKPSNTKVDKKVEPKSCDKTHTCPPCPAPELLGGPSVFL

-continued

FPPKPKDTLYITREPEVTCVVVDVSHEDPEVKFNWYVDGVEVHNAKTKPR EEQYNSTYRVVSVLTVLHQDWLNGKEYKCKVSNKALPAPIEKTISKAKGQ PREPQVYTLPPSRDELTKNQVSLTCLVKGFYPSDIAVEWESNGQPENNYK TTPPVLDSDGSFFLYSKLTVDKSRWQQGNVFSCSVMHEALHNHYTQKSLS LSPGK and the light chain sequence of SEQ ID NO: 203 or 205.

TABLE 1D

| Exemplary sequences of IL-17-binding proteins | | |
|---|---|---|
| | Heavy chain sequences | Light chain sequences |
| CDR sequences - 1181 series antibodies | | |
| Kabat | CDR-H1: SYGMA (SEQ ID NO: 39) CDR-H2: TIDAAGDTYYRDSVKG (SEQ ID NO: 40) CDR-H3: PPQTYEGSIYRLWFAH (SEQ ID NO: 41) | CDR-L1: RADESVKTLMH (SEQ ID NO: 42) CDR-L2: LVSNSEI (SEQ ID NO: 5) CDR-L3: QQTYSAPHT (SEQ ID NO: 43) |
| IMGT | CDR-H1: GFTFPSYG (SEQ ID NO: 44) CDR-H2: IDAAGDT (SEQ ID NO: 45) CDR-H3: AAPPQTYEGSIYRLWFAH (SEQ ID NO: 46) | CDR-L1: ESVKTL (SEQ ID NO: 47) CDR-L2: LVS CDR-L3: QQTYSAPHT (SEQ ID NO: 43) |
| Chothia | CDR-H1: GFTFPSY (SEQ ID NO: 48) CDR-H2: DAAGD (SEQ ID NO: 49) CDR-H3: PQTYEGSIYRLWFA (SEQ ID NO: 50) | CDR-L1: DESVKTL (SEQ ID NO: 51) CDR-L2: LVS CDR-L3: TYSAPH (SEQ ID NO: 52) |
| Variable Domain and Full H/L Chain Sequences | | |
| Clone 1181D | $V_H$ sequence: EVQLVESGGGLVQPGGSLRLSCAAS GFTFPSYGMAWVRQAPGKGLEWVAT IDAAGDTYYRDSVKGRFTISRDNAK NSLYLQMNSLRAEDTAVYYCAAPPQ TYEGS IYRLWFAHWGQGTLVTVSS (SEQ ID NO: 53) | $V_L$ sequence: DIQLTQSPSSLSASVGDRVTITCRA DESVKTLMHWYQQKPGKAPKLLIYL VSNSEIGVPDRFSGSGSGTDFRLTI SSLQPEDFATYYCQQTYSAPHTFGQ GTKVEIK (SEQ ID NO: 54) |
| Clone 1181D | Heavy chain sequence: EVQLVESGGGLVQPGGSLRLSCAAS GFTFPSYGMAWVRQAPGKGLEWVAT IDAAGDTYYRDSVKGRFTISRDNAK NSLYLQMNSLRAEDTAVYYCAAPPQ TYEGSIYRLWFAHWGQGTLVTVSSA STKGPSVFPLAPSSKSTSGGTAALG CLVKDYFPEPVTVSWNSGALTSGVH TFPAVLQSSGLYSLSSVVTVPSSSL GTQTYICNVNHKPSNTKVDKKVEPK SCDKTHTCPPCPAPELLGGPSVFLF | Light chain sequence: DIQLTQSPSSLSASVGDRVTITCRA DESVKTLMHWYQQKPGKAPKLLIYL VSNSEIGVPDRFSGSGSGTDFRLTI SSLQPEDFATYYCQQTYSAPHTFGQ GTKVEIKRTVAAPSVFIFPPSDEQL KSGTASVVCLLNNFYPREAKVQWKV DNALQSGNSQESVTEQDSKDSTYSL SSTLTLSKADYEKHKVYACEVTHQG LSSPVTKSFNRGEC (SEQ ID NO: 207) |

TABLE 1D-continued

| Exemplary sequences of IL-17-binding proteins | |
|---|---|
| Heavy chain sequences | Light chain sequences |
| PPKPKDTLYITREPEVTCVVVDVSH EDPEVKFNWYVDGVEVHNAKTKPRE EQYNSTYRVVSVLTVLHQDWLNGKE YKCKVSNKALPAPIEKTISKAKGQP REPQVYTLPPSRDELTKNQVSLTCL VKGFYPSDIAVEWESNGQPENNYKT TPPVLDSDGSFFLYSKLTVDKSRWQ QGNVFSCSVMHEALHNHYTQKSLSL SPG (SEQ ID NO: 206) | |

In certain embodiments, the IL-17 binding protein comprises the heavy chain sequence of (SEQ ID NO: 309)
EVQLVESGGGLVQPGGSLRLSCAASGFTFPSYGMAWVRQAPGKGLEWVAT
IDAAGDTYYRDSVKGRFTISRDNAKNSLYLQMNSLRAEDTAVYYCAAPPQ
TYEGSIYRLWFAHWGQGTLVTVSSASTKGPSVFPLAPSSKSTSGGTAALG
CLVKDYFPEPVTVSWNSGALTSGVHTFPAVLQSSGLYSLSSVVTVPSSSL
GTQTYICNVNHKPSNTKVDKKVEPKSCDKTHTCPPCPAPELLGGPSVFLF -continued PPKPKDTLYITREPEVTCVVVDVSHEDPEVKFNWYVDGVEVHNAKTKPRE
EQYNSTYRVVSVLTVLHQDWLNGKEYKCKVSNKALPAPIEKTISKAKGQP
REPQVYTLPPSRDELTKNQVSLTCLVKGFYPSDIAVEWESNGQPENNYKT
TPPVLDSDGSFFLYSKLTVDKSRWQQGNVFSCSVMHEALHNHYTQKSLSL
SPGK and the light chain sequence of SEQ ID NO: 207.

TABLE 1E

| Exemplary sequences of IL-17-binding proteins | | |
|---|---|---|
| | Heavy chain sequences | Light chain sequences |
| CDR sequences - 1182 series antibodies | | |
| Kabat | CDR-H1: TYAMA (SEQ ID NO: 55) CDR-H2: TIRGSGESTYYRDSVKG (SEQ ID NO: 56) CDR-H3: PPQYYEGSIDRLWFAH (SEQ ID NO: 57) | CDR-L1: RADESVRTLMH (SEQ ID NO: 4) CDR-L2: LVSNSEI (SEQ ID NO: 5) CDR-L3: LQTYSYPFT (SEQ ID NO: 58) |
| IMGT | CDR-H1: GFPFSTYA (SEQ ID NO: 59) CDR-H2: IRGSGEST (SEQ ID NO: 60) CDR-H3: ASPPQYYEGSIDRLWFAH (SEQ ID NO: 61) | CDR-L1: ESVRTL (SEQ ID NO: 10) CDR-L2: LVS CDR-L3: LQTYSYPFT (SEQ ID NO: 58) |
| Chothia | CDR-H1: GFPFSTY (SEQ ID NO: 62) CDR-H2: RGSGES (SEQ ID NO: 63) CDR-H3: PQYYEGSIDRLWFA (SEQ ID NO: 64) | CDR-L1: DESVRTL (SEQ ID NO: 14) CDR-L2: LVS CDR-L3: TYSYPF (SEQ ID NO: 65) |
| Variable Domain and Full H/L Chain Sequences | | |
| Clone 1182A | $V_H$ sequence: EVQLVESGGGLVQPGGSLRLSCAAS GFPFSTYAMAWVRQAPGKGLEWVAT IRGSGESTYYRDSVKGRFTISRDNA KNSLYLQMNSLRAEDTAVYYCASPP QYYEGSIDRLWFAHWGQGTLVTVSS (SEQ ID NO: 66) | $V_L$ sequence: AIQLTQSPSSLSASVGDRVTITCRA DESVRTLMHWYQQKPGKAPKLLIYL VSNSEIGVPDRFSGSGSGTDFRLTI SSLQPEDFATYYCLQTYSYPFTFGQ GTKVEIK (SEQ ID NO: 67) |
| Clone 1182A | Heavy chain sequence: EVQLVESGGGLVQPGGSLRLSCAAS GFPFSTYAMAWVRQAPGKGLEWVAT IRGSGESTYYRDSVKGRFTISRDNA KNSLYLQMNSLRAEDTAVYYCASPP QYYEGSIDRLWFAHWGQGTLVTVSS ASTKGPSVFPLAPSSKSTSGGTAAL GCLVKDYFPEPVTVSWNSGALTSGV | Light chain sequence: AIQLTQSPSSLSASVGDRVTITCRA DESVRTLMHWYQQKPGKAPKLLIYL VSNSEIGVPDRFSGSGSGTDFRLTI SSLQPEDFATYYCLQTYSYPFTFGQ GTKVEIKRTVAAPSVFIFPPSDEQL KSGTASVVCLLNNFYPREAKVQWKV DNALQSGNSQESVTEQDSKDSTYSL |

TABLE 1E-continued

| Exemplary sequences of IL-17-binding proteins | | |
|---|---|---|
| | Heavy chain sequences | Light chain sequences |
| | HTFPAVLQSSGLYSLSSVVTVPSSS<br>LGTQTYICNVNHKPSNTKVDKKVEP<br>KSCDKTHTCPPCPAPELLGGPSVFL<br>FPPKPKDTLYITREPEVTCVVVDVS<br>HEDPEVKFNWYVDGVEVHNAKTKPR<br>EEQYNSTYRVVSVLTVLHQDWLNGK<br>EYKCKVSNKALPAPIEKTISKAKGQ<br>PREPQVYTLPPSRDELTKNQVSLTC<br>LVKGFYPSDIAVEWESNGQPENNYK<br>TTPPVLDSDGSFFLYSKLTVDKSRW<br>QQGNVFSCSVMHEALHNHYTQKSLS<br>LSPG<br>(SEQ ID NO: 208) | SSTLTLSKADYEKHKVYACEVTHQG<br>LSSPVTKSFNRGEC<br>(SEQ ID NO: 209) |
| Clone 1182D | $V_H$ sequence:<br>EVQLVESGGGLVQPGGSLRLSCAAS<br>GFPFSTYAMAWVRQAPGKGLEWVAT<br>IRGSGESTYYRDSVKGRFTISRDNA<br>KNSLYLQMNSLRAEDTAVYYCASPP<br>QYYEGSIDRLWFAHWGQGTLVTVSS<br>(SEQ ID NO: 66) | $V_L$ sequence:<br>DIQLTQSPSSLSASVGDRVTITCRA<br>DESVRTLMHWYQQKPGKAPKLLIYL<br>VSNSEIGVPDRFSGSGSGTDFRLTI<br>SSLQPEDFATYYCLQTYSYPFTFGQ<br>GTKVEIK<br>(SEQ ID NO: 68) |
| Clone 1182D | Heavy chain sequence:<br>EVQLVESGGGLVQPGGSLRLSCAAS<br>GFPFSTYAMAWVRQAPGKGLEWVAT<br>IRGSGESTYYRDSVKGRFTISRDNA<br>KNSLYLQMNSLRAEDTAVYYCASPP<br>QYYEGSIDRLWFAHWGQGTLVTVSS<br>ASTKGPSVFPLAPSSKSTSGGTAAL<br>GCLVKDYFPEPVTVSWNSGALTSGV<br>HTFPAVLQSSGLYSLSSVVTVPSSS<br>LGTQTYICNVNHKPSNTKVDKKVEP<br>KSCDKTHTCPPCPAPELLGGPSVFL<br>FPPKPKDTLYITREPEVTCVVVDVS<br>HEDPEVKFNWYVDGVEVHNAKTKPR<br>EEQYNSTYRVVSVLIVLHQDWLNGK<br>EYKCKVSNKALPAPIEKTISKAKGQ<br>PREPQVYTLPPSRDELTKNQVSLTC<br>LVKGFYPSDIAVEWESNGQPENNYK<br>TTPPVLDSDGSFFLYSKLTVDKSRW<br>QQGNVFSCSVMHEALHNHYTQKSLS<br>LSPG<br>(SEQ ID NO: 300) | Light chain sequence:<br>DIQLTQSPSSLSASVGDRVTITCRA<br>DESVRTLMHWYQQKPGKAPKLLIYL<br>VSNSEIGVPDRFSGSGSGTDFRLTI<br>SSLQPEDFATYYCLQTYSYPFTFGQ<br>GTKVEIKRTVAAPSVFIFPPSDEQL<br>KSGTASVVCLLNNFYPREAKVQWKV<br>DNALQSGNSQESVTEQDSKDSTYSL<br>SSTLTLSKADYEKHKVYACEVTHQG<br>LSSPVTKSFNRGEC<br>(SEQ ID NO: 301) |

In certain embodiments, the IL-17 binding protein comprises the heavy chain sequence of:

```
                                        (SEQ ID NO: 310)
EVQLVESGGGLVQPGGSLRLSCAASGEPESTYAMAWVRQAPGKGLEWVAT

IRGSGESTYYRDSVKGRFTISRDNAKNSLYLQMNSLRAEDTAVYYCASPP

QYYEGSIDRLWFAHWGQGTLVTVSSASTKGPSVFPLAPSSKSTSGGTAAL

GCLVKDYFPEPVTVSWNSGALTSGVHTFPAVLQSSGLYSLSSVVTVPSSS

LGTQTYICNVNHKPSNTKVDKKVEPKSCDKTHTCPPCPAPELLGGPSVFL
```

-continued

```
FPPKPKDTLYITREPEVTCVVVDVSHEDPEVKFNWYVDGVEVHNAKTKPR

EEQYNSTYRVVSVLTVLHQDWLNGKEYKCKVSNKALPAPIEKTISKAKGQ

PREPQVYTLPPSRDELTKNQVSLTCLVKGFYPSDIAVEWESNGQPENNYK

TTPPVLDSDGSFFLYSKLTVDKSRWQQGNVFSCSVMHEALHNHYTQKSLS

LSPGK and the light chain sequence of SEQ ID NO:

209 or 301.
```

TABLE 1F

| Exemplary sequences of IL-17-binding proteins | | |
|---|---|---|
| | Heavy chain sequences | Light chain sequences |
| CDR sequences - 2001 and 2002 series antibodies | | |
| Kabat | CDR-H1: DYNMA<br>(SEQ ID NO: 69)<br>CDR-H2: TITYEGRNTYYRDSVKG<br>(SEQ ID NO: 70) | CDR-L1: RADESVRTLMH<br>(SEQ ID NO: 4)<br>CDR-L2: LVSNSEI<br>(SEQ ID NO: 5) |

TABLE 1F-continued

| Exemplary sequences of IL-17-binding proteins | | |
|---|---|---|
| | Heavy chain sequences | Light chain sequences |
| | CDR-H3: PPQYYEGSIYRLWFAH (SEQ ID NO: 71) | CDR-L3: QQTWSDPWT (SEQ ID NO: 72) |
| IMGT | CDR-H1: GFTFSDYN (SEQ ID NO: 73)<br>CDR-H2: ITYEGRNT (SEQ ID NO: 74)<br>CDR-H3: ASPPQYYEGSIYRLWFAH (SEQ ID NO: 75) | CDR-L1: ESVRTL (SEQ ID NO: 10)<br>CDR-L2: LVS<br>CDR-L3: QQTWSDPWT (SEQ ID NO: 72) |
| Chothia | CDR-H1: GFTFSDY (SEQ ID NO: 76)<br>CDR-H2: TYEGRN (SEQ ID NO: 77)<br>CDR-H3: PQYYEGSIYRLWFA (SEQ ID NO: 78) | CDR-L1: DESVRTL (SEQ ID NO: 14)<br>CDR-L2: LVS<br>CDR-L3: TWSDPW (SEQ ID NO: 79) |
| Variable Domain and Full H/L Chain Sequences | | |
| Clone 2001D | $V_H$ sequence:<br>EVQLVESGGGLVQPGGSLRLSCAAS<br>GFTFSDYNMAWVRQAPGKGLEWVAT<br>ITYEGRNTYYRDSVKGRFTISRDNA<br>KNSLYLQMNSLRAEDTAVYYCASPP<br>QYYEGSIYRLWFAHWGQGTLVTVSS<br>(SEQ ID NO: 80) | $V_L$ sequence:<br>DIQLTQSPSSLSASVGDRVTITCRA<br>DESVRTLMHWYQQKPGKAPKLLIYL<br>VSNSEIGVPDRFSGSGSGTDFRLTI<br>SSLQPEDFATYYCQQTWSDPWTFGQ<br>GTKVEIK<br>(SEQ ID NO: 81) |
| Clone 2001D | Heavy chain sequence:<br>EVQLVESGGGLVQPGGSLRLSCAAS<br>GFTFSDYNMAWVRQAPGKGLEWVAT<br>ITYEGRNTYYRDSVKGRFTISRDNA<br>KNSLYLQMNSLRAEDTAVYYCASPP<br>QYYEGSIYRLWFAHWGQGTLVTVSS<br>ASTKGPSVFPLAPSSKSTSGGTAAL<br>GCLVKDYFPEPVTVSWNSGALTSGV<br>HTFPAVLQSSGLYSLSSVVTVPSSS<br>LGTQTYICNVNHKPSNTKVDKKVEP<br>KSCDKTHTCPPCPAPELLGGPSVFL<br>FPPKPKDTLYITREPEVTCVVVDVS<br>HEDPEVKFNWYVDGVEVHNAKTKPR<br>EEQYNSTYRVVSVLTVLHQDWLNGK<br>EYKCKVSNKALPAPIEKTISKAKGQ<br>PREPQVYTLPPSRDELTKNQVSLTC<br>LVKGFYPSDIAVEWESNGQPENNYK<br>TTPPVLDSDGSFFLYSKLTVDKSRW<br>QQGNVFSCSVMHEALHNHYTQKSLS<br>LSPG<br>(SEQ ID NO: 302) | Light chain sequence:<br>DIQLTQSPSSLSASVGDRVTITCRA<br>DESVRTLMHWYQQKPGKAPKLLIYL<br>VSNSEIGVPDRFSGSGSGTDFRLTI<br>SSLQPEDFATYYCQQTWSDPWTFGQ<br>GTKVEIKRTVAAPSVFIFPPSDEQL<br>KSGTASVVCLLNNFYPREAKVQWKV<br>DNALQSGNSQESVTEQDSKDSTYSL<br>SSTLTLSKADYEKHKVYACEVTHQG<br>LSSPVTKSFNRGEC<br>(SEQ ID NO: 303) |
| Clone 2002D | $V_H$ sequence:<br>EVQLVESGGGLVQPGGSLRLSCAAS<br>GFTFSDYNMAWVRQAPGKGLEWVAT<br>ITYEGRNTYYRDSVKGRFTISRDNA<br>KNSLYLQMNSLRAEDTAVYYCASPP<br>QYYEGSIYRLWFAHWGQGTLVTVSS<br>(SEQ ID NO: 80) | $V_L$ sequence:<br>DIQMTQSPSSLSASVGDRVTITCRA<br>DESVRTLMHWYQQKPGKAPKLLIYL<br>VSNSEIGVPDRFSGSGSGTDFRLTI<br>SSLQPEDFATYYCQQTWSDPWTFGQ<br>GTKVEIK<br>(SEQ ID NO: 82) |
| Clone 2002D | Heavy chain sequence:<br>EVQLVESGGGLVQPGGSLRLSCAAS<br>GFTFSDYNMAWVRQAPGKGLEWVAT<br>ITYEGRNTYYRDSVKGRFTISRDNA<br>KNSLYLQMNSLRAEDTAVYYCASPP<br>QYYEGSIYRLWFAHWGQGTLVTVSS<br>ASTKGPSVFPLAPSSKSTSGGTAAL<br>GCLVKDYFPEPVTVSWNSGALTSGV<br>HTFPAVLQSSGLYSLSSVVTVPSSS<br>LGTQTYICNVNHKPSNTKVDKKVEP<br>KSCDKTHTCPPCPAPELLGGPSVFL<br>FPPKPKDTLYITREPEVTCVVVDVS<br>HEDPEVKFNWYVDGVEVHNAKTKPR<br>EEQYNSTYRVVSVLTVLHQDWLNGK<br>EYKCKVSNKALPAPIEKTISKAKGQ<br>PREPQVYTLPPSRDELTKNQVSLTC<br>LVKGFYPSDIAVEWESNGQPENNYK | Light chain sequence:<br>DIQMTQSPSSLSASVGDRVTITCRA<br>DESVRTLMHWYQQKPGKAPKLLIYL<br>VSNSEIGVPDRFSGSGSGTDFRLTI<br>SSLQPEDFATYYCQQTWSDPWTFGQ<br>GTKVEIKRTVAAPSVFIFPPSDEQL<br>KSGTASVVCLLNNFYPREAKVQWKV<br>DNALQSGNSQESVTEQDSKDSTYSL<br>SSTLTLSKADYEKHKVYACEVTHQG<br>LSSPVTKSFNRGEC<br>(SEQ ID NO: 305) |

TABLE 1F-continued

| Exemplary sequences of IL-17-binding proteins | |
|---|---|
| Heavy chain sequences | Light chain sequences |
| TTPPVLDSDGSFFLYSKLTVDKSRW QQGNVFSCSVMHEALHNHYTQKSLS LSPG (SEQ ID NO: 304) | |

In certain embodiments, the IL-17 binding protein comprises the heavy chain sequence of:

```
                                        (SEQ ID NO: 311)
EVQLVESGGGLVQPGGSLRLSCAASGFTFSDYNMAWVRQAPGKGLEWVAT
ITYEGRNTYYRDSVKGRFTISRDNAKNSLYLQMNSLRAEDTAVYYCASPP
QYYEGSIYRLWFAHWGQGTLVTVSSASTKGPSVFPLAPSSKSTSGGTAAL
GCLVKDYFPEPVTVSWNSGALTSGVHTFPAVLQSSGLYSLSSVVTVPSSS
LGTQTYICNVNHKPSNTKVDKKVEPKSCDKTHTCPPCPAPELLGGPSVFL
FPPKPKDTLYITREPEVTCVVVDVSHEDPEVKFNWYVDGVEVHNAKTKPR
EEQYNSTYRVVSVLTVLHQDWLNGKEYKCKVSNKALPAPIEKTISKAKGQ
PREPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSLS
LSPGK and the light chain sequence of SEQ ID NO:
303 or 305.
```

In some embodiments, provided are IL-17-binding proteins comprising a heavy chain having the amino acid sequence of SEQ ID NO: 196 or 306 and a light chain having the amino acid sequence of SEQ ID NO: 197.

In some embodiments, provided are IL-17-binding proteins comprising a heavy chain having the amino acid sequence of SEQ ID NO: 198 or 306 and a light chain having the amino acid sequence of SEQ ID NO: 199.

In some embodiments, provided are IL-17-binding proteins comprising a heavy chain having the amino acid sequence of SEQ ID NO: 200 or 307 and a light chain having the amino acid sequence of SEQ ID NO: 201.

In some embodiments, provided are IL-17-binding proteins comprising a heavy chain having the amino acid sequence of SEQ ID NO: 202 or 308 and a light chain having the amino acid sequence of SEQ ID NO: 203.

In some embodiments, provided are IL-17-binding proteins comprising a heavy chain having the amino acid sequence of SEQ ID NO: 204 or 308 and a light chain having the amino acid sequence of SEQ ID NO: 205.

In some embodiments, provided are IL-17-binding proteins comprising a heavy chain having the amino acid sequence of SEQ ID NO: 206 or 309 and a light chain having the amino acid sequence of SEQ ID NO: 207.

In some embodiments, provided are IL-17-binding proteins comprising a heavy chain having the amino acid sequence of SEQ ID NO: 208 or 310 and a light chain having the amino acid sequence of SEQ ID NO: 209.

In some embodiments, provided are IL-17-binding proteins comprising a heavy chain having the amino acid sequence of SEQ ID NO: 300 or 310 and a light chain having the amino acid sequence of SEQ ID NO: 301.

In some embodiments, provided are IL-17-binding proteins comprising a heavy chain having the amino acid sequence of SEQ ID NO: 302 or 311 and a light chain having the amino acid sequence of SEQ ID NO: 303.

In some embodiments, provided are IL-17-binding proteins comprising a heavy chain having the amino acid sequence of SEQ ID NO: 304 or 311 and a light chain having the amino acid sequence of SEQ ID NO: 305.

Fc Polypeptides

Binding proteins suitable for use in accordance with the present disclosure typically comprise an immunoglobulin Fc region. Fc regions typically comprise one or more Fc chains (e.g., Fc polypeptides, such as a first Fc polypeptide and a second Fc polypeptide). An IgG Fc polypeptide typically contains two constant heavy domains ($C_H2$ and $C_H3$) and a hinge region connected to the $C_H2$ domain. Fc regions may typically comprise two Fc polypeptide which dimerize with one another; however, an Fc region may have a single Fc polypeptide or more than two Fc polypeptide, e.g., as may be present in some antibody formats.

In some embodiments, binding proteins comprise an IgG1 Fc region (e.g., human IgG1 Fc region), that is, except for having particular residue(s) at certain positions as noted herein, the Fc region has an amino acid sequence that is substantially similar to that of the Fc region within a wild type IgG1 Fc. In some embodiments, the wild type IgG1 Fc is a human IgG1 Fc, in which each Fc chain has an amino acid sequence of SEQ ID NO: 84. In some embodiments, binding proteins comprise an Fc region, each Fc chain of which has an amino acid sequence that is at least 85%, at least 87.5%, at least 90%, at least 91%, at least 92%, at least 93%, at least 94%, at least 95%, at least 96%, at least 97%, at least 98%, or at least 99% identical to that of an Fc chain within a wild-type IgG1 Fc, e.g., a polypeptide having an amino acid sequence of SEQ ID NO: 84.

In some embodiments, binding proteins comprise an IgG2 Fc region (e.g., human IgG2 Fc region), that is, except for having particular residue(s) at certain positions as noted herein, the Fc region has an amino acid sequence that is substantially similar to that of the Fc region within a wild type IgG2 Fc. In some embodiments, the wild type IgG2 Fc is a human IgG2 Fc, in which each Fc chain has an amino acid sequence of SEQ ID NO: 86. In some embodiments, binding proteins comprise an Fc region, each Fc chain of which has an amino acid sequence that is at least 85%, at least 87.5%, at least 90%, at least 91%, at least 92%, at least 93%, at least 94%, at least 95%, at least 96%, at least 97%, at least 98%, or at least 99% identical to that of an Fc chain within a wild-type IgG2 Fc, e.g., a polypeptide having an amino acid sequence of SEQ ID NO: 86.

In some embodiments, binding proteins comprise an IgG4 Fc region (e.g., human IgG4 Fc region), that is, except for having particular residue(s) at certain positions as noted herein, the Fc region has an amino acid sequence that is substantially similar to that of the Fc region within a wild type IgG4 Fc. In some embodiments, the wild type IgG4 Fc is a human IgG4 Fc, in which each Fc chain has an amino acid sequence of SEQ ID NO: 85. In some embodiments, binding proteins comprise an Fc region, each Fc chain of which has an amino acid sequence that is at least 85%, at least 87.5%, at least 90%, at least 91%, at least 92%, at least 93%, at least 94%, at least 95%, at least 96%, at least 97%, at least 98%, or at least 99% identical to that of an Fc chain within a wild-type IgG4 Fc, e.g., a polypeptide having an amino acid sequence of SEQ ID NO: 85.

Fc Mutations

In certain embodiments, Fc regions are modified (e.g., substituted, inserted and/or deleted) at one more amino acid residues. In certain embodiments, modifications to Fc regions alter the half-life of a molecule (e.g., binding protein) which comprises the Fc region by altering (e.g., enhancing) binding to an Fc receptor such as the neonatal Fc receptor (FcRn.) For example, in some embodiments, the Fc region is modified to enhance the half-life of the molecule (e.g., binding protein) which comprises the Fc region. Non-limiting examples of half-life-enhancing mutations or sets of mutations include, e.g., M252Y/S254T/T256E (YTE), M428L/N434S (LS), H433K/N434F (KF), and L309D/Q311H/N434S (DHS).

In some embodiments, the antibody or antigen binding fragment thereof has a half-life of at least about 25 days (e.g., 25 days, 26 days, 27 days, 28 days, 29 days, 30 days, 31 days, 32 days, or 33 days). In one embodiment, the antibody or antigen binding fragment thereof has a half-life of about 30 days. In one embodiment, the antibody or antigen binding fragment thereof has a half-life of about 31 days. In one embodiment, the antibody or antigen binding fragment thereof has a half-life of about 32 days. In some embodiments, the half-life of the antibody or antigen binding fragment thereof is determined in cynomolgus monkeys or other non-human primates (NHPs).

In some embodiments, the half-life of the antibody or antigen binding fragment thereof is determined in humans.

In some embodiments, modifications to Fc regions prevent Fab arm (e.g., IgG4 Fab arm) exchange. An example of such a modification in the context of an IgG4 Fc region is the S228P mutation.

In some embodiments, modifications to Fc regions reduce or abrogate effector functions, e.g., Fcγ receptor-mediated effector functions. Non-limiting examples of effector-reducing mutations or sets of mutations include, e.g., aglycosylation mutations (e.g., N297A or N297Q or N297G), L234A/L235A (for IgG1 Fc regions), H268Q/V309L/A330S/P331S (for IgG2 Fc regions), and V234A/G237A/P238S/H268A/V309L/A330S/P331S (for IgG2 Fc regions).

In some embodiments, modifications to Fc regions enhance Fcγ receptor-mediated effector functions. Non-limiting examples of FcγRIIIa effector-enhancing mutations or sets of mutations include, e.g., F243L/R292P/Y300L/V305I/P396L, S298A/E333A/K334A, S239D/I332E, S239D/I332E/A330L, and L234Y/L235Q/G236W/S239M/H268D/D270E/S298A in one chain and D270E/K326D/A330M/K334E in another chain.

In some embodiments, modifications to Fc regions enhance antibody-dependent cellular phagocytosis (ADCP). A non-limiting example of an ADCP-enhancing set of mutations is G236A/S239D/I332E.

In some embodiments, modifications to Fc regions enhance complement-dependent cytotoxicity (CDC) and/or binding to complement protein C1q. Non-limiting examples of an CDC-enhancing and/or C1q-binding-enhancing sets of mutations include, e.g., K326W/E333S, S267E/H268F/S324T, and E345R/E430G/S440Y.

In some embodiments, modifications to Fc regions enhance co-engagement with antigens and Fcγ receptors. Non-limiting examples of co-engagement-enhancing sets of mutations include, e.g., S267E/L328F and N325S/L328F.

Unless otherwise specified herein, numbering of amino acid residues in the Fc region or constant region is according to the EU numbering system, also called the EU index, as described in Kabat et al, Sequences of Proteins of Immunological Interest, 5th Ed. Public Health Service, National Institutes of Health, Bethesda, MD, 1991.

Amino acid sequences of exemplary Fc sequences are provided in Table 2.

TABLE 2

Exemplary Fc Sequences

| Name | SEQ ID NO | Fc chain sequence |
|---|---|---|
| hIgG1 | 84 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPELLGGPSVFLFPPK PKDTLMISRTPEVTCVVVDVSHEDPEVKFNWYVDGVEVHNA KTKPREEQYNSTYRVVSVLTVLHQDWLNGKEYKCKVSNKAL PAPIEKTISKAKGQPREPQVYTLPPSRDELTKNQVSLTCLVKG FYPSDIAVEWESNGQPENNYKTTPPVLDSDGSFFLYSKLTVDK SRWQQGNVFSCSVMHEALHNHYTQKSLSLSPG |
| hIgG4 | 85 | ASTKGPSVFPLAPCSRSTSESTAALGCLVKDYFPEPVTVSWNS GALTSGVHTFPAVLQSSGLYSLSSVVTVPSSSLGTKTYTCNVD HKPSNTKVDKRVESKYGPPCPSCPAPEFLGGPSVFLFPPKPKD TLMISRTPEVTCVVVDVSQEDPEVQFNWYVDGVEVHNAKTK PREEQFNSTYRVVSVLTVLHQDWLNGKEYKCKVSNKGLPSSI EKTISKAKGQPREPQVYTLPPSQEEMTKNQVSLTCLVKGFYPS DIAVEWESNGQPENNYKTTPPVLDSDGSFFLYSRLTVDKSRW QEGNVFSCSVMHEALHNHYTQKSLSLSLGK |
| hIgG2 | 86 | ASTKGPSVFPLAPCSRSTSESTAALGCLVKDYFPEPVTVSWNS GALTSGVHTFPAVLQSSGLYSLSSVVTVPSSNFGTQTYTCNVD HKPSNTKVDKTVERKCCVECPPCPAPPVAGPSVFLFPPKPKDT LMISRTPEVTCVVVDVSHEDPEVQFNWYVDGVEVHNAKTKP REEQFNSTFRVVSVLTVVHQDWLNGKEYKCKVSNKGLPAPIE KTISKTKGQPREPQVYTLPPSREEMTKNQVSLTCLVKGFYPSD IAVEWESNGQPENNYKTTPPMLDSDGSFFLYSKLTVDKSRWQ QGNVFSCSVMHEALHNHYTQKSLSLSPG |

TABLE 2-continued

Exemplary Fc Sequences

| Name | SEQ ID NO | Fc chain sequence |
|---|---|---|
| IgG4-SP (S228P) | 87 | ASTKGPSVFPLAPCSRSTSESTAALGCLVKDYFPEPVTVSWNS GALTSGVHTFPAVLQSSGLYSLSSVVTVPSSSLGTKTYTCNVD HKPSNTKVDKRVESKYGPPCPPCPAPEFLGGPSVFLFPPKPKD TLMISRTPEVTCVVVDVSQEDPEVQFNWYVDGVEVHNAKTK PREEQFNSTYRVVSVLTVLHQDWLNGKEYKCKVSNKGLPSSI EKTISKAKGQPREPQVYTLPPSQEEMTKNQVSLTCLVKGFYPS DIAVEWESNGQPENNYKTTPPVLDSDGSFFLYSRLTVDKSRW QEGNVFSCSVMHEALHNHYTQKSLSLSLGK |
| IgG4-SPLE (S228P/ L235E) | 88 | ASTKGPSVFPLAPCSRSTSESTAALGCLVKDYFPEPVTVSWNS GALTSGVHTFPAVLQSSGLYSLSSVVTVPSSSLGTKTYTCNVD HKPSNTKVDKRVESKYGPPCPPCPAPEELGGPSVFLFPPKPKD TLMISRTPEVTCVVVDVSQEDPEVQFNWYVDGVEVHNAKTK PREEQFNSTYRVVSVLTVLHQDWLNGKEYKCKVSNKGLPSSI EKTISKAKGQPREPQVYTLPPSQEEMTKNQVSLTCLVKGFYPS DIAVEWESNGQPENNYKTTPPVLDSDGSFFLYSRLTVDKSRW QEGNVFSCSVMHEALHNHYTQKSLSLSLGK |
| hIgG1- N297A | 89 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPELLGGPSVFLFPPK PKDTLMISRTPEVTCVVVDVSHEDPEVKFNWYVDGVEVHNA KTKPREEQYASTYRVVSVLTVLHQDWLNGKEYKCKVSNKAL PAPIEKTISKAKGQPREPQVYTLPPSRDELTKNQVSLTCLVKG FYPSDIAVEWESNGQPENNYKTTPPVLDSDGSFFLYSKLTVDK SRWQQGNVFSCSVMHEALHNHYTQKSLSLSPG |
| hIgG1- D265A | 90 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPELLGGPSVFLFPPK PKDTLMISRTPEVTCVVVAVSHEDPEVKFNWYVDGVEVHNA KTKPREEQYNSTYRVVSVLTVLHQDWLNGKEYKCKVSNKAL PAPIEKTISKAKGQPREPQVYTLPPSRDELTKNQVSLTCLVKG FYPSDIAVEWESNGQPENNYKTTPPVLDSDGSFFLYSKLTVDK SRWQQGNVFSCSVMHEALHNHYTQKSLSLSPG |
| hIgG1- LALA (L234A/ L235A) | 91 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPEAAGGPSVFLFPPK PKDTLMISRTPEVTCVVVDVSHEDPEVKFNWYVDGVEVHNA KTKPREEQYNSTYRVVSVLTVLHQDWLNGKEYKCKVSNKAL PAPIEKTISKAKGQPREPQVYTLPPSRDELTKNQVSLTCLVKG FYPSDIAVEWESNGQPENNYKTTPPVLDSDGSFFLYSKLTVDK SRWQQGNVFSCSVMHEALHNHYTQKSLSLSPG |
| hIgG1- LAGA (L235A/ G237A) | 92 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPELAGAPSVFLFPPK PKDTLMISRTPEVTCVVVDVSHEDPEVKFNWYVDGVEVHNA KTKPREEQYNSTYRVVSVLTVLHQDWLNGKEYKCKVSNKAL PAPIEKTISKAKGQPREPQVYTLPPSRDELTKNQVSLTCLVKG FYPSDIAEWESNGQPENNYKTTPPVLDSDGSFFLYSKLTVDK SRWQQGNVFSCSVMHEALHNHYTQKSLSLSPG |
| hIgG1- LALAGA (L234A/ L235A/ G237A) | 93 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPEAAGAPSVFLFPPK PKDTLMISRTPEVTCVVVDVSHEDPEVKFNWYVDGVEVHNA KTKPREEQYNSTYRVVSVLTVLHQDWLNGKEYKCKVSNKAL PAPIEKTISKAKGQPREPQVYTLPPSRDELTKNQVSLTCLVKG FYPSDIAVEWESNGQPENNYKTTPPVLDSDGSFFLYSKLTVDK SRWQQGNVFSCSVMHEALHNHYTQKSLSLSPG |
| hIgG1- LALAPG (L234A/ L235A/ P329G) | 94 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPEAAGGPSVFLFPPK PKDTLMISRTPEVTCVVVDVSHEDPEVKFNWYVDGVEVHNA KTKPREEQYNSTYRVVSVLTVLHQDWLNGKEYKCKVSNKAL GAPIEKTISKAKGQPREPQVYTLPPSRDELTKNQVSLTCLVKG FYPSDIAVEWESNGQPENNYKTTPPVLDSDGSFFLYSKLTVDK SRWQQGNVFSCSVMHEALHNHYTQKSLSLSPG |
| hIgG1-YTE (M252Y/ S254T/ T256E) | 95 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPELLGGPSVFLFPPK PKDTLYITREPEVTCVVVDVSHEDPEVKFNWYVDGVEVHNA |

TABLE 2-continued

Exemplary Fc Sequences

| Name | SEQ ID NO | Fc chain sequence |
|---|---|---|
| | | KTKPREEQYNSTYRVVSVLTVLHQDWLNGKEYKCKVSNKAL PAPIEKTISKAKGQPREPQVYTLPPSRDELTKNQVSLTCLVKG FYPSDIAVEWESNGQPENNYKTTPPVLDSDGSFFLYSKLTVDK SRWQQGNVFSCSVMHEALHNHYTQKSLSLSPG |
| hIgG1-N297A/YTE | 96 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPELLGGPSVFLFPPK PKDTLYITREPEVTCVVVDVSHEDPEVKFNWYVDGVEVHNA KTKPREEQYASTYRVVSVLTVLHQDWLNGKEYKCKVSNKAL PAPIEKTISKAKGQPREPQVYTLPPSRDELTKNQVSLTCLVKG FYPSDIAVEWESNGQPENNYKTTPPVLDSDGSFFLYSKLTVDK SRWQQGNVFSCSVMHEALHNHYTQKSLSLSPG |
| hIgG1-D265A/YTE | 97 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPELLGGPSVFLFPPK PKDTLYITREPEVTCVVVAVSHEDPEVKFNWYVDGVEVHNA KTKPREEQYNSTYRVVSVLTVLHQDWLNGKEYKCKVSNKAL PAPIEKTISKAKGQPREPQVYTLPPSRDELTKNQVSLTCLVKG FYPSDIAVEWESNGQPENNYKTTPPVLDSDGSFFLYSKLTVDK SRWQQGNVFSCSVMHEALHNHYTQKSLSLSPG |
| hIgG1-LALA/YTE | 98 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPEAAGGPSVFLFPPK PKDTLYITREPEVTCVVVDVSHEDPEVKFNWYVDGVEVHNA KTKPREEQYNSTYRVVSVLTVLHQDWLNGKEYKCKVSNKAL PAPIEKTISKAKGQPREPQVYTLPPSRDELTKNQVSLTCLVKG FYPSDIAVEWESNGQPENNYKTTPPVLDSDGSFFLYSKLTVDK SRWQQGNVFSCSVMHEALHNHYTQKSLSLSPG |
| hIgG1-LAGA/YTE | 99 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPELAGAPSVFLFPPK PKDTLYITREPEVTCVVVDVSHEDPEVKFNWYVDGVEVHNA KTKPREEQYNSTYRVVSVLTVLHQDWLNGKEYKCKVSNKAL PAPIEKTISKAKGQPREPQVYTLPPSRDELTKNQVSLTCLVKG FYPSDIAVEWESNGQPENNYKTTPPVLDSDGSFFLYSKLTVDK SRWQQGNVFSCSVMHEALHNHYTQKSLSLSPG |
| hIgG1-LALAGA/YTE | 100 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPEAAGAPSVFLFPPK PKDTLYITREPEVTCVVVDVSHEDPEVKFNWYVDGVEVHNA KTKPREEQYNSTYRVVSVLTVLHQDWLNGKEYKCKVSNKAL PAPIEKTISKAKGQPREPQVYTLPPSRDELTKNQVSLTCLVKG FYPSDIAVEWESNGQPENNYKTTPPVLDSDGSFFLYSKLTVDK SRWQQGNVFSCSVMHEALHNHYTQKSLSLSPG |
| hIgG1-LALAPG/YTE | 101 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPEAAGGPSVFLFPPK PKDTLYITREPEVTCVVVDVSHEDPEVKFNWYVDGVEVHNA KTKPREEQYNSTYRVVSVLTVLHQDWLNGKEYKCKVSNKAL GAPIEKTISKAKGQPREPQVYTLPPSRDELTKNQVSLTCLVKG FYPSDIAVEWESNGQPENNYKTTPPVLDSDGSFFLYSKLTVDK SRWQQGNVFSCSVMHEALHNHYTQKSLSLSPG |
| hIgG1-LS (M428L/ N434S) | 102 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPELLGGPSVFLFPPK PKDTLMISRTPEVTCVVVDVSHEDPEVKFNWYVDGVEVHNA KTKPREEQYNSTYRVVSVLTVLHQDWLNGKEYKCKVSNKAL PAPIEKTISKAKGQPREPQVYTLPPSRDELTKNQVSLTCLVKG FYPSDIAVEWESNGQPENNYKTTPPVLDSDGSFFLYSKLTVDK SRWQQGNVFSCSVLHEALHSHYTQKSLSLSPG |
| hIgG1-N297A/LS | 103 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPELLGGPSVFLFPPK PKDTLMISRTPEVTCVVVDVSHEDPEVKFNWYVDGVEVHNA KTKPREEQYASTYRVVSVLTVLHQDWLNGKEYKCKVSNKAL PAPIEKTISKAKGQPREPQVYTLPPSRDELTKNQVSLTCLVKG FYPSDIAVEWESNGQPENNYKTTPPVLDSDGSFFLYSKLTVDK SRWQQGNVFSCSVLHEALHSHYTQKSLSLSPG |

TABLE 2-continued

Exemplary Fc Sequences

| Name | SEQ ID NO | Fc chain sequence |
|---|---|---|
| hIgG1-D265A/LS | 104 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVAVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPG |
| hIgG1-LALA/LS | 105 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPG |
| hIgG1-LAGA/LS | 106 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELAGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPG |
| hIgG1-LALAGA/LS | 107 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPG |
| hIgG1-LALAPG/LS | 108 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALGAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPG |
| hIgG1-DHS (L309D/Q311H/N434S) | 109 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVDHHDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHSHYTQKSLSLSPG |
| hIgG1-N297A/DHS | 110 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYASTYRVVSVLTVDHHDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHSHYTQKSLSLSPG |
| hIgG1-D265A/DHS | 111 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVAVSHEDPEVKFNWYVDGVEVHNAKTKPREEQYNSTYRVVSVLTVDHHDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHSHYTQKSLSLSPG |
| hIgG1-LALA/DHS | 112 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGGPSVFLFPPK |

TABLE 2-continued

| Exemplary Fc Sequences | | |
|---|---|---|
| Name | SEQ ID NO | Fc chain sequence |
| | | PKDTLMISRTPEVTCVVVDVSHEDPEVKFNWYVDGVEVHNA KTKPREEQYNSTYRVVSVLTVDHHDWLNGKEYKCKVSNKA LPAPIEKTISKAKGQPREPQVYTLPPSRDELTKNQVSLTCLVK GFYPSDIAVEWESNGQPENNYKTTPPVLDSDGSFFLYSKLTVD KSRWQQGNVFSCSVMHEALHSHYTQKSLSLSPG |
| hIgG1-LAGA/DHS | 113 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPELAGAPSVFLFPPK PKDTLMISRTPEVTCVVVDVSHEDPEVKFNWYVDGVEVHNA KTKPREEQYNSTYRVVSVLTVDHHDWLNGKEYKCKVSNKA LPAPIEKTISKAKGQPREPQVYTLPPSRDELTKNQVSLTCLVK GFYPSDIAVEWESNGQPENNYKTTPPVLDSDGSFFLYSKLTVD KSRWQQGNVFSCSVMHEALHSHYTQKSLSLSPG |
| hIgG1-LALAGA/DHS | 114 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPEAAGAPSVFLFPPK PKDTLMISRTPEVTCVVVDVSHEDPEVKFNWYVDGVEVHNA KTKPREEQYNSTYRVVSVLTVDHHDWLNGKEYKCKVSNKA LPAPIEKTISKAKGQPREPQVYTLPPSRDELTKNQVSLTCLVK GFYPSDIAVEWESNGQPENNYKTTPPVLDSDGSFFLYSKLTVD KSRWQQGNVFSCSVMHEALHSHYTQKSLSLSPG |
| hIgG1-LALAPG/DHS | 115 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPEAAGGPSVFLFPPK PKDTLMISRTPEVTCVVVDVSHEDPEVKFNWYVDGVEVHNA KTKPREEQYNSTYRVVSVLTVDHHDWLNGKEYKCKVSNKA LGAPIEKTISKAKGQPREPQVYTLPPSRDELTKNQVSLTCLVK GFYPSDIAVEWESNGQPENNYKTTPPVLDSDGSFFLYSKLTVD KSRWQQGNVFSCSVMHEALHSHYTQKSLSLSPG |
| hIgG4-YTE | 116 | ASTKGPSVFPLAPCSRSTSESTAALGCLVKDYFPEPVTVSWNS GALTSGVHTFPAVLQSSGLYSLSSVVTVPSSSLGTKTYTCNVD HKPSNTKVDKRVESKYGPPCPSCPAPEFLGGPSVFLFPPKPKD TLYITREPEVTCVVVDVSQEDPEVQFNWYVDGVEVHNAKTK PREEQFNSTYRVVSVLTVLHQDWLNGKEYKCKVSNKGLPSSI EKTISKAKGQPREPQVYTLPPSQEEMTKNQVSLTCLVKGFYPS DIAVEWESNGQPENNYKTTPPVLDSDGSFFLYSRLTVDKSRW QEGNVFSCSVMHEALHNHYTQKSLSLSLGK |
| hIgG4-SP/YTE | 117 | ASTKGPSVFPLAPCSRSTSESTAALGCLVKDYFPEPVTVSWNS GALTSGVHTFPAVLQSSGLYSLSSVVTVPSSSLGTKTYTCNVD HKPSNTKVDKRVESKYGPPCPPCPAPEFLGGPSVFLFPPKPKD TLYITREPEVTCVVVDVSQEDPEVQFNWYVDGVEVHNAKTK PREEQFNSTYRVVSVLTVLHQDWLNGKEYKCKVSNKGLPSSI EKTISKAKGQPREPQVYTLPPSQEEMTKNQVSLTCLVKGFYPS DIAVEWESNGQPENNYKTTPPVLDSDGSFFLYSRLTVDKSRW QEGNVFSCSVMHEALHNHYTQKSLSLSLGK |
| hIgG4-SPLE/YTE | 118 | ASTKGPSVFPLAPCSRSTSESTAALGCLVKDYFPEPVTVSWNS GALTSGVHTFPAVLQSSGLYSLSSVVTVPSSSLGTKTYTCNVD HKPSNTKVDKRVESKYGPPCPPCPAPEELGGPSVFLFPPKPKD TLYITREPEVTCVVVDVSQEDPEVQFNWYVDGVEVHNAKTK PREEQFNSTYRVVSVLTVLHQDWLNGKEYKCKVSNKGLPSSI EKTISKAKGQPREPQVYTLPPSQEEMTKNQVSLTCLVKGFYPS DIAVEWESNGQPENNYKTTPPVLDSDGSFFLYSRLTVDKSRW QEGNVFSCSVMHEALHNHYTQKSLSLSLGK |
| hIgG4-LS | 119 | ASTKGPSVFPLAPCSRSTSESTAALGCLVKDYFPEPVTVSWNS GALTSGVHTFPAVLQSSGLYSLSSVVTVPSSSLGTKTYTCNVD HKPSNTKVDKRVESKYGPPCPSCPAPEFLGGPSVFLFPPKPKD TLMISRTPEVTCVVVDVSQEDPEVQFNWYVDGVEVHNAKTK PREEQFNSTYRVVSVLTVLHQDWLNGKEYKCKVSNKGLPSSI EKTISKAKGQPREPQVYTLPPSQEEMTKNQVSLTCLVKGFYPS DIAVEWESNGQPENNYKTTPPVLDSDGSFFLYSRLTVDKSRW QEGNVFSCSVLHEALHSHYTQKSLSLSLGK |
| hIgG4-SP/LS | 120 | ASTKGPSVFPLAPCSRSTSESTAALGCLVKDYFPEPVTVSWNS GALTSGVHTFPAVLQSSGLYSLSSVVTVPSSSLGTKTYTCNVD HKPSNTKVDKRVESKYGPPCPPCPAPEFLGGPSVFLFPPKPKD TLMISRTPEVTCVVVDVSQEDPEVQFNWYVDGVEVHNAKTK PREEQFNSTYRVVSVLTVLHQDWLNGKEYKCKVSNKGLPSSI |

TABLE 2-continued

Exemplary Fc Sequences

| Name | SEQ ID NO | Fc chain sequence |
|---|---|---|
| | | EKTISKAKGQPREPQVYTLPPSQEEMTKNQVSLTCLVKGFYPS DIAVEWESNGQPENNYKTTPPVLDSDGSFFLYSRLTVDKSRW QEGNVFSCSVLHEALHSHYTQKSLSLSLGK |
| hIgG4-SPLE/LS | 121 | ASTKGPSVFPLAPCSRSTSESTAALGCLVKDYFPEPVTVSWNS GALTSGVHTFPAVLQSSGLYSLSSVVTVPSSSLGTKTYTCNVD HKPSNTKVDKRVESKYGPPCPPCPAPEELGGPSVFLFPPKPKD TLMISRTPEVTCVVVDVSQEDPEVQFNWYVDGVEVHNAKTK PREEQFNSTYRVVSVLTVLHQDWLNGKEYKCKVSNKGLPSSI EKTISKAKGQPREPQVYTLPPSQEEMTKNQVSLTCLVKGFYPS DIAVEWESNGQPENNYKTTPPVLDSDGSFFLYSRLTVDKSRW QEGNVFSCSVLHEALHSHYTQKSLSLSLGK |
| hIgG4-DHS | 122 | ASTKGPSVFPLAPCSRSTSESTAALGCLVKDYFPEPVTVSWNS GALTSGVHTFPAVLQSSGLYSLSSVVTVPSSSLGTKTYTCNVD HKPSNTKVDKRVESKYGPPCPSCPAPEFLGGPSVFLFPPKPKD TLMISRTPEVTCVVVDVSQEDPEVQFNWYVDGVEVHNAKTK PREEQFNSTYRVVSVLTVDHHDWLNGKEYKCKVSNKGLPSSI EKTISKAKGQPREPQVYTLPPSQEEMTKNQVSLTCLVKGFYPS DIAVEWESNGQPENNYKTTPPVLDSDGSFFLYSRLTVDKSRW QEGNVFSCSVMHEALHSHYTQKSLSLSLGK |
| hIgG4-SP/DHS | 123 | ASTKGPSVFPLAPCSRSTSESTAALGCLVKDYFPEPVTVSWNS GALTSGVHTFPAVLQSSGLYSLSSVVTVPSSSLGTKTYTCNVD HKPSNTKVDKRVESKYGPPCPPCPAPEFLGGPSVFLFPPKPKD TLMISRTPEVTCVVVDVSQEDPEVQFNWYVDGVEVHNAKTK PREEQFNSTYRVVSVLTVDHHDWLNGKEYKCKVSNKGLPSSI EKTISKAKGQPREPQVYTLPPSQEEMTKNQVSLTCLVKGFYPS DIAVEWESNGQPENNYKTTPPVLDSDGSFFLYSRLTVDKSRW QEGNVFSCSVMHEALHSHYTQKSLSLSLGK |
| hIgG4-SPLE/DHS | 124 | ASTKGPSVFPLAPCSRSTSESTAALGCLVKDYFPEPVTVSWNS GALTSGVHTFPAVLQSSGLYSLSSVVTVPSSSLGTKTYTCNVD HKPSNTKVDKRVESKYGPPCPPCPAPEELGGPSVFLFPPKPKD TLMISRTPEVTCVVVDVSQEDPEVQFNWYVDGVEVHNAKTK PREEQFNSTYRVVSVLTVDHHDWLNGKEYKCKVSNKGLPSSI EKTISKAKGQPREPQVYTLPPSQEEMTKNQVSLTCLVKGFYPS DIAVEWESNGQPENNYKTTPPVLDSDGSFFLYSRLTVDKSRW QEGNVFSCSVMHEALHSHYTQKSLSLSLGK |
| hIgG2-YTE | 125 | ASTKGPSVFPLAPCSRSTSESTAALGCLVKDYFPEPVTVSWNS GALTSGVHTFPAVLQSSGLYSLSSVVTVPSSNFGTQTYTCNVD HKPSNTKVDKTVERKCCVECPPCPAPPVAGPSVFLFPPKPKDT LYITREPEVTCVVVDVSHEDPEVQFNWYVDGVEVHNAKTKP REEQFNSTFRVVSVLTVVHQDWLNGKEYKCKVSNKGLPAPIE KTISKTKGQPREPQVYTLPPSREEMTKNQVSLTCLVKGFYPSD IAVEWESNGQPENNYKTTPPMLDSDGSFFLYSKLTVDKSRWQ QGNVFSCSVMHEALHNHYTQKSLSLSPG |
| hIgG2-LS | 126 | ASTKGPSVFPLAPCSRSTSESTAALGCLVKDYFPEPVTVSWNS GALTSGVHTFPAVLQSSGLYSLSSVVTVPSSNFGTQTYTCNVD HKPSNTKVDKTVERKCCVECPPCPAPPVAGPSVFLFPPKPKDT LMISRTPEVTCVVVDVSHEDPEVQFNWYVDGVEVHNAKTKP REEQFNSTFRVVSVLTVVHQDWLNGKEYKCKVSNKGLPAPIE KTISKTKGQPREPQVYTLPPSREEMTKNQVSLTCLVKGFYPSD IAVEWESNGQPENNYKTTPPMLDSDGSFFLYSKLTVDKSRWQ QGNVFSCSVLHEALHSHYTQKSLSLSPG |
| hIgG2-DHS | 127 | ASTKGPSVFPLAPCSRSTSESTAALGCLVKDYFPEPVTVSWNS GALTSGVHTFPAVLQSSGLYSLSSVVTVPSSNFGTQTYTCNVD HKPSNTKVDKTVERKCCVECPPCPAPPVAGPSVFLFPPKPKDT LMISRTPEVTCVVVDVSHEDPEVQFNWYVDGVEVHNAKTKP REEQFNSTFRVVSVLTVDHHDWLNGKEYKCKVSNKGLPAPIE KTISKTKGQPREPQVYTLPPSREEMTKNQVSLTCLVKGFYPSD IAVEWESNGQPENNYKTTPPMLDSDGSFFLYSKLTVDKSRWQ QGNVFSCSVMHEALHSHYTQKSLSLSPG |
| IgG4-SP | 128 | ASTKGPSVFPLAPCSRSTSESTAALGCLVKDYFPEPVTVSWNS GALTSGVHTFPAVLQSSGLYSLSSVVTVPSSSLGTKTYTCNVD HKPSNTKVDKRVESKYGPPCPPCPAPEFLGGPSVFLFPPKPKD TLMISRTPEVTCVVVDVSQEDPEVQFNWYVDGVEVHNAKTK PREEQFNSTYRVVSVLTVLHQDWLNGKEYKCKVSNKGLPSSI EKTISKAKGQPREPQVYTLPPSQEEMTKNQVSLTCLVKGFYPS DIAVEWESNGQPENNYKTTPPVLDSDGSFFLYSRLTVDKSRW QEGNVFSCSVMHEALHNHYTQKSLSLSLGK |

TABLE 2-continued

Exemplary Fc Sequences

| Name | SEQ ID NO | Fc chain sequence |
| --- | --- | --- |
| hIgG1-LA | 129 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPELLGGPSVFLFPPK PKDTLMISRTPEVTCVVVDVSHEDPEVKFNWYVDGVEVHNA KTKPREEQYNSTYRVVSVLTVLHQDWLNGKEYKCKVSNKAL PAPIEKTISKAKGQPREPQVYTLPPSRDELTKNQVSLTCLVKG FYPSDIAVEWESNGQPENNYKTTPPVLDSDGSFFLYSKLTVDK SRWQQGNVFSCSVLHEALHAHYTQKSLSLSPG |
| hIgG1-N297A/LA | 130 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPELLGGPSVFLFPPK PKDTLMISRTPEVTCVVVDVSHEDPEVKFNWYVDGVEVHNA KTKPREEQYASTYRVVSVLTVLHQDWLNGKEYKCKVSNKAL PAPIEKTISKAKGQPREPQVYTLPPSRDELTKNQVSLTCLVKG FYPSDIAVEWESNGQPENNYKTTPPVLDSDGSFFLYSKLTVDK SRWQQGNVFSCSVLHEALHAHYTQKSLSLSPG |
| hIgG1-D265A/LA | 131 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPELLGGPSVFLFPPK PKDTLMISRTPEVTCVVVAVSHEDPEVKFNWYVDGVEVHNA KTKPREEQYNSTYRVVSVLTVLHQDWLNGKEYKCKVSNKAL PAPIEKTISKAKGQPREPQVYTLPPSRDELTKNQVSLTCLVKG FYPSDIAVEWESNGQPENNYKTTPPVLDSDGSFFLYSKLTVDK SRWQQGNVFSCSVLHEALHAHYTQKSLSLSPG |
| hIgG1-LALA/LA | 132 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPEAAGGPSVFLFPPK PKDTLMISRTPEVTCVVVDVSHEDPEVKFNWYVDGVEVHNA KTKPREEQYNSTYRVVSVLTVLHQDWLNGKEYKCKVSNKAL PAPIEKTISKAKGQPREPQVYTLPPSRDELTKNQVSLTCLVKG FYPSDIAVEWESNGQPENNYKTTPPVLDSDGSFFLYSKLTVDK SRWQQGNVFSCSVLHEALHAHYTQKSLSLSPG |
| hIgG1-LAGA/LA | 133 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPELAGAPSVFLFPPK PKDTLMISRTPEVTCVVVDVSHEDPEVKFNWYVDGVEVHNA KTKPREEQYNSTYRVVSVLTVLHQDWLNGKEYKCKVSNKAL PAPIEKTISKAKGQPREPQVYTLPPSRDELTKNQVSLTCLVKG FYPSDIAVEWESNGQPENNYKTTPPVLDSDGSFFLYSKLTVDK SRWQQGNVFSCSVLHEALHAHYTQKSLSLSPG |
| hIgG1-LALAGA/LA | 134 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPEAAGAPSVFLFPPK PKDTLMISRTPEVTCVVVDVSHEDPEVKFNWYVDGVEVHNA KTKPREEQYNSTYRVVSVLTVLHQDWLNGKEYKCKVSNKAL PAPIEKTISKAKGQPREPQVYTLPPSRDELTKNQVSLTCLVKG FYPSDIAVEWESNGQPENNYKTTPPVLDSDGSFFLYSKLTVDK SRWQQGNVFSCSVLHEALHAHYTQKSLSLSPG |
| hIgG1-LALAPG/LA | 135 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPEAAGGPSVFLFPPK PKDTLMISRTPEVTCVVVDVSHEDPEVKFNWYVDGVEVHNA KTKPREEQYNSTYRVVSVLTVLHQDWLNGKEYKCKVSNKAL GAPIEKTISKAKGQPREPQVYTLPPSRDELTKNQVSLTCLVKG FYPSDIAVEWESNGQPENNYKTTPPVLDSDGSFFLYSKLTVDK SRWQQGNVFSCSVLHEALHAHYTQKSLSLSPG |
| hIgG1-N434A | 136 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPELLGGPSVFLFPPK PKDTLMISRTPEVTCVVVDVSHEDPEVKFNWYVDGVEVHNA KTKPREEQYNSTYRVVSVLTVLHQDWLNGKEYKCKVSNKAL PAPIEKTISKAKGQPREPQVYTLPPSRDELTKNQVSLTCLVKG FYPSDIAVEWESNGQPENNYKTTPPVLDSDGSFFLYSKLTVDK SRWQQGNVFSCSVMHEALHAHYTQKSLSLSPG |
| hIgG1-N297A/N434A | 137 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPELLGGPSVFLFPPK PKDTLMISRTPEVTCVVVDVSHEDPEVKFNWYVDGVEVHNA |

TABLE 2-continued

Exemplary Fc Sequences

| Name | SEQ ID NO | Fc chain sequence |
|---|---|---|
| | | KTKPREEQYASTYRVVSVLTVLHQDWLNGKEYKCKVSNKAL PAPIEKTISKAKGQPREPQVYTLPPSRDELTKNQVSLTCLVKG FYPSDIAVEWESNGQPENNYKTTPPVLDSDGSFFLYSKLTVDK SRWQQGNVFSCSVMHEALHAHYTQKSLSLSPG |
| hIgG1-D265A/N434A | 138 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPELLGGPSVFLFPPK PKDTLMISRTPEVTCVVVAVSHEDPEVKFNWYVDGVEVHNA KTKPREEQYNSTYRVVSVLTVLHQDWLNGKEYKCKVSNKAL PAPIEKTISKAKGQPREPQVYTLPPSRDELTKNQVSLTCLVKG FYPSDIAVEWESNGQPENNYKTTPPVLDSDGSFFLYSKLTVDK SRWQQGNVFSCSVMHEALHAHYTQKSLSLSPG |
| hIgG1-LALA/N434A | 139 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPEAAGGPSVFLFPPK PKDTLMISRTPEVTCVVVDVSHEDPEVKFNWYVDGVEVHNA KTKPREEQYNSTYRVVSVLTVLHQDWLNGKEYKCKVSNKAL PAPIEKTISKAKGQPREPQVYTLPPSRDELTKNQVSLTCLVKG FYPSDIAVEWESNGQPENNYKTTPPVLDSDGSFFLYSKLTVDK SRWQQGNVFSCSVMHEALHAHYTQKSLSLSPG |
| hIgG1-LAGA/N434A | 140 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPELAGAPSVFLFPPK PKDTLMISRTPEVTCVVVDVSHEDPEVKFNWYVDGVEVHNA KTKPREEQYNSTYRVVSVLTVLHQDWLNGKEYKCKVSNKAL PAPIEKTISKAKGQPREPQVYTLPPSRDELTKNQVSLTCLVKG FYPSDIAVEWESNGQPENNYKTTPPVLDSDGSFFLYSKLTVDK SRWQQGNVFSCSVMHEALHAHYTQKSLSLSPG |
| hIgG1-LALAGA/N434A | 141 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPEAAGAPSVFLFPPK PKDTLMISRTPEVTCVVVDVSHEDPEVKFNWYVDGVEVHNA KTKPREEQYNSTYRVVSVLTVLHQDWLNGKEYKCKVSNKAL PAPIEKTISKAKGQPREPQVYTLPPSRDELTKNQVSLTCLVKG FYPSDIAVEWESNGQPENNYKTTPPVLDSDGSFFLYSKLTVDK SRWQQGNVFSCSVMHEALHAHYTQKSLSLSPG |
| hIgG1-LALAPG/N434A | 142 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPEAAGGPSVFLFPPK PKDTLMISRTPEVTCVVVDVSHEDPEVKFNWYVDGVEVHNA KTKPREEQYNSTYRVVSVLTVLHQDWLNGKEYKCKVSNKAL GAPIEKTISKAKGQPREPQVYTLPPSRDELTKNQVSLTCLVKG FYPSDIAVEWESNGQPENNYKTTPPVLDSDGSFFLYSKLTVDK SRWQQGNVFSCSVMHEALHAHYTQKSLSLSPG |
| hIgG1-N434W | 143 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPELLGGPSVFLFPPK PKDTLMISRTPEVTCVVVDVSHEDPEVKFNWYVDGVEVHNA KTKPREEQYNSTYRVVSVLTVLHQDWLNGKEYKCKVSNKAL PAPIEKTISKAKGQPREPQVYTLPPSRDELTKNQVSLTCLVKG FYPSDIAVEWESNGQPENNYKTTPPVLDSDGSFFLYSKLTVDK SRWQQGNVFSCSVMHEALHWHYTQKSLSLSPG |
| hIgG1-N297A/N434W | 144 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPELLGGPSVFLFPPK PKDTLMISRTPEVTCVVVDVSHEDPEVKFNWYVDGVEVHNA KTKPREEQYASTYRVVSVLTVLHQDWLNGKEYKCKVSNKAL PAPIEKTISKAKGQPREPQVYTLPPSRDELTKNQVSLTCLVKG FYPSDIAVEWESNGQPENNYKTTPPVLDSDGSFFLYSKLTVDK SRWQQGNVFSCSVMHEALHWHYTQKSLSLSPG |
| hIgG1-D265A/N434W | 145 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPELLGGPSVFLFPPK PKDTLMISRTPEVTCVVVAVSHEDPEVKFNWYVDGVEVHNA KTKPREEQYNSTYRVVSVLTVLHQDWLNGKEYKCKVSNKAL PAPIEKTISKAKGQPREPQVYTLPPSRDELTKNQVSLTCLVKG FYPSDIAVEWESNGQPENNYKTTPPVLDSDGSFFLYSKLTVDK SRWQQGNVFSCSVMHEALHWHYTQKSLSLSPG |

TABLE 2-continued

| Exemplary Fc Sequences | | |
|---|---|---|
| Name | SEQ ID NO | Fc chain sequence |
| hIgG1-LALA/N434W | 146 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPEAAGGPSVFLFPPK PKDTLMISRTPEVTCVVVDVSHEDPEVKFNWYVDGVEVHNA KTKPREEQYNSTYRVVSVLTVLHQDWLNGKEYKCKVSNKAL PAPIEKTISKAKGQPREPQVYTLPPSRDELTKNQVSLTCLVKG FYPSDIAVEWESNGQPENNYKTTPPVLDSDGSFFLYSKLTVDK SRWQQGNVFSCSVMHEALHWHYTQKSLSLSPG |
| hIgG1-LAGA/N434W | 147 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPELAGAPSVFLFPPK PKDTLMISRTPEVTCVVVDVSHEDPEVKFNWYVDGVEVHNA KTKPREEQYNSTYRVVSVLTVLHQDWLNGKEYKCKVSNKAL PAPIEKTISKAKGQPREPQVYTLPPSRDELTKNQVSLTCLVKG FYPSDIAVEWESNGQPENNYKTTPPVLDSDGSFFLYSKLTVDK SRWQQGNVFSCSVMHEALHWHYTQKSLSLSPG |
| hIgG1-LALAGA/N434W | 148 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPEAAGAPSVFLFPPK PKDTLMISRTPEVTCVVVDVSHEDPEVKFNWYVDGVEVHNA KTKPREEQYNSTYRVVSVLTVLHQDWLNGKEYKCKVSNKAL PAPIEKTISKAKGQPREPQVYTLPPSRDELTKNQVSLTCLVKG FYPSDIAVEWESNGQPENNYKTTPPVLDSDGSFFLYSKLTVDK SRWQQGNVFSCSVMHEALHWHYTQKSLSLSPG |
| hIgG1-LALAPG/N434W | 149 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPEAAGGPSVFLFPPK PKDTLMISRTPEVTCVVVDVSHEDPEVKFNWYVDGVEVHNA KTKPREEQYNSTYRVVSVLTVLHQDWLNGKEYKCKVSNKAL GAPIEKTISKAKGQPREPQVYTLPPSRDELTKNQVSLTCLVKG FYPSDIAVEWESNGQPENNYKTTPPVLDSDGSFFLYSKLTVDK SRWQQGNVFSCSVMHEALHWHYTQKSLSLSPG |
| hIgG1/DQ (T256D/T307Q) | 150 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPELLGGPSVFLFPPK PKDTLMISRDPEVTCVVVDVSHEDPEVKFNWYVDGVEVHNA KTKPREEQYNSTYRVVSVLQVLHQDWLNGKEYKCKVSNKA LPAPIEKTISKAKGQPREPQVYTLPPSRDELTKNQVSLTCLVK GFYPSDIAVEWESNGQPENNYKTTPPVLDSDGSFFLYSKLTVD KSRWQQGNVFSCSVMHEALHNHYTQKSLSLSPG |
| hIgG1-N297A/DQ | 151 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPELLGGPSVFLFPPK PKDTLMISRDPEVTCVVVDVSHEDPEVKFNWYVDGVEVHNA KTKPREEQYASTYRVVSVLQVLHQDWLNGKEYKCKVSNKA LPAPIEKTISKAKGQPREPQVYTLPPSRDELTKNQVSLTCLVK GFYPSDIAVEWESNGQPENNYKTTPPVLDSDGSFFLYSKLTVD KSRWQQGNVFSCSVMHEALHNHYTQKSLSLSPG |
| hIgG1-D265A/DQ | 152 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPELLGGPSVFLFPPK PKDTLMISRDPEVTCVVVAVSHEDPEVKFNWYVDGVEVHNA KTKPREEQYNSTYRVVSVLQVLHQDWLNGKEYKCKVSNKA LPAPIEKTISKAKGQPREPQVYTLPPSRDELTKNQVSLTCLVK GFYPSDIAVEWESNGQPENNYKTTPPVLDSDGSFFLYSKLTVD KSRWQQGNVFSCSVMHEALHNHYTQKSLSLSPG |
| hIgG1-LALA/DQ | 153 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPEAAGGPSVFLFPPK PKDTLMISRDPEVTCVVVDVSHEDPEVKFNWYVDGVEVHNA KTKPREEQYNSTYRVVSVLQVLHQDWLNGKEYKCKVSNKA LPAPIEKTISKAKGQPREPQVYTLPPSRDELTKNQVSLTCLVK GFYPSDIAVEWESNGQPENNYKTTPPVLDSDGSFFLYSKLTVD KSRWQQGNVFSCSVMHEALHNHYTQKSLSLSPG |
| hIgG1-LAGA/DQ | 154 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPELAGAPSVFLFPPK |

TABLE 2-continued

Exemplary Fc Sequences

| Name | SEQ ID NO | Fc chain sequence |
|---|---|---|
| | | PKDTLMISRDPEVTCVVVDVSHEDPEVKFNWYVDGVEVHNA KTKPREEQYNSTYRVVSVLQVLHQDWLNGKEYKCKVSNKA LPAPIEKTISKAKGQPREPQVYTLPPSRDELTKNQVSLTCLVK GFYPSDIAVEWESNGQPENNYKTTPPVLDSDGSFFLYSKLTVD KSRWQQGNVFSCSVMHEALHNHYTQKSLSLSPG |
| hIgG1-LALAGA/DQ | 155 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPEAAGAPSVFLFPPK PKDTLMISRDPEVTCVVVDVSHEDPEVKFNWYVDGVEVHNA KTKPREEQYNSTYRVVSVLQVLHQDWLNGKEYKCKVSNKA LPAPIEKTISKAKGQPREPQVYTLPPSRDELTKNQVSLTCLVK GFYPSDIAVEWESNGQPENNYKTTPPVLDSDGSFFLYSKLTVD KSRWQQGNVFSCSVMHEALHNHYTQKSLSLSPG |
| hIgG1-LALAPG/DQ | 156 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPEAAGGPSVFLFPPK PKDTLMISRDPEVTCVVVDVSHEDPEVKFNWYVDGVEVHNA KTKPREEQYNSTYRVVSVLQVLHQDWLNGKEYKCKVSNKA LGAPIEKTISKAKGQPREPQVYTLPPSRDELTKNQVSLTCLVK GFYPSDIAVEWESNGQPENNYKTTPPVLDSDGSFFLYSKLTVD KSRWQQGNVFSCSVMHEALHNHYTQKSLSLSPG |
| hIgG1/DW (T256D/ T307W) | 157 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPELLGGPSVFLFPPK PKDTLMISRDPEVTCVVVDVSHEDPEVKFNWYVDGVEVHNA KTKPREEQYNSTYRVVSVLWVLHQDWLNGKEYKCKVSNKA LPAPIEKTISKAKGQPREPQVYTLPPSRDELTKNQVSLTCLVK GFYPSDIAVEWESNGQPENNYKTTPPVLDSDGSFFLYSKLTVD KSRWQQGNVFSCSVMHEALHNHYTQKSLSLSPG |
| hIgG1-N297A/DW | 158 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPELLGGPSVFLFPPK PKDTLMISRDPEVTCVVVDVSHEDPEVKFNWYVDGVEVHNA KTKPREEQYASTYRVVSVLWVLHQDWLNGKEYKCKVSNKA LPAPIEKTISKAKGQPREPQVYTLPPSRDELTKNQVSLTCLVK GFYPSDIAVEWESNGQPENNYKTTPPVLDSDGSFFLYSKLTVD KSRWQQGNVFSCSVMHEALHNHYTQKSLSLSPG |
| hIgG1-D265A/DW | 159 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPELLGGPSVFLFPPK PKDTLMISRDPEVTCVVVAVSHEDPEVKFNWYVDGVEVHNA KTKPREEQYNSTYRVVSVLWVLHQDWLNGKEYKCKVSNKA LPAPIEKTISKAKGQPREPQVYTLPPSRDELTKNQVSLTCLVK GFYPSDIAVEWESNGQPENNYKTTPPVLDSDGSFFLYSKLTVD KSRWQQGNVFSCSVMHEALHNHYTQKSLSLSPG |
| hIgG1-LALA/DW | 160 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPEAAGGPSVFLFPPK PKDTLMISRDPEVTCVVVDVSHEDPEVKFNWYVDGVEVHNA KTKPREEQYNSTYRVVSVLWVLHQDWLNGKEYKCKVSNKA LPAPIEKTISKAKGQPREPQVYTLPPSRDELTKNQVSLTCLVK GFYPSDIAVEWESNGQPENNYKTTPPVLDSDGSFFLYSKLTVD KSRWQQGNVFSCSVMHEALHNHYTQKSLSLSPG |
| hIgG1-LAGA/DW | 161 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPELAGAPSVFLFPPK PKDTLMISRDPEVTCVVVDVSHEDPEVKFNWYVDGVEVHNA KTKPREEQYNSTYRVVSVLWVLHQDWLNGKEYKCKVSNKA LPAPIEKTISKAKGQPREPQVYTLPPSRDELTKNQVSLTCLVK GFYPSDIAVEWESNGQPENNYKTTPPVLDSDGSFFLYSKLTVD KSRWQQGNVFSCSVMHEALHNHYTQKSLSLSPG |
| hIgG1-LALAGA/DW | 162 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPEAAGAPSVFLFPPK PKDTLMISRDPEVTCVVVDVSHEDPEVKFNWYVDGVEVHNA KTKPREEQYNSTYRVVSVLWVLHQDWLNGKEYKCKVSNKA |

TABLE 2-continued

Exemplary Fc Sequences

| Name | SEQ ID NO | Fc chain sequence |
|---|---|---|
| | | LPAPIEKTISKAKGQPREPQVYTLPPSRDELTKNQVSLTCLVK GFYPSDIAVEWESNGQPENNYKTTPPVLDSDGSFFLYSKLTVD KSRWQQGNVFSCSVMHEALHNHYTQKSLSLSPG |
| hIgG1-LALAPG/DW | 163 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPEAAGGPSVFLFPPK PKDTLMISRDPEVTCVVVDVSHEDPEVKFNWYVDGVEVHNA KTKPREEQYNSTYRVVSVLWVLHQDWLNGKEYKCKVSNKA LGAPIEKTISKAKGQPREPQVYTLPPSRDELTKNQVSLTCLVK GFYPSDIAVEWESNGQPENNYKTTPPVLDSDGSFFLYSKLTVD KSRWQQGNVFSCSVMHEALHNHYTQKSLSLSPG |
| hIgG1/YD (M252Y/T256D) | 164 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPELLGGPSVFLFPPK PKDTLYISRDPEVTCVVVDVSHEDPEVKFNWYVDGVEVHNA KTKPREEQYNSTYRVVSVLTVLHQDWLNGKEYKCKVSNKAL PAPIEKTISKAKGQPREPQVYTLPPSRDELTKNQVSLTCLVKG FYPSDIAVEWESNGQPENNYKTTPPVLDSDGSFFLYSKLTVDK SRWQQGNVFSCSVMHEALHNHYTQKSLSLSPG |
| hIgG1-N297A/YD | 165 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPELLGGPSVFLFPPK PKDTLYISRDPEVTCVVVDVSHEDPEVKFNWYVDGVEVHNA KTKPREEQYASTYRVVSVLTVLHQDWLNGKEYKCKVSNKAL PAPIEKTISKAKGQPREPQVYTLPPSRDELTKNQVSLTCLVKG FYPSDIAVEWESNGQPENNYKTTPPVLDSDGSFFLYSKLTVDK SRWQQGNVFSCSVMHEALHNHYTQKSLSLSPG |
| hIgG1-D265A/YD | 166 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPELLGGPSVFLFPPK PKDTLYISRDPEVTCVVVAVSHEDPEVKFNWYVDGVEVHNA KTKPREEQYNSTYRVVSVLTVLHQDWLNGKEYKCKVSNKAL PAPIEKTISKAKGQPREPQVYTLPPSRDELTKNQVSLTCLVKG FYPSDIAVEWESNGQPENNYKTTPPVLDSDGSFFLYSKLTVDK SRWQQGNVFSCSVMHEALHNHYTQKSLSLSPG |
| hIgG1-LALA/YD | 167 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPEAAGGPSVFLFPPK PKDTLYISRDPEVTCVVVDVSHEDPEVKFNWYVDGVEVHNA KTKPREEQYNSTYRVVSVLTVLHQDWLNGKEYKCKVSNKAL PAPIEKTISKAKGQPREPQVYTLPPSRDELTKNQVSLTCLVKG FYPSDIAVEWESNGQPENNYKTTPPVLDSDGSFFLYSKLTVDK SRWQQGNVFSCSVMHEALHNHYTQKSLSLSPG |
| hIgG1-LAGA/YD | 168 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPELAGAPSVFLFPPK PKDTLYISRDPEVTCVVVDVSHEDPEVKFNWYVDGVEVHNA KTKPREEQYNSTYRVVSVLTVLHQDWLNGKEYKCKVSNKAL PAPIEKTISKAKGQPREPQVYTLPPSRDELTKNQVSLTCLVKG FYPSDIAVEWESNGQPENNYKTTPPVLDSDGSFFLYSKLTVDK SRWQQGNVFSCSVMHEALHNHYTQKSLSLSPG |
| hIgG1-LALAGA/YD | 169 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPEAAGAPSVFLFPPK PKDTLYISRDPEVTCVVVDVSHEDPEVKFNWYVDGVEVHNA KTKPREEQYNSTYRVVSVLTVLHQDWLNGKEYKCKVSNKAL PAPIEKTISKAKGQPREPQVYTLPPSRDELTKNQVSLTCLVKG FYPSDIAVEWESNGQPENNYKTTPPVLDSDGSFFLYSKLTVDK SRWQQGNVFSCSVMHEALHNHYTQKSLSLSPG |
| hIgG1-LALAPG/YD | 170 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPEAAGGPSVFLFPPK PKDTLYISRDPEVTCVVVDVSHEDPEVKFNWYVDGVEVHNA KTKPREEQYNSTYRVVSVLTVLHQDWLNGKEYKCKVSNKAL GAPIEKTISKAKGQPREPQVYTLPPSRDELTKNQVSLTCLVKG FYPSDIAVEWESNGQPENNYKTTPPVLDSDGSFFLYSKLTVDK SRWQQGNVFSCSVMHEALHNHYTQKSLSLSPG |

TABLE 2-continued

Exemplary Fc Sequences

| Name | SEQ ID NO | Fc chain sequence |
|---|---|---|
| hIgG1/QVV (T307Q/ Q311V/ A378V) | 171 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPELLGGPSVFLFPPK PKDTLMISRTPEVTCVVVDVSHEDPEVKFNWYVDGVEVHNA KTKPREEQYNSTYRVVSVLQVLHVDWLNGKEYKCKVSNKA LPAPIEKTISKAKGQPREPQVYTLPPSRDELTKNQVSLTCLVK GFYPSDIVVEWESNGQPENNYKTTPPVLDSDGSFFLYSKLTVD KSRWQQGNVFSCSVMHEALHNHYTQKSLSLSPG |
| hIgG1- N297A/ QVV | 172 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPELLGGPSVFLFPPK PKDTLMISRTPEVTCVVVDVSHEDPEVKFNWYVDGVEVHNA KTKPREEQYASTYRVVSVLQVLHVDWLNGKEYKCKVSNKA LPAPIEKTISKAKGQPREPQVYTLPPSRDELTKNQVSLTCLVK GFYPSDIVVEWESNGQPENNYKTTPPVLDSDGSFFLYSKLTVD KSRWQQGNVFSCSVMHEALHNHYTQKSLSLSPG |
| hIgG1- D265A/ QVV | 173 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPELLGGPSVFLFPPK PKDTLMISRTPEVTCVVVAVSHEDPEVKFNWYVDGVEVHNA KTKPREEQYNSTYRVVSVLQVLHVDWLNGKEYKCKVSNKA LPAPIEKTISKAKGQPREPQVYTLPPSRDELTKNQVSLTCLVK GFYPSDIVVEWESNGQPENNYKTTPPVLDSDGSFFLYSKLTVD KSRWQQGNVFSCSVMHEALHNHYTQKSLSLSPG |
| hIgG1- LALA/QVV | 174 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPEAAGGPSVFLFPPK PKDTLMISRTPEVTCVVVDVSHEDPEVKFNWYVDGVEVHNA KTKPREEQYNSTYRVVSVLQVLHVDWLNGKEYKCKVSNKA LPAPIEKTISKAKGQPREPQVYTLPPSRDELTKNQVSLTCLVK GFYPSDIVVEWESNGQPENNYKTTPPVLDSDGSFFLYSKLTVD KSRWQQGNVFSCSVMHEALHNHYTQKSLSLSPG |
| hIgG1- LAGA/QVV | 175 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPELAGAPSVFLFPPK PKDTLMISRTPEVTCVVVDVSHEDPEVKFNWYVDGVEVHNA KTKPREEQYNSTYRVVSVLQVLHVDWLNGKEYKCKVSNKA LPAPIEKTISKAKGQPREPQVYTLPPSRDELTKNQVSLTCLVK GFYPSDIVVEWESNGQPENNYKTTPPVLDSDGSFFLYSKLTVD KSRWQQGNVFSCSVMHEALHNHYTQKSLSLSPG |
| hIgG1- LALAGA/ QVV | 176 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPEAAGAPSVFLFPPK PKDTLMISRTPEVTCVVVDVSHEDPEVKFNWYVDGVEVHNA KTKPREEQYNSTYRVVSVLQVLHVDWLNGKEYKCKVSNKA LPAPIEKTISKAKGQPREPQVYTLPPSRDELTKNQVSLTCLVK GFYPSDIVVEWESNGQPENNYKTTPPVLDSDGSFFLYSKLTVD KSRWQQGNVFSCSVMHEALHNHYTQKSLSLSPG |
| hIgG1- LALAPG/ QVV | 177 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPEAAGGPSVFLFPPK PKDTLMISRTPEVTCVVVDVSHEDPEVKFNWYVDGVEVHNA KTKPREEQYNSTYRVVSVLQVLHVDWLNGKEYKCKVSNKA LGAPIEKTISKAKGQPREPQVYTLPPSRDELTKNQVSLTCLVK GFYPSDIVVEWESNGQPENNYKTTPPVLDSDGSFFLYSKLTVD KSRWQQGNVFSCSVMHEALHNHYTQKSLSLSPG |
| hIgG1/ DDRVV (T256D/ N286D/ T307R/ Q311V/ A378V) | 178 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPELLGGPSVFLFPPK PKDTLMISRDPEVTCVVVDVSHEDPEVKFNWYVDGVEVDNA KTKPREEQYNSTYRVVSVLRVLHVDWLNGKEYKCKVSNKA LPAPIEKTISKAKGQPREPQVYTLPPSRDELTKNQVSLTCLVK GFYPSDIVVEWESNGQPENNYKTTPPVLDSDGSFFLYSKLTVD KSRWQQGNVFSCSVMHEALHNHYTQKSLSLSPG |
| hIgG1- N297A/ DDRVV | 179 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPELLGGPSVFLFPPK PKDTLMISRDPEVTCVVVDVSHEDPEVKFNWYVDGVEVDNA |

TABLE 2-continued

Exemplary Fc Sequences

| Name | SEQ ID NO | Fc chain sequence |
|---|---|---|
| | | KTKPREEQYASTYRVVSVLRVLHVDWLNGKEYKCKVSNKA LPAPIEKTISKAKGQPREPQVYTLPPSRDELTKNQVSLTCLVK GFYPSDIVVEWESNGQPENNYKTTPPVLDSDGSFFLYSKLTVD KSRWQQGNVFSCSVMHEALHNHYTQKSLSLSPG |
| hIgG1-D265A/DDRVV | 180 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPELLGGPSVFLFPPK PKDTLMISRDPEVTCVVVAVSHEDPEVKFNWYVDGVEVDNA KTKPREEQYNSTYRVVSVLRVLHVDWLNGKEYKCKVSNKA LPAPIEKTISKAKGQPREPQVYTLPPSRDELTKNQVSLTCLVK GFYPSDIVVEWESNGQPENNYKTTPPVLDSDGSFFLYSKLTVD KSRWQQGNVFSCSVMHEALHNHYTQKSLSLSPG |
| hIgG1-LALA/DDRVV | 181 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPEAAGGPSVFLFPPK PKDTLMISRDPEVTCVVVDVSHEDPEVKENWYVDGVEVDNA KTKPREEQYNSTYRVVSVLRVLHVDWLNGKEYKCKVSNKA LPAPIEKTISKAKGQPREPQVYTLPPSRDELTKNQVSLTCLVK GFYPSDIVVEWESNGQPENNYKTTPPVLDSDGSFFLYSKLTVD KSRWQQGNVFSCSVMHEALHNHYTQKSLSLSPG |
| hIgG1-LAGA/DDRVV | 182 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPELAGAPSVFLFPPK PKDTLMISRDPEVTCVVVDVSHEDPEVKFNWYVDGVEVDNA KTKPREEQYNSTYRVVSVLRVLHVDWLNGKEYKCKVSNKA LPAPIEKTISKAKGQPREPQVYTLPPSRDELTKNQVSLTCLVK GFYPSDIVVEWESNGQPENNYKTTPPVLDSDGSFFLYSKLTVD KSRWQQGNVFSCSVMHEALHNHYTQKSLSLSPG |
| hIgG1-LALAGA/DDRVV | 183 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPEAAGAPSVFLFPPK PKDTLMISRDPEVTCVVVDVSHEDPEVKFNWYVDGVEVDNA KTKPREEQYNSTYRVVSVLRVLHVDWLNGKEYKCKVSNKA LPAPIEKTISKAKGQPREPQVYTLPPSRDELTKNQVSLTCLVK GFYPSDIVVEWESNGQPENNYKTTPPVLDSDGSFFLYSKLTVD KSRWQQGNVFSCSVMHEALHNHYTQKSLSLSPG |
| hIgG1-LALAPG/DDRVV | 184 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPEAAGGPSVFLFPPK PKDTLMISRDPEVTCVVVDVSHEDPEVKFNWYVDGVEVDNA KTKPREEQYNSTYRVVSVLRVLHVDWLNGKEYKCKVSNKA LGAPIEKTISKAKGQPREPQVYTLPPSRDELTKNQVSLTCLVK GFYPSDIVVEWESNGQPENNYKTTPPVLDSDGSFFLYSKLTVD KSRWQQGNVFSCSVMHEALHNHYTQKSLSLSPG |
| hIgG1-Q311R/M428L | 185 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPELLGGPSVFLFPPK PKDTLMISRTPEVTCVVVDVSHEDPEVKFNWYVDGVEVHNA KTKPREEQYNSTYRVVSVLTVLHRDWLNGKEYKCKVSNKAL PAPIEKTISKAKGQPREPQVYTLPPSRDELTKNQVSLTCLVKG FYPSDIAVEWESNGQPENNYKTTPPVLDSDGSFFLYSKLTVDK SRWQQGNVFSCSVLHEALHNHYTQKSLSLSPG |
| hIgG4-Q311R/M428L | 186 | ASTKGPSVFPLAPCSRSTSESTAALGCLVKDYFPEPVTVSWNS GALTSGVHTFPAVLQSSGLYSLSSVVTVPSSSLGTKTYTCNVD HKPSNTKVDKRVESKYGPPCPSCPAPEFLGGPSVFLFPPKPKD TLMISRTPEVTCVVVDVSQEDPEVQFNWYVDGVEVHNAKTK PREEQFNSTYRVVSVLTVLHRDWLNGKEYKCKVSNKGLPSSI EKTISKAKGQPREPQVYTLPPSQEEMTKNQVSLTCLVKGFYPS DIAVEWESNGQPENNYKTTPPVLDSDGSFFLYSRLTVDKSRW QEGNVFSCSVLHEALHNHYTQKSLSLSLGK |
| IgG4-SP/Q311R/M428L | 187 | ASTKGPSVFPLAPCSRSTSESTAALGCLVKDYFPEPVTVSWNS GALTSGVHTFPAVLQSSGLYSLSSVVTVPSSSLGTKTYTCNVD HKPSNTKVDKRVESKYGPPCPPCPAPEFLGGPSVFLFPPKPKD TLMISRTPEVTCVVVDVSQEDPEVQFNWYVDGVEVHNAKTK PREEQFNSTYRVVSVLTVLHRDWLNGKEYKCKVSNKGLPSSI EKTISKAKGQPREPQVYTLPPSQEEMTKNQVSLTCLVKGFYPS DIAVEWESNGQPENNYKTTPPVLDSDGSFFLYSRLTVDKSRW QEGNVFSCSVLHEALHNHYTQKSLSLSLGK |

TABLE 2-continued

| Exemplary Fc Sequences | | |
|---|---|---|
| Name | SEQ ID NO | Fc chain sequence |
| IgG4-SPLE/Q311R/M428L | 188 | ASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEELGGPSVFLFPPKPKDTLMISRTPEVTCVVVDVSQEDPEVQFNWYVDGVEVHNAKTKPREEQFNSTYRVVSVLTVLHRDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVLHEALHNHYTQKSLSLSLGK |
| IgG2-Q311R/M428L | 189 | ASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTVERKCCVECPPCPAPPVAGPSVFLFPPKPKDTLMISRTPEVTCVVVDVSHEDPEVQFNWYVDGVEVHNAKTKPREEQFNSTFRVVSVLTVVHRDWLNGKEYKCKVSNKGLPAPIEKTISKTKGQPREPQVYTLPPSREEMTKNQVSLTCLVKGFYPSDIAVEWESNGQPENNYKTTPPMLDSDGSFFLYSKLTVDKSRWQQGNVFSCSVLHEALHNHYTQKSLSLSP |
| hIgG1-N297A/Q311R/M428L | 190 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYASTYRVVSVLTVLHRDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHNHYTQKSLSLSPG |
| hIgG1-D265A/Q311R/M428L | 191 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVAVSHEDPEVKFNWYVDGVEVHNAKTKPREEQYNSTYRVVSVLTVLHRDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHNHYTQKSLSLSPG |
| hIgG1-LALA/Q311R/M428L | 192 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHRDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHNHYTQKSLSLSPG |
| hIgG1-LAGA/Q311R/M428L | 193 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELAGAPSVFLFPPKPKDTLMISRTPEVTCVVVDVSHEDPEVKFNWYVDGVEVHNAKTKPREEQYNSTYRVVSVLTVLHRDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHNHYTQKSLSLSPG |
| hIgG1-LALAGA/Q311R/M428L | 194 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGAPSVFLFPPKPKDTLMISRTPEVTCVVVDVSHEDPEVKFNWYVDGVEVHNAKTKPREEQYNSTYRVVSVLTVLHRDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHNHYTQKSLSLSPG |
| hIgG1-LALAPG/Q311R/M428L | 195 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHRDWLNGKEYKCKVSNKALGAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHNHYTQKSLSLSPG |

In some embodiments, one or more modifications in the modified Fc region is selected from the group consisting of: S298A, E333A, K334A, K326A, F243L, R292P, Y300L, V305I, P396L, F243L, R292P, Y300L, L235V, P396L, F243L, S239D, 1332E, A330L, S267E, L328F, D265S, S239E, K326A, A327H, G237F, K326E, G236A, D270L, H268D, S324T, L234F, N325L, V266L, and S267D. In some embodiments, one or more modifications in the modified Fc region are selected from the group consisting of S228P, M252Y, S254T, T256E, T256D, T250Q, H285D, T307A, T307Q, T307R, T307W, L309D, Q411H, Q311V, A378V, E380A, M428L, N434A, N434S, N297A, D265A, L234A, L235A, and N434W.

In some embodiments, the modified Fc region comprises a specific combination of amino acid substitutions selected from the group consisting of: L234A/L235A; V234A/G237A; L235A/G237A/E318A; S228P/L236E; H268Q/V309L/A330S/A331S; C220S/C226S/C229S/P238S; C226S/C229S/E3233P/L235V/L235A; L234F/L235E/P331S; C226S/P230S; L234A/G237A; L234A/L235A/G237A; Q311R/M428L; and L234A/L235A/P329G.

In some embodiments, the modified Fc region comprises a specific combination of amino acid substitutions selected from the group consisting of M428L/N434S (LS); M252Y/S254T/T256E (YTE); T250Q/M428L; T307A/E380A/N434A; T256D/T307Q (DQ); T256D/T307W (DW); M252Y/T256D (YD); T307Q/Q311V/A378V (QVV); T256D/H285D/T307R/Q311V/A378V (DDRVV); L309D/Q311H/N434S (DHS); S228P/L235E (SPLE); L234A/L235A (LALA); M428L/N434A (LA); L234A/G237A (LAGA); L234A/L235A/G237A (LALAGA); L234A/L235A/P329G (LALAPG); H433K/N434F (KF); N297A/YTE; D265A/YTE; LALA/YTE; LAGA/YTE; LALAGA/YTE; LALAPG/YTE; N297A/LS; D265A/LS; LALA/LS; LAGA/LS; LALAGA/LS; LALAPG/LS; N297A/DHS; D265A/DHS; LALA/DHS; LAGA/DHS; LALAGA/DHS; LALAPG/DHS; SP/YTE; SPLE/YTE; SP/LS; SPLE/LS; SP/DHS; SPLE/DHS; N297A/LA; D265A/LA; LALA/LA; LAGA/LA; LALAGA/LA; LALAPG/LA; N297A/N434A; D265A/N434A; LALA/N434A; LAGA/N434A; LALAGA/N434A; LALAPG/N434A; N297A/N434W; D265A/N434W; LALA/N434W; LAGA/N434W; LALAGA/N434W; LALAPG/N434W; N297A/DQ; D265A/DQ; LALA/DQ; LAGA/DQ; LALAGA/DQ; LALAPG/DQ; N297A/DW; D265A/DW; LALA/DW; LAGA/DW; LALAGA/DW; LALAPG/DW; N297A/YD; D265A/YD; LALA/YD; LAGA/YD; LALAGA/YD; LALAPG/YD; N297A/QVV; D265A/QVV; LALA/QVV; LAGA/QVV, LALAGA/QVV; LALAPG/QVV; N297A/DDRVV; D265A/DDRVV; LALA/DDRVV; LAGA/DDRVV; LALAGA/DDRVV; LALAPG/DDRVV; SP/Q311R/M428L; SPLE/Q311R/M428L; N297A/Q311R/M428L; D265A/Q311R/M428L; LALA/Q311R/M428L; LAGA/Q311R/M428L; LALAGA/Q311R/M428L; and LALAPG/Q311R/M428L. In some embodiments, the modified Fc region comprises a specific combination of amino acid substitutions selected from the group consisting of M428L/N434S (LS), M252Y/S254T/T256E (YTE), M428L/N434A (LA), H433K/N434F (KF), and L309D/Q311H/N434S (DHS). In some embodiments, the modified Fc region comprises M428L/N434S (LS) modifications. In some embodiments, the modified Fc region comprises M252Y/S254T/T256E (YTE) modifications (EU numbering).

In some embodiments, provided binding proteins include modifications to improve its ability to mediate effector function. Such modifications are known in the art and include afucosylation, or engineering of the affinity of the Fc region towards an activating receptor, mainly FcγRIIIa for antibody-dependent cellular cytotoxicity (ADCC), and towards C1q for complement-dependent cytotoxicity (CDC).

In some aspects, provided binding proteins comprise an Fc region (e.g., an IgG1 Fc region) with reduced fucose content at position Asn 297 (EU numbering) compared to a naturally occurring Fc region. Such Fc regions are known to have improved ADCC. In some aspects, such antibodies do not comprise any fucose at position Asn 297.

In some embodiments, provided binding proteins comprise an Fc region with one or more amino acid substitutions which improve ADCC, such as a substitution at one or more of positions 298, 333, and 334 of the Fc region. In some embodiments, provided binding proteins comprise an Fc region with one or more amino acid substitutions at positions 239, 332, and 330.

In some embodiments, the Fc region comprises an amino acid sequence having at least 80%, at least 85%, at least 90%, at least 92.5%, at least 95%, at least 96%, at least 97%, at least 98%, or at least 99% sequence identity with the amino acid sequence according to any one of SEQ ID NOs: 84-195.

In some embodiments, the binding protein comprises an Fc region comprising a human IgG sequence which lacks the C-terminal G446 (according to Kabat) of any of SEQ ID NOs: 84, 86, 89-115, 125-127, 129-185, and 190-195, but is otherwise identical to one of the aforesaid sequences.

Although a C-terminal lysine may be present in the corresponding coding sequence of the constant heavy chain region (e.g., in a sequence such as SEQ ID NO: 85), it may be cleaved off during manufacture or after administration (resulting in, e.g., a constant heavy chain sequence lacking the C-terminal lysine). Accordingly, any of the binding proteins described above may comprise a human IgG sequence containing a C-terminal lysine, a human IgG sequence lacking a C-terminal lysine, or a mixture thereof (e.g., a mixture of the same heavy chain constant sequence with and without a C-terminal lysine).

In some embodiments, provided binding proteins comprise an Fc region with at least one galactose residue in the oligosaccharide attached to the Fc region. Such antibody variants may have improved CDC function.

In some embodiments, provided binding proteins comprise one or more alterations that improve or diminish C1q binding and/or CDC.

In certain embodiments, the Fc region comprises one or more amino acid substitutions, wherein the one or more substitutions result in an increase in one or more of antibody half-life, ADCC activity, ADCP activity, or CDC activity compared with the Fc without the one or more substitutions. In certain embodiments, the one or more amino acid substitutions result in increased antibody half-life at pH 6.0 compared to a binding protein comprising a wild-type Fc region. In certain embodiments, the binding protein has an increased half-life that is about 10,000-fold, 1,000-fold, 500-fold, 100-fold, 50-fold, 20-fold, 10-fold, 9-fold, 8-fold, 7-fold, 6-fold, 5-fold, 4.5-fold, 4-fold, 3.5-fold, 3-fold, 2.5-fold, 2-fold, 1.95-fold, 1.9-fold, 1.85-fold, 1.8-fold, 1.75-fold, 1.7-fold, 1.65-fold, 1.6-fold, 1.55-fold, 1.50-fold, 1.45-fold, 1.4-fold, 1.35-fold, 1.3-fold, 1.25-fold, 1.2-fold, 1.15-fold, 1.1-fold, or 1.05-fold longer compared to a binding protein comprising a wild-type Fc region.

In certain embodiments, the Fc region comprises one or more amino acid substitutions, wherein the one or more substitutions result in a decrease in one or more of ADCC activity, ADCP activity, or CDC activity compared with the Fc without the one or more substitutions.

In certain embodiments, the Fc region binds an Fcγ Receptor selected from the group consisting of. FcγRI, FcγRIIa, FcγRIIb, FcγRIIc, FcγRIIIa, and FcγRIIIb. In certain embodiments, the Fc region binds an Fcγ Receptor with higher affinity at pH 6.0 compared to a binding protein comprising a wild-type Fc region.

In some embodiments, provided binding proteins comprise an extended half-life (i.e., serum half-life), e.g., in human serum or in humans. In some embodiments, provided binding proteins comprise a half-life of at least about 14, 28, 42, 56, 70, 84, 96, or more than 96 days. In some embodiments, provided binding proteins comprise a half-life in a range of about 14 days to about 96 days, about 14 days to about 84 days, about 14 days to about 70 days, about 14 days to about 56 days, about 14 days to about 42 days, about 14 days to about 28 days, of about 28 days to about 96 days, about 28 days to about 84 days, about 28 days to about 70 days, about 28 days to about 56 days, about 28 days to about 42 days, of about 42 days to about 96 days, about 42 days to about 84 days, about 42 days to about 70 days, or about 42 days to about 56 days. In some embodiments, provided binding proteins comprise a half-life of at least about 50 days, at least about 55 days, at least about 60 days, at least about 65 days, at least about 70 days, at least about 75 days, at least about 80 days, at least about 85 days, or at least about 90 days. In some embodiments, the provided binding proteins comprise a half-life of about 50 days, about 55 days, about 60 days, about 65 days, about 70 days, about 75 days, about 80 days, about 85 days, or about 90 days. Methods of measuring half-life are known in the art. In some embodiments, the half-life is measured in a non-human primate. In some embodiments, the half-life is measured in a human. In some embodiments, the half-life is measured following intravenous administration. In some embodiments, the half-life is measured following subcutaneous administration.

In some embodiments, provided binding proteins have a half-life that is at least 20% longer than a comparator antibody. In some embodiments, the comparator antibody comprises the same complementarity determining regions and variable regions but different Fc regions, or a comparator antibody which is bivalent and monospecific but has the same complementarity determining regions and variable regions. In some embodiments, the comparator antibody comprises different CDRs and/or different variable regions, in addition to different Fc region sequences, from the binding proteins provided herein. In some embodiments, the half-life of provided binding proteins is at least 30%, at least 40%, at least 50%, at least 60%, at least 70%, at least 80%, or at least 90% longer than the half-life of the comparator antibody. In some embodiments, the half-life of provided binding proteins is longer than the half-life of the comparator antibody by at least 2 fold, at least 3 fold, at least 4 fold, at least 5 fold, at least 6 fold, at least 7 fold, at least 8 fold, at least 9 fold, or at least 10 fold.

Pharmaceutical Compositions

The present disclosure also includes pharmaceutical compositions that contain therapeutically effective amounts of the IL-17-binding proteins disclosed herein. Compositions can be formulated for use in a variety of drug delivery systems. One or more physiologically acceptable excipients or carriers can also be included in the composition for proper formulation. Suitable formulations for use in the present disclosure are found in Remington's Pharmaceutical Sciences, Mack Publishing Company, Philadelphia, Pa., 17th ed., 1985. For a brief review of methods for drug delivery, see, e.g., Langer (Science 249:1527-1533, 1990).

In some embodiments, a pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. In such embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants (see, *Remington's Pharmaceutical Sciences,* 18th ed. (Mack Publishing Company, 1990)).

In some embodiments, a pharmaceutical composition is citrate-free.

In some embodiments, a pharmaceutical composition may contain nanoparticles, e.g., polymeric nanoparticles, liposomes, or micelles.

In some embodiments, a pharmaceutical composition may contain a sustained- or controlled-delivery formulation. Techniques for formulating sustained- or controlled-delivery means, such as liposome carriers, bio-erodible microparticles or porous beads and depot injections, are also known to those skilled in the art. Sustained-release preparations may include, e.g., porous polymeric microparticles or semi-permeable polymer matrices in the form of shaped articles, e.g., films, or microcapsules. Sustained release matrices may include polyesters, hydrogels, polylactides, copolymers of L-glutamic acid and gamma ethyl-L-glutamate, poly (2-hydroxyethyl-methacrylate), ethylene vinyl acetate, or poly-D (−)-3-hydroxybutyric acid. Sustained release compositions may also include liposomes that can be prepared by any of several methods known in the art.

Pharmaceutical compositions containing a binding protein disclosed herein can be presented in a dosage unit form and can be prepared by any suitable method. A pharmaceutical composition should be formulated to be compatible with its intended route of administration, as discussed further herein in the "Methods of Treatment" section.

Useful formulations can be prepared by methods known in the pharmaceutical art. For example, see *Remington's Pharmaceutical Sciences,* 18th ed. (Mack Publishing Company, 1990). Formulation components suitable for parenteral administration include a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as EDTA; buffers such as acetates, citrates or phosphates; and agents for the adjustment of tonicity such as sodium chloride or dextrose. In some embodiments, the formulation for parenteral administration is citrate-free.

For intravenous or subcutaneous administration, suitable carriers include physiological saline, bacteriostatic water, Cremophor ELTM (BASF, Parsippany, NJ) or phosphate buffered saline (PBS). The carrier should be stable under the conditions of manufacture and storage, and should be preserved against microorganisms. The carrier can be a solvent or dispersion medium containing, for example, water, ethanol, polyol (for example, glycerol, propylene glycol, and liquid polyethylene glycol), and suitable mixtures thereof.

An intravenous or subcutaneous drug delivery formulation may be contained in a syringe, pen, or bag. In some embodiments, the bag is connected to a channel comprising a tube and/or a needle. In some embodiments, the formulation is a lyophilized formulation or a liquid formulation.

These compositions may be sterilized by conventional sterilization techniques, or may be sterile filtered. The resulting aqueous solutions may be packaged for use as-is, or lyophilized, the lyophilized preparation being combined with a sterile aqueous carrier prior to administration.

A polyol, which acts as a tonicifier and may stabilize the binding protein, may also be included in the formulation. The polyol is added to the formulation in an amount which may vary with respect to the desired isotonicity of the formulation. In some embodiments, the aqueous formulation is isotonic. The amount of polyol added may also be altered with respect to the molecular weight of the polyol. For example, a lower amount of a monosaccharide (e.g., mannitol) is added, compared to a disaccharide (such as trehalose). In some embodiments, the polyol which is used in the formulation as a tonicity agent is mannitol.

A detergent or surfactant may also be added to the formulation. Exemplary detergents include nonionic detergents such as polysorbates (e.g., polysorbates 20, 80 etc.) or poloxamers (e.g., poloxamer 188). The amount of detergent added is such that it reduces aggregation of the formulated antibody and/or minimizes the formation of particulates in the formulation and/or reduces adsorption. In some embodiments, the formulation may include a surfactant which is a polysorbate. In some embodiments, the formulation may contain the detergent polysorbate 80 or Tween 80. Tween 80 is a term used to describe polyoxyethylene (80) sorbitanmonooleate (see Fiedler, Lexikon der Hifsstoffe, Editio Cantor Verlag Aulendorf, 4th edi., 1996).

In embodiments, the protein product of the present disclosure is formulated as a liquid formulation. In some embodiments, the liquid formulation is prepared in combination with a sugar at stabilizing levels. In some embodiments, the liquid formulation is prepared in an aqueous carrier. In some embodiments, a stabilizer is added in an amount no greater than that which may result in a viscosity undesirable or unsuitable for intravenous administration. In some embodiments, the sugar is disaccharides, e.g., sucrose. In some embodiments, the liquid formulation may also include one or more of a buffering agent, a surfactant, and a preservative.

In some embodiments, the pH of the liquid formulation is set by addition of a pharmaceutically acceptable acid and/or base. In some embodiments, the pharmaceutically acceptable acid is hydrochloric acid. In some embodiments, the base is sodium hydroxide.

The aqueous carrier of interest herein is one which is pharmaceutically acceptable (safe and non-toxic for administration to a human) and is useful for the preparation of a liquid formulation. Illustrative carriers include sterile water for injection (SWFI), bacteriostatic water for injection (BWFI), a pH buffered solution (e.g., phosphate-buffered saline), sterile saline solution, Ringer's solution or dextrose solution.

A preservative may be optionally added to the formulations herein to reduce bacterial action. The addition of a preservative may, for example, facilitate the production of a multi-use (multiple-dose) formulation.

The binding protein may be lyophilized to produce a lyophilized formulation including the proteins and a lyoprotectant. The lyoprotectant may be sugar, e.g., disaccharides. In some embodiments, the lyoprotectant is sucrose or maltose. The lyophilized formulation may also include one or more of a buffering agent, a surfactant, a bulking agent, and/or a preservative.

The amount of sucrose or maltose useful for stabilization of the lyophilized drug product may be in a weight ratio of at least 1:2 protein to sucrose or maltose. In some embodiments, the protein to sucrose or maltose weight ratio is of from 1:2 to 1:5. In some embodiments, the pH of the formulation, prior to lyophilization, is set by addition of a pharmaceutically acceptable acid and/or base. In some embodiments, the pharmaceutically acceptable acid is hydrochloric acid. In some embodiments, the pharmaceutically acceptable base is sodium hydroxide.

Methods of Treatment

Described herein, in certain embodiments, are methods of treating a subject in need thereof, the method comprising a step of administering to the subject an effective amount of an IL-17-binding protein or a pharmaceutical composition as disclosed herein.

Also described herein, in certain embodiments, are methods of treating, e.g., psoriasis, psoriatic arthritis, or hidradenitis suppurativa in a subject in need thereof, the method comprising a step of administering to the subject a maintenance dose of an IL-17 (e.g., IL-17A, IL-17F, and IL-17A and IL-17F) binding protein (such as an IL-17 binding protein as described herein) at regular intervals for a period of time sufficient to treat or ameliorate psoriasis, psoriatic arthritis, or hidradenitis suppurativa.

Regular Intervals

By "regular interval," it is meant that the intervals between maintenance doses are at least substantially the same but need not be exactly the same, e.g., the durations between intervals may be within 10%, within 9%, within 8%, within 7%, within 6%, within 5%, within 4%, within 3%, within 2%, or within 1% of each other.

In some embodiments, the regular interval between maintenance doses is greater than eight weeks, greater than nine weeks, greater than ten weeks, greater the 11 weeks, greater than 12 weeks, greater than 13 weeks, greater than 14 weeks, or greater than 15 weeks. For example, in some embodiments, the regular interval is about 12 weeks, about 16 weeks, or about 26 weeks. In some embodiments of methods of treating psoriasis or psoriatic arthritis, the regular interval is about 16 weeks or about 26 weeks.

In some embodiments, the regular interval is greater than three months, greater than four months, or greater than five months. For example, in some embodiments, the regular interval is about four months or about six months. In some embodiments of methods of treating psoriasis or psoriatic arthritis, the regular interval is about four months or about six months.

In some embodiments, the regular interval between maintenance doses is greater than two weeks, greater than three weeks, greater than four weeks, greater than five weeks, greater than six weeks, or greater than seven weeks. For example, in some embodiments, the regular interval is about four weeks, about six weeks, or about eight weeks. In some embodiments of methods of treating hidradenitis suppurativa, the regular interval is about four weeks, about six weeks, or about eight weeks.

In some embodiments, the regular interval is about three times a year, four times a year, five times a year, or six times a year.

In some embodiments, the regular interval is greater than half a month, greater than one month, or greater than one and a half months. For example, in some embodiments, the regular interval is about one month, about one and a half months, or about two months. In some embodiments of methods of treating hidradenitis suppurativa, the regular interval is about one month, about one and a half months, or about two months In some embodiments, the regular interval is about 14 weeks to about 28 weeks, about 14 weeks to about 26 weeks, about 14 weeks to about 24 weeks, about 14 weeks to about 22 weeks, about 14 weeks to about 20 weeks, about 14 weeks to about 18 weeks, or about 14 weeks to about 16 weeks.

In some embodiments, the regular interval is about 16 weeks to about 28 weeks, about 16 weeks to about 26 weeks, about 16 weeks to about 24 weeks, about 16 weeks to about 22 weeks, about 16 weeks to about 20 weeks, or about 16 weeks to about 18 weeks.

In some embodiments, the regular interval is about 18 weeks to about 28 weeks, about 18 weeks to about 26 weeks, about 18 weeks to about 24 weeks, about 18 weeks to about 22 weeks, or about 18 weeks to about 20 weeks.

In some embodiments, the regular interval is about 20 weeks to about 28 weeks, about 20 weeks to about 26 weeks, about 20 weeks to about 24 weeks, or about 20 weeks to about 22 weeks.

In some embodiments, the regular interval is about 22 weeks to about 28 weeks, about 22 weeks to about 26 weeks, or about 22 weeks to about 24 weeks.

In some embodiments, the regular interval is about 24 weeks to about 28 weeks, or about 24 weeks to about 26 weeks.

In some embodiments, the regular interval is about 26 weeks to about 28 weeks.

In some embodiments, the regular interval is about two weeks to about ten weeks, about two weeks to about nine weeks, about two weeks to about eight weeks, about two weeks to about seven weeks, about two weeks to about six weeks, about two weeks to about five weeks, about two weeks to about four weeks, or about two weeks to about three weeks.

In some embodiments, the regular interval is about three weeks to about ten weeks, about three weeks to about nine weeks, about three weeks to about eight weeks, about three weeks to about seven weeks, about three weeks to about six weeks, about three weeks to about five weeks, or about three weeks to about four weeks.

In some embodiments, the regular interval is about four weeks to about ten weeks, about four weeks to about nine weeks, about four weeks to about eight weeks, about four weeks to about seven weeks, about four weeks to about six weeks, or about four weeks to about five weeks.

In some embodiments, the regular interval is about five weeks to about ten weeks, about five weeks to about nine weeks, about five weeks to about eight weeks, about five weeks to about seven weeks, or about five weeks to about six weeks.

In some embodiments, the regular interval is about six weeks to about ten weeks, about six weeks to about nine weeks, about six weeks to about eight weeks, or about six weeks to about seven weeks.

In some embodiments, the regular interval is about seven weeks to about ten weeks, about seven weeks to about nine weeks, or about seven weeks to about eight weeks.

In some embodiments, the regular interval is about eight weeks to about ten weeks or about eight weeks to about nine weeks.

In some embodiments, the regular interval is about eight weeks to about nine weeks.

In some embodiments, the regular interval is about three months to about seven months, about three months to about six and a half months, about three months to about six months, about three months to about five and a half months, about three months to about five months, about three months to about four and a half months, about three months to about four months, or about three months to about three and a half months.

In some embodiments, the regular interval is about three and a half months to about seven months, about three and a half months to about six and a half months, about three and a half months to about six months, about three and a half months to about five and a half months, about three and a half months to about five months, about three and a half months to about four and a half months, or about three and a half months to about four months.

In some embodiments, the regular interval is about four months to about seven months, about four months to about six and a half months, about four months to about six months, about four months to about five and a half months, about four months to about five months, or about four months to about four and a half months.

In some embodiments, the regular interval is about four and a half months to about seven months, about four and a half months to about six and a half months, about four and a half months to about six months, about four and a half months to about five and a half months, or about four and a half months to about five months.

In some embodiments, the regular interval is about five months to about seven months, about five months to about six and a half months, about five months to about six months, or about five months to about five and a half months.

In some embodiments, the regular interval is about five and a half months to about seven months, about five and a half months to about six and a half months, or about five and a half months to about six months.

In some embodiments, the regular interval is about six months to about seven months, or about six months to about six and a half months.

In some embodiments, the regular interval is about six and a half months to about seven months.

In some embodiments, the regular interval is about half a month to about two and a half months, about half a month to about two months, about half a month to about one and a half months, or about half a month to about one month.

In some embodiments, the regular interval is about a month to about two and a half months, about a month to about two months, or about a month to about one and a half months.

In some embodiments, the regular interval is about one and a half months to about two and a half months, or about one and a half months to about two months.

In some embodiments, the regular interval is about two months to about two and a half months.

Dose Amounts

In some embodiments, each maintenance dose of the IL-17 binding protein is greater than 300 mg, greater than 320 mg, greater than 340 mg, greater than 360 mg, greater than 380 mg, greater than 400 mg, greater than 420 mg, greater than 440 mg, greater than 460 mg, greater than 480 mg, greater than 500 mg, greater than 520 mg, greater than 420 mg, greater than 440 mg, greater than 460 mg, greater than 480 mg, greater than 500 mg, greater than 520 mg, or greater than 540 mg. For example, in some embodiments, the maintenance dose is about 320 mg, about 350 mg, about 440 mg, or about 510 mg. In some embodiments of methods of treating psoriasis or psoriatic arthritis, the maintenance dose is about 320 mg or about 440 mg. In some embodiments of methods of treating hidradenitis suppurativa, the maintenance dose is about 320 mg, about 350 mg, or about 510 mg.

In some embodiments, each maintenance dose of the IL-17 binding protein is about 300 mg to about 560 mg, about 300 mg to about 540 mg, about 300 mg to about 520 mg, about 300 mg to about 500 mg, about 300 mg to about 480 mg, about 300 mg to about 460 mg, about 300 mg to about 440 mg, about 300 mg to about 420 mg, about 300 mg to about 400 mg, about 300 mg to about 380 mg, about 300 mg to about 360 mg, about 300 mg to about 340 mg, or about 300 mg to about 320 mg.

In some embodiments, each maintenance dose of the IL-17 binding protein is about 320 mg to about 560 mg, about 320 mg to about 540 mg, about 320 mg to about 520 mg, about 320 mg to about 500 mg, about 320 mg to about 480 mg, about 320 mg to about 460 mg, about 320 mg to about 440 mg, about 320 mg to about 420 mg, about 320 mg to about 400 mg, about 320 mg to about 380 mg, about 320 mg to about 360 mg, or about 320 mg to about 340 mg.

In some embodiments, each maintenance dose of the IL-17 binding protein is about 340 mg to about 560 mg, about 340 mg to about 540 mg, about 340 mg to about 520 mg, about 340 mg to about 500 mg, about 340 mg to about 480 mg, about 340 mg to about 460 mg, about 340 mg to about 440 mg, about 340 mg to about 420 mg, about 340 mg to about 400 mg, about 340 mg to about 380 mg, or about 340 mg to about 360 mg.

In some embodiments, each maintenance dose of the IL-17 binding protein is about 360 mg to about 560 mg, about 360 mg to about 540 mg, about 360 mg to about 520 mg, about 360 mg to about 500 mg, about 360 mg to about 480 mg, about 360 mg to about 460 mg, about 360 mg to about 440 mg, about 360 mg to about 420 mg, about 360 mg to about 400 mg, or about 360 mg to about 380 mg.

In some embodiments, each maintenance dose of the IL-17 binding protein is about 380 mg to about 560 mg, about 380 mg to about 540 mg, about 380 mg to about 520 mg, about 380 mg to about 500 mg, about 380 mg to about 480 mg, about 380 mg to about 460 mg, about 380 mg to about 440 mg, about 380 mg to about 420 mg, or about 380 mg to about 400 mg.

In some embodiments, each maintenance dose of the IL-17 binding protein is about 400 mg to about 560 mg, about 400 mg to about 540 mg, about 400 mg to about 520 mg, about 400 mg to about 500 mg, about 400 mg to about 480 mg, about 400 mg to about 460 mg, about 400 mg to about 440 mg, or about 400 mg to about 420 mg.

In some embodiments, each maintenance dose of the IL-17 binding protein is about 420 mg to about 560 mg, about 420 mg to about 540 mg, about 420 mg to about 520 mg, about 420 mg to about 500 mg, about 420 mg to about 480 mg, about 420 mg to about 460 mg, or about 420 mg to about 440 mg.

In some embodiments, each maintenance dose of the IL-17 binding protein is about 440 mg to about 560 mg, about 440 mg to about 540 mg, about 440 mg to about 520 mg, about 440 mg to about 500 mg, about 440 mg to about 480 mg, or about 440 mg to about 460 mg.

In some embodiments, each maintenance dose of the IL-17 binding protein is about 460 mg to about 560 mg, about 460 mg to about 540 mg, about 460 mg to about 520 mg, about 460 mg to about 500 mg, or about 460 mg to about 480 mg.

In some embodiments, each maintenance dose of the IL-17 binding protein is about 480 mg to about 560 mg, about 480 mg to about 540 mg, about 480 mg to about 520 mg, or about 480 mg to about 500 mg.

In some embodiments, each maintenance dose of the IL-17 binding protein is about 500 mg to about 560 mg, about 500 mg to about 540 mg, or about 500 mg to about 520 mg.

In some embodiments, each maintenance dose of the IL-17 binding protein is about 520 mg to about 560 mg, or about 520 mg to about 540 mg.

In some embodiments, each maintenance dose of the IL-17 binding protein is about 540 mg to about 560 mg.

Actual dosage levels of the active ingredients in the pharmaceutical compositions of this disclosure may be in whatever amount as to obtain an amount of the active ingredient which is effective to achieve the desired therapeutic response for a particular patient, composition, and mode of administration, without being toxic to the patient.

The specific dose can be a uniform dose in the amounts mentioned herein. Alternatively, a patient's dose can be tailored to the approximate body weight or surface area of the patient. Other factors in determining the appropriate dosage can include the disease or condition to be treated or prevented, the severity of the disease, the route of administration, and the age, sex, and medical condition of the patient. Further refinement of the calculations necessary to determine the appropriate dosage for treatment is routinely made by those skilled in the art, especially in light of the dosage information and assays disclosed herein. The dosage can also be determined through the use of known assays for determining dosages used in conjunction with appropriate dose-response data. An individual patient's dosage can be adjusted as the progress of the disease is monitored. Blood levels of the targetable construct or complex in a patient can be measured to see if the dosage needs to be adjusted to reach or maintain an effective concentration. Pharmacogenomics may be used to determine which targetable constructs and/or complexes, and dosages thereof, are most likely to be effective for a given individual (Schmitz et al., *Clinica Chimica Acta* 308: 43-53, 2001; Steimer et al., *Clinica Chimica Acta* 308: 33-41, 2001).

Induction Doses

In certain embodiments, prior to the administering a first maintenance dose, the subject has received an induction dose of the IL-17 binding protein. The induction dose can be administered at once (e.g., in one day) or split into multiple (e.g., two) doses administered in parts a time period apart. In some embodiments, the amount of the induction dose is the same as the amount of each maintenance dose and is administered at once. In some embodiments, the amount of the induction dose is a multiple of the amount of the maintenance dose and is administered in parts, each part of the induction dose having the same amount the IL-17 binding protein as the amount in each maintenance dose. In embodiments in which the induction dose is administered in parts, the interval between each part may be, e.g., at least one week, at least two weeks, at least three weeks, at least four weeks, at least five weeks, at least six weeks, at least seven weeks, at least eight weeks, at least nine weeks, at least ten weeks, or at least 12 weeks. In some embodiments, the induction dose is administered in parts, with an interval of about twelve weeks between each part.

Subjects

In certain embodiments, the subject to whom the IL-17 binding proteins are administered in accordance with the present disclosure is a mammal, such as a primate. In some embodiments, the subject is human.

Generally, the subject is suffering from, exhibits at least one symptom of, is diagnosed with, or is identified as at risk of psoriasis, psoriatic arthritis, axial spondyloarthritis, palmoplantar pustulosis, non-infectious uveitis, polymyalgia rheumatica, giant cell arteritis, juvenile idiopathic arthritis, dissecting cellulitis of the scalp, Behcet's disease, Netherton syndrome, *Pityriasis rubra pilaris*, SAPHO syndrome, or hidradenitis suppurativa.

Psoriasis is a skin disease that causes a rash with itchy, scaly patches, most commonly on the knees, elbows, trunk and scalp. Plaque psoriasis, the most common type of psoriasis, causes dry, itchy, raised skin patches (plaques) covered with scales. Plaques usually appear on the elbows, knees, lower back and scalp.

Psoriatic arthritis (PsA) refers to chronic inflammatory arthritis associated with psoriasis. About 1 in 20 individuals with psoriasis will develop arthritis along with psoriasis, and in about 75% of cases, psoriasis precedes the arthritis. PsA exhibits itself in a variety of ways, ranging from mild to severe arthritis, wherein the arthritis usually affects the fingers and the spine.

Hidradenitis suppurativa is a painful, chronic skin condition which causes skin abscesses and scarring on the skin. Pea- to marble-sized lumps form under the skin. These lumps can be painful and usually occur where skin rubs together, such as in the armpits, groin, and buttocks.

Routes of Administration

In certain embodiments, the step of administering comprises systemic administration. In certain embodiments, systemic administration comprises parenteral administration, e.g., intravenous administration, intraarterial administration, intraperitoneal administration, subcutaneous administration, or intradermal administration. In some embodiments, systemic administration comprises enteric administration, e.g., trans-gastroenteric administration or oral administration.

In some embodiments, the step of administering comprises intravenous administration. In some embodiments, the step of administering comprises subcutaneous administration.

Outcomes

In many embodiments, methods disclosed herein result in a measurable improvement in the subject, e.g., in amelioration or resolution of symptoms. For example, such improvement may include an improvement in a clinical score or a score from a survey or questionnaire associated with, or suitable for assessing, psoriasis, psoriatic arthritis, or hidradenitis suppurativa.

For example, in some embodiments, a reduction in the psoriasis area and severity index (PASI), e.g., a 50% reduction or a 75% reduction in the PASI score, PASI 50 and PASI 75, respectively, is achieved.

Alternatively or additionally, an improvement of the score(s) or quality of life, as determined by any or any combination of the following instruments, may be achieved by the presently disclosed methods: Dermatology Life Quality Index (DLQI), Investigator Global Assessment (IGA), Nail Psoriasis Severity Index (NAPSI), Physician Global Assessment (PGA), or Medical Outcomes Study Short Form (36) Health Survey (SF-36), or Treatment Satisfaction Questionnaire for Medication (TSQM).

In some embodiments, an improvement in the clinical score or quality of life as measured by any or any combination of the following instruments is achieved: Composite Psoriatic Disease Activity Index (CPDAI), PsA Disease Activity Score (PASDAS), Group for Research and Assessment of Psoriasis and Psoriatic Arthritis (GRAPPA) Composite Exercise (GRACE) index, Psoriatic Arthritis Impact of Disease (PsAID) questionnaire, or Work Productivity and Activity Impairment (WPAI) questionnaire.

Alternatively or additionally, an improvement of the score(s) or quality of life, as determined by any or any combination of the following instruments, may be achieved by the presently disclosed methods: International Hidradenitis Suppurativa Severity Score System (HIS4), Hurley, Hurley Staging refined, Sartorius score (e.g., 2003, 2007, and/or 2009 versions), Hidradenitis Suppurativa Physician Global Assessment (HS-PGA), Severity Assessment of Hidradenitis Suppurativa (SAHS), Hidradenitis Suppurativa Severity Index (HSSI), Acne Inversa Severity Index (AISI), the Static Metascore, Hidradenitis Suppurativa Clinical Response (HiSCR), iHS4-55, and the Dynamic Metascore.

EXAMPLES

Example 1: Affinity Maturation of Anti-IL-17A/F Antibody

An anti-human IL-17A/F antibody whose sequences are shown in Table 3 below ("IL-17A/F Reference Antibody") was used as a parental antibody for further CDR diversification to identify clones with improvements in potency, manufacturability, and pharmacokinetics.

TABLE 3

IL-17A/F Reference Antibody sequences
CDR sequences shown are according to Kabat.

| Heavy chain variable domain | Light chain variable domain |
|---|---|
| $V_H$: EVQLVESGGGLVQPGGSL RLSCAASGFTFSDYNMAW VRQAPGKGLEWVATITYE GRNTYYRDSVKGRFTISR DNAKNSLYLQMNSLRAED TAVYYCASPPQYYEGSIY RLWFAHWGQG TLVTVSS (SEQ ID NO: 80) | $V_L$: AIQLTQSPSSLSASVGDRVTIT CRADESVRTLMHWYQQKPGKAP KLLIYLVSNSEIGVPDRFSGSG SGTDFRLTISSLQPEDFATYYC QQTWSDPWTFGQGTKVEIK (SEQ ID NO: 83) |

TABLE 3-continued

IL-17A/F Reference Antibody sequences
CDR sequences shown are according to Kabat.

| Heavy chain variable domain | Light chain variable domain |
|---|---|
| CDR-H1: DYNMA (SEQ ID NO: 69) | CDR-L1: RADESVRTLMH (SEQ ID NO: 4) |
| CDR-H2: TITYEGRNTYYRDSVKG (SEQ ID NO: 70) | CDR-L2: LVSNSEI (SEQ ID NO: 5) |
| CDR-H3: PPQYYEGSIYRLWFAH (SEQ ID NO: 71) | CDR-L3: QQTWSDPWT (SEQ ID NO: 72) |

Individual libraries were prepared for heavy chain CDR1/2, heavy chain CDR3, light chain CDR1/2, and light chain CDR3. Individual mutants were displayed as single-chain variable fragments (scFvs) in a yeast display system. Within each library, mutants were panned through multiple rounds of selection using various concentrations of biotinylated IL-17A and IL-17F (alternating) until significant enrichment of binders crossreactive to both IL-17A and IL-17F was achieved.

The resulting output from each of the individual libraries was sequenced and then used to build a combinatorial library encompassing mutations at each CDR within a yeast display system. Within this library, mutants were again panned through multiple rounds of selection using various concentrations of biotinylated IL-17A and IL-17F (alternating) until significant enrichment of binders crossreactive to both IL-17A and IL-17F was achieved.

Finally, the output of this library was then sequenced and reformatted to full antibody format. Briefly, the coding sequences for the heavy chain and light chain of the antibody were generated by DNA synthesis and PCR, then subsequently subcloned into plasmids for protein expression in a mammalian cell system. The gene sequences in the expression vectors were confirmed by DNA sequencing. Antibodies were then purified by a two-step affinity chromatography (Protein A) and size-exclusion chromatography process.

Example 2: Framework Modifications of Anti-IL-17A/F Antibody

Modifications to the framework regions of the IL-17A/F Reference Antibody described in Example 1 were identified to improve antibody developability and expression. A molecular model of the V regions of the IL-17A/F Reference Antibody was constructed and framework modifications of interest in VH and/or VL were identified by comparing to validated human germlines. The resulting humanized VL and VH were then combined and reformatted to full antibody format. Briefly, the coding sequences for the heavy chain and light chain of the antibody were generated by DNA synthesis and PCR, then subsequently subcloned into plasmids for protein expression in a mammalian cell system. The gene sequences in the expression vectors were confirmed by DNA sequencing. Antibodies were then purified by a two-step affinity chromatography (Protein A) and size-exclusion chromatography process. Ten antibody clones were selected for further analysis.

Example 3: Determination of Antibody Affinity to IL-17A/F

Binding affinity (KD) of antibodies to human IL-17A or IL-17F (generated as described in Example 1 or 2) was determined through surface plasmon resonance (SPR) using a BIACORE™ 8K SPR system (Cytiva). Series S Sensor CM5 (Cytiva) chips were prepared by immobilizing goat anti-human IgG (Jackson ImmunoResearch) and used to determine the binding kinetic rate and affinity constants at 25° C. in a running buffer of HBS-P+ (10 mM HEPES pH 7.4, 300 mM NaCl, 3 mM EDTA, 0.05% v/v Surfactant P20). Anti-IL-17A/F antibodies (diluted to 1 g/mL) were captured onto flow cell 2 (active) for 60 sec at a flow rate of 10 μL/min. Recombinant Human IL-17A or IL-17F was prepared at concentrations of 0, 0.62, 1.85, 5.56, 16.67, and 50.0 nM and injected over flow cell 1 (reference) and flow cell 2 (active) for 180 sec at a flow rate of 50 L/min. Samples were injected in a multi-cycle manner over freshly captured mAb, by regenerating the capture surfaces with injection of 10 mM glycine, pH 1.5 for 30 sec at a flow rate of 30 L/min. A 1:1 kinetic binding model was utilized to determine the apparent association (ka) and dissociation rate constants (kd). Their ratio provides the apparent equilibrium dissociation constant or affinity constant (KD=kd/ka). Results for binding to human IL-17A and human IL-17F are set forth in Table 4 and Table 5, respectively.

TABLE 4

| Antibody | hIL-17A ka (1/Ms) | hIL-17A kd (1/s) | hIL-17A KD (M) |
|---|---|---|---|
| IL-17A/F Reference Antibody | 1.67E+06 | 7.78E−05 | 4.65E−11 |
| Clone 1011A | 1.68E+06 | 8.25E−06 | 4.91E−12 |
| Clone 1011D | 1.50E+06 | 4.01E−05 | 2.68E−11 |
| Clone 1114D | 7.59E+05 | 1.69E−05 | 2.22E−11 |
| Clone 1161A | 1.67E+06 | 7.06E−06 | 4.23E−12 |
| Clone 1161D | 1.75E+06 | 6.33E−06 | 3.61E−12 |
| Clone 1181D | 1.32E+06 | 2.14E−05 | 1.62E−11 |
| Clone 1182A | 1.19E+06 | 3.05E−06 | 2.56E−12 |
| Clone 1182D | 1.25E+06 | 3.67E−05 | 2.93E−11 |
| Clone 2001D | 1.78E+06 | 2.55E−06 | 1.44E−12 |
| Clone 2002D | 1.68E+06 | 6.71E−06 | 4.00E−12 |

TABLE 5

| Antibody | hIL-17F ka (1/Ms) | hIL-17F kd (1/s) | hIL-17F KD (M) |
|---|---|---|---|
| IL-17A/F Reference Antibody | 2.97E+05 | 1.76E−04 | 5.91E−10 |
| Clone 1011A | 2.89E+05 | 6.05E−05 | 2.09E−10 |
| Clone 1011D | 1.86E+05 | 1.30E−04 | 7.00E−10 |
| Clone 1114D | 1.86E+05 | 1.18E−04 | 6.33E−10 |
| Clone 1161A | 3.92E+05 | 2.09E−05 | 5.32E−11 |
| Clone 1161D | 3.89E+05 | 5.97E−06 | 1.53E−11 |
| Clone 1181D | 3.04E+05 | 4.04E−04 | 1.33E−09 |
| Clone 1182A | 3.12E+05 | 4.55E−05 | 1.46E−10 |
| Clone 1182D | 2.63E+05 | 5.02E−05 | 1.91E−10 |
| Clone 2001D | 4.02E+05 | 1.72E−04 | 4.28E−10 |
| Clone 2002D | 2.79E+05 | 2.77E−04 | 9.94E−10 |

Example 4: Inhibition of IL-17A/F-Induced Activation of NFκB in HEK293 IL-17RA+/IL-17RC+NFκB-Linked Luciferase Reporter Cells Inhibition of NFκB activation in HEK293 cells expressing IL-17RA, IL-17RC, and an NFκB-linked luciferase reporter (Acro Biosciences) was used to evaluate the functional activity of antibodies to block IL-17A/F-induced biological activity. Briefly, reporter cells were seeded at a density of $3\times10^4$ cells/well and cultured overnight. A mixture of purified IL-17A/F antibodies and either human IL-17A or human IL-17F (Acro Biosciences) were allowed to associate for 1 hour at 37° C. before adding to cells, resulting in a final concentration of either 5 ng/mL of human IL-17A or 1 μg/mL of human IL-17F and a range of antibody concentrations from 0-200 nM. Cells were incubated at 37° C. for 16 hours and subsequently lysed with One-Glo luciferase assay buffer (Promega) at room temperature for 10 min under dark conditions. Luminescence was quantified by a Varioskan microplate reader (Thermo Scientific) and subsequent data were analyzed using GraphPad Prism. $IC_{50}$ values were determined as the concentration of antibody required to inhibit 50% of the maximum luminescent signal detected with incubation of either 5 ng/mL of human IL-17A alone or 1 μg/mL of human IL-17F alone.

Figure 1B:
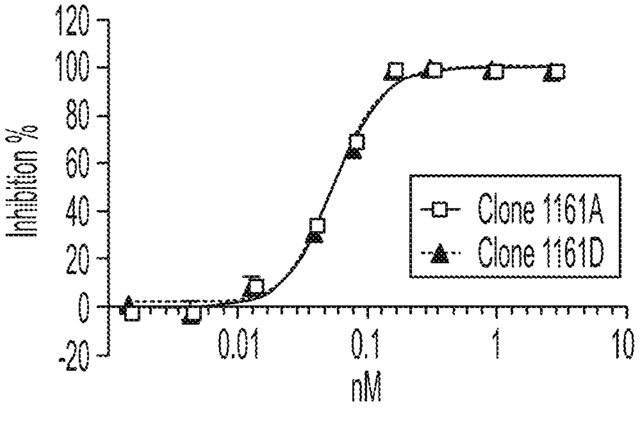
Figure 1C:
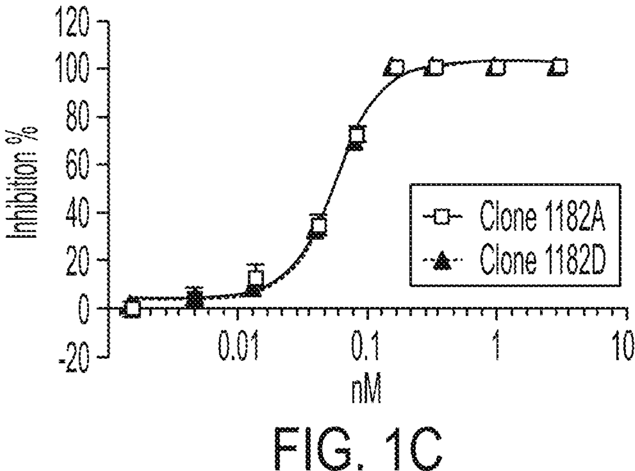
Figure 1D:
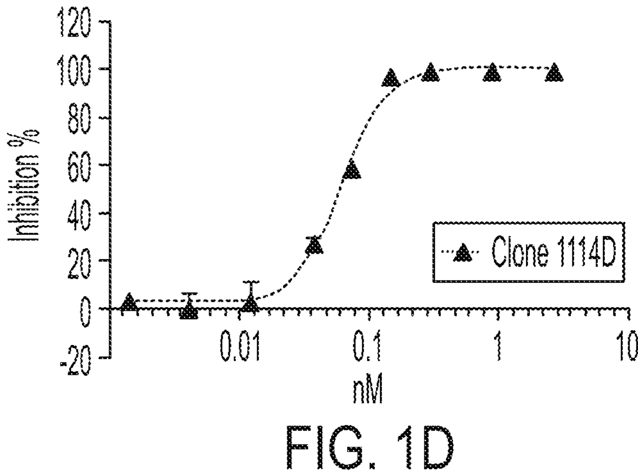
Figure 1E:
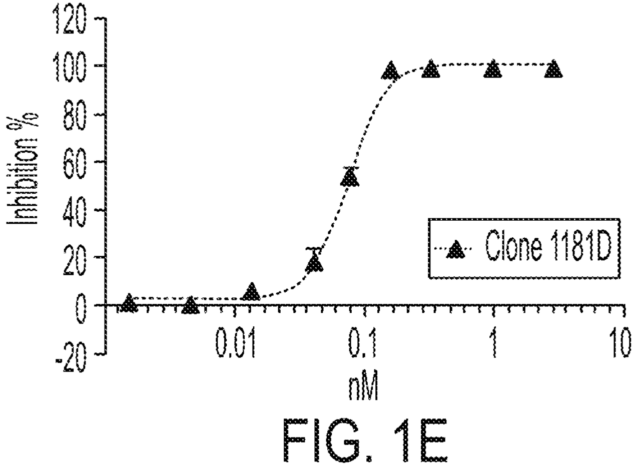
Figure 1F:
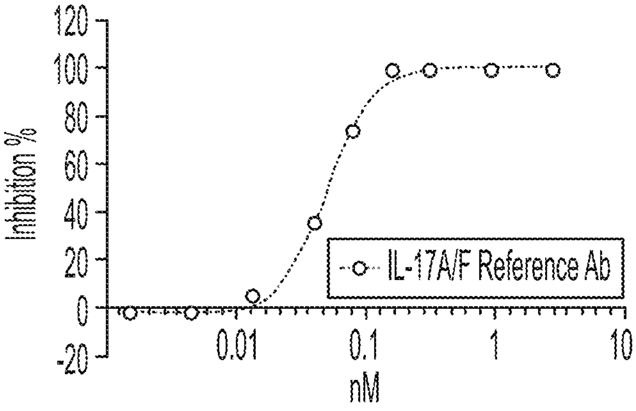

FIG. 1A (Clone 1011A and Clone 1011D), FIG. 1B (Clone 1161A and Clone 1116D), FIG. 1C (Clone 1182A and Clone 1182D), FIG. 1D (Clone 1114D), FIG. 1E (Clone 1181D), and FIG. 1F (IL-17 A/F Reference Ab) show percent inhibition of IL-17A induced activation of NFκB in a reporter cell line.

Figure 2A:
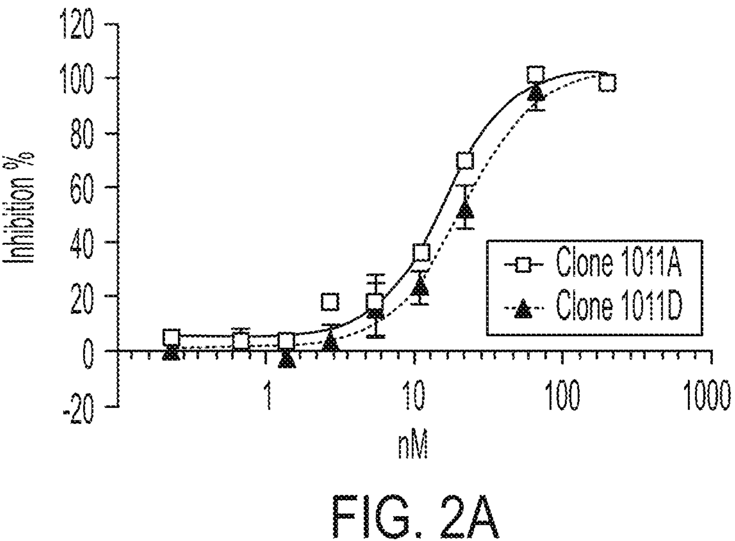
FIGS. 2A-2H are graphs showing percent inhibition of IL-17F induced activation of NFκB in a reporter cell line. Specifically, FIG. 2A (Clone 1011A and Clone 1011D), FIG. 2B (Clone 1161A and Clone 1116D), FIG. 2C (Clone 1182A and Clone 1182D), FIG. 2D (Clone 2002D), FIG. 2E (Clone 1114D), FIG. 2F (Clone 1181D), FIG. 2G (Clone 2001D), and FIG. 2H (IL-17 A/F Reference Ab) show percent inhibition of IL-17F induced activation of NFκB.
Figure 2B:
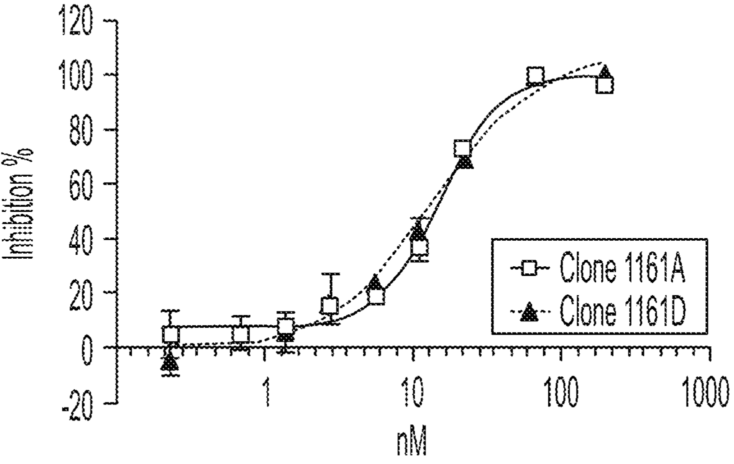
Figure 2C:
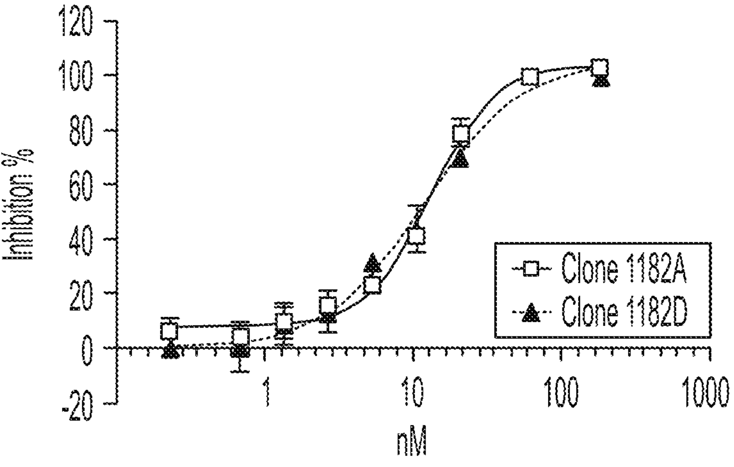
Figure 2D:
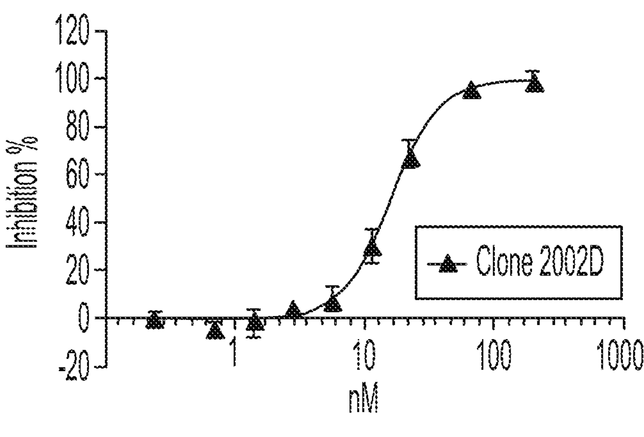
Figure 2E:
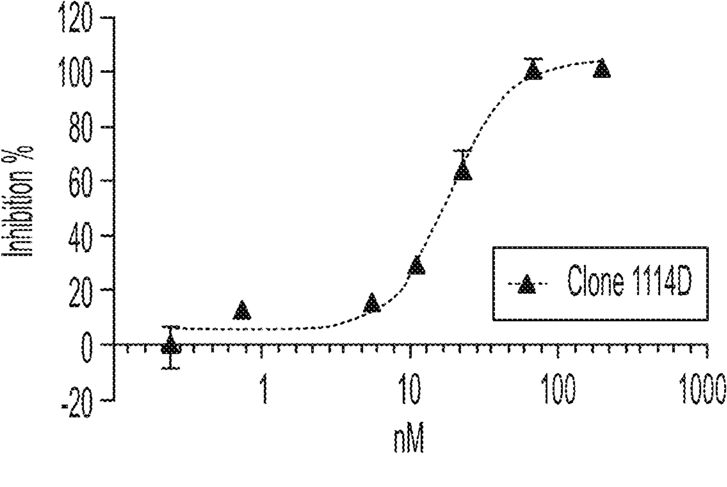
Figure 2F:
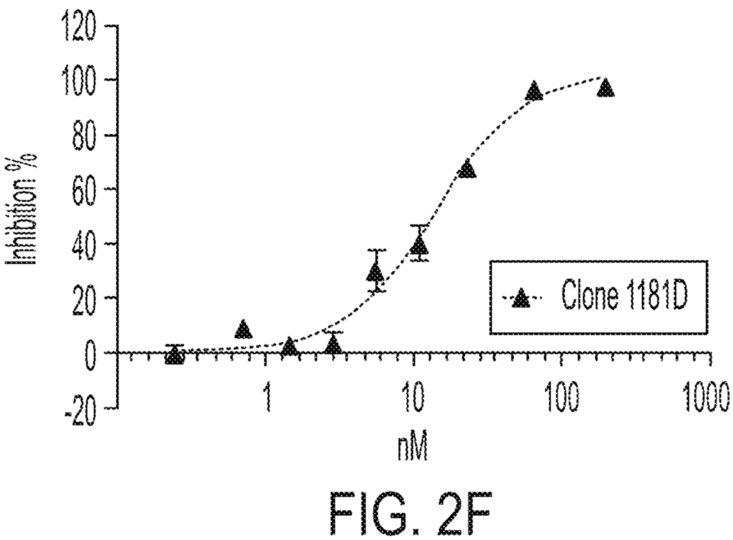
Figure 2G:
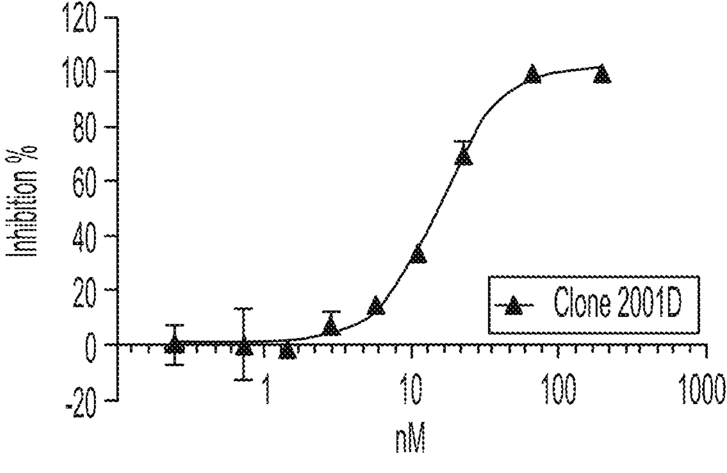
Figure 2H:
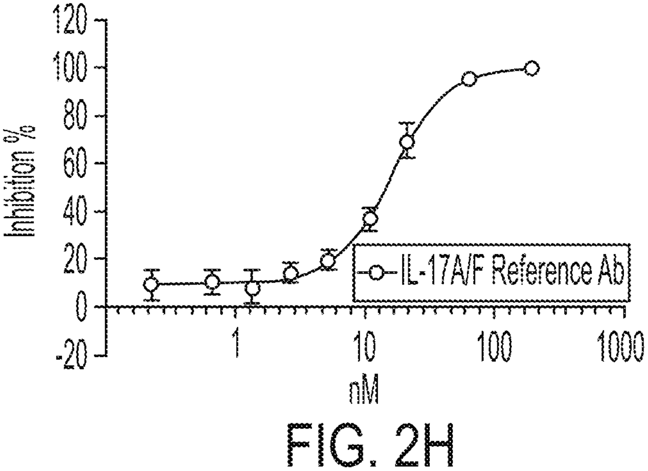

FIG. 2A (Clone 1011A and Clone 1011D), FIG. 2B (Clone 1161A and Clone 1116D), FIG. 2C (Clone 1182A and Clone 1182D), FIG. 2D (Clone 2002D), FIG. 2E (Clone 1114D), FIG. 2F (Clone 1181D), FIG. 2G (Clone 2001D), and FIG. 2H (IL-17 A/F Reference Ab) show percent inhibition of IL-17F induced activation of NFκB in a reporter cell line.

As shown in FIGS. 1A-1F (IL-17A) and FIGS. 2A-2H (IL-17F), the affinity matured clones generally have similar potency as the IL-17A/F Reference Antibody in multiple in vitro assays conducted. Specifically, the clones generally demonstrated comparable inhibition of IL-17A and IL-17F-induced activation of NFκB in the experiment tested as compared to the IL-17A/F Reference Antibody. Moreover, as shown in Table 6 (relative $IC_{50}$) and Table 7 (absolute $IC_{50}$), the affinity matured clones generally demonstrated comparable inhibition of IL-17A/F-induced activation of NFκB in the experiment tested as compared to the IL-17A/F Reference Antibody.

TABLE 6

NFκB Activation in Reporter Cell Line (Relative $IC_{50}$)

| Antibody | Relative $IC_{50}$ IL-17A | Relative $IC_{50}$ IL-17F |
|---|---|---|
| IL-17A/F Reference Antibody | 1.00 | 1.00 |
| Clone 1011A | 1.25 | 1.06 |
| Clone 1011D | 1.23 | 1.10 |
| Clone 1114D | 1.18 | 1.06 |
| Clone 1161A | 1.13 | 1.05 |
| Clone 1161D | 1.14 | 0.89 |
| Clone 1181D | 1.41 | 0.87 |
| Clone 1182A | 1.12 | 0.96 |
| Clone 1182D | 1.12 | 0.82 |
| Clone 2001D | N/A | 1.01 |
| Clone 2002D | N/A | 1.04 |

Values relative to IL-17A/F Reference Antibody.
<1.00 is more potent.
N/A not analyzed.

TABLE 7

NFκB Activation in Reporter Cell Line (Absolute $IC_{50}$)

| Antibody | Absolute $IC_{50}$ IL-17A (nM) | Absolute $IC_{50}$ IL-17F (nM) |
|---|---|---|
| IL-17A/F Reference Antibody | 0.049 | 14.1 |
| Clone 1011A | 0.061 | 15.0 |
| Clone 1011D | 0.060 | 15.6 |
| Clone 1114D | 0.058 | 15.0 |
| Clone 1161A | 0.055 | 14.9 |
| Clone 1161D | 0.056 | 12.5 |
| Clone 1181D | 0.069 | 12.3 |
| Clone 1182A | 0.055 | 13.6 |
| Clone 1182D | 0.055 | 11.6 |
| Clone 2001D | 0.049 | 14.3 |
| Clone 2002D | 0.047 | 14.6 |

Example 5: Inhibition of IL-17A/F-Induced Release of IL-6 in Normal Human Dermal Fibroblasts Inhibition of IL-6 release from normal human dermal fibroblast (NHDF) cells was used to evaluate the functional activity of antibodies to block IL-17A/F-induced biological activity. Briefly, NHDF cells were seeded at a density of $6\times10^3$ cells/well and cultured overnight. A mixture of purified IL-17A/F antibodies and either human IL-17A+tumor necrosis factor (TNF) or human IL-17F+TNF were allowed to associate for 1 hour at 37° C. before adding to cells, resulting in a final concentration of either 1 ng/mL of human IL-17A or 30 ng/mL of human IL-17F, 0.5 ng/mL TNF, and a range of antibody concentrations from 0-13.3 nM. Cells were incubated at 37° C. for 16 hr and released IL-6 in the supernatant was measured using human IL-6 DuoSet ELISA (R&D Systems).

Subsequent data were analyzed using GraphPad Prism. $IC_{50}$ values were determined as the concentration of antibody required to inhibit 50% of the maximum IL-6 release detected with incubation of 0.5 ng/mL TNF and either 1 ng/mL of human IL-17A or 30 ng/mL of human IL-17F without IL-17A/F antibodies.

As shown in Table 8 (relative $IC_{50}$) and Table 9 (absolute $IC_{50}$), the affinity matured clones demonstrated somewhat comparable inhibition of IL-17A- (FIG. 1A) and IL-17F- (FIG. 1B) induced release of IL-6 as compared to the IL-17A/F Reference Antibody.

TABLE 8

Inhibition of IL-17A/F-induced release of IL-6 (Relative $IC_{50}$)

| Antibody | Relative $IC_{50}$ IL-17A | Relative $IC_{50}$ IL-17F |
|---|---|---|
| IL-17A/F Reference Antibody | 1.00 | 1.00 |
| Clone 1011A | 0.88 | 0.96 |
| Clone 1011D | 0.89 | 0.75 |
| Clone 1114D | 1.03 | 0.93 |
| Clone 1161A | 1.05 | 0.87 |
| Clone 1161D | 0.97 | 0.99 |
| Clone 1181D | 1.21 | 1.11 |
| Clone 1182A | 1.07 | 1.06 |
| Clone 1182D | 1.04 | 0.93 |
| Clone 2001D | 0.96 | 1.02 |
| Clone 2002D | 1.05 | 1.00 |

Values relative to IL-17A/F Reference Antibody. <1.00 is more potent.

TABLE 9

Inhibition of IL-17A/F-Induced Release of IL-6 (Absolute $IC_{50}$)

| Antibody | Absolute $IC_{50}$ IL-17A (nM) | Absolute $IC_{50}$ IL-17F (nM) |
|---|---|---|
| IL-17A/F Reference Antibody | 0.014 | 0.727 |
| Clone 1011A | 0.013 | 0.700 |
| Clone 1011D | 0.013 | 0.545 |
| Clone 1114D | 0.015 | 0.678 |
| Clone 1161A | 0.015 | 0.630 |
| Clone 1161D | 0.014 | 0.719 |
| Clone 1181D | 0.017 | 0.808 |
| Clone 1182A | 0.015 | 0.772 |
| Clone 1182D | 0.015 | 0.675 |
| Clone 2001D | 0.014 | 0.740 |
| Clone 2002D | 0.015 | 0.729 |

Example 6: Half-Lives of IL-17A/F Antibodies

Half-life extension of one or more IL-17A/F antibodies generated as described in Examples 1 and/or 2 and engineered to have IgG1 Fc polypeptides with M252Y/S254T/T256E (YTE) mutations (the "test IL-17A/F antibody") was measured via pharmacokinetic (PK) analysis in cynomolgus monkeys (non-human primates (NHPs)) dosed with a single bolus of 50 mg/kg of the test IL-17A/F antibody and the serum levels of the antibody were analyzed on Day 49 (N=4 for each group).

Figure 3A:
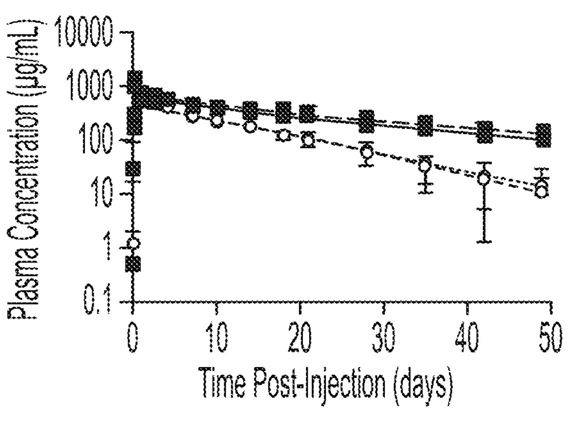
FIGS. 3A-3J are graphs showing the half-life of the clones. Specifically, FIG. 3A (Clone 1011A), FIG. 3B (Clone 1011D), FIG. 3C (Clone 1114D), FIG. 3D (Clone 1161A), FIG. 3E (Clone 1161D), FIG. 3F (Clone 1181D), FIG. 3G (Clone 1182A), FIG. 3H (Clone 1182D), FIG. 3I (Clone 2001D), and FIG. 3J (Clone 2002D) show the half-life of the clones compared to the IL-17A/F Reference Antibody.
Figure 3B:
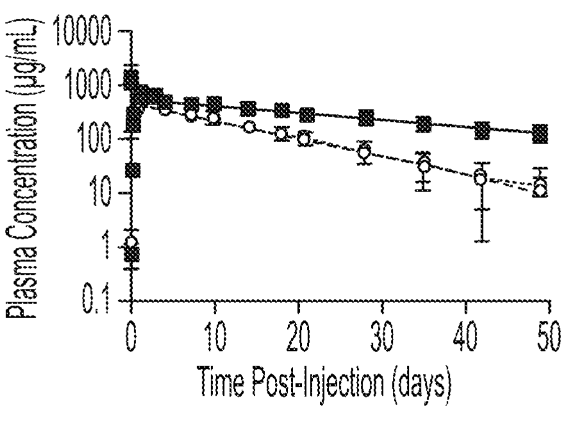
Figure 3C:
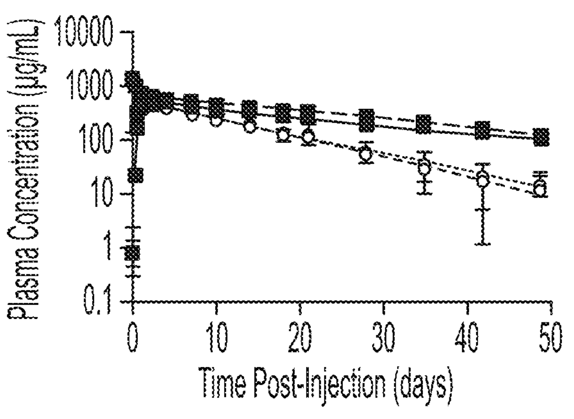
Figure 3D:
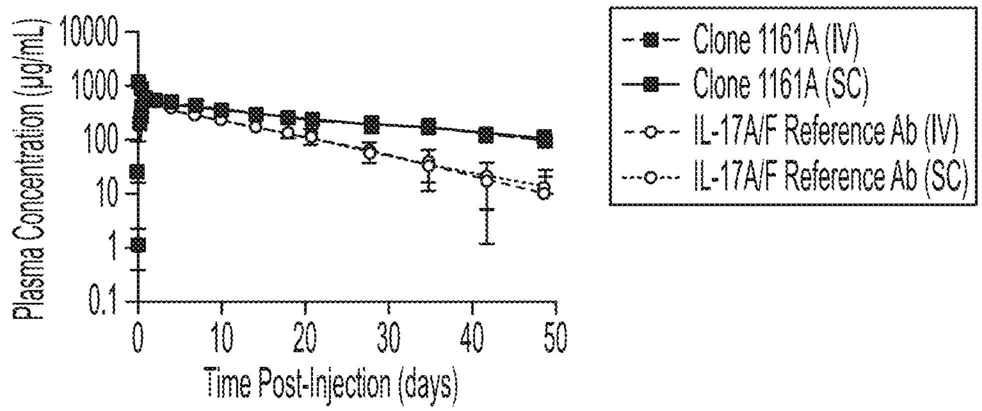
Figure 3E:
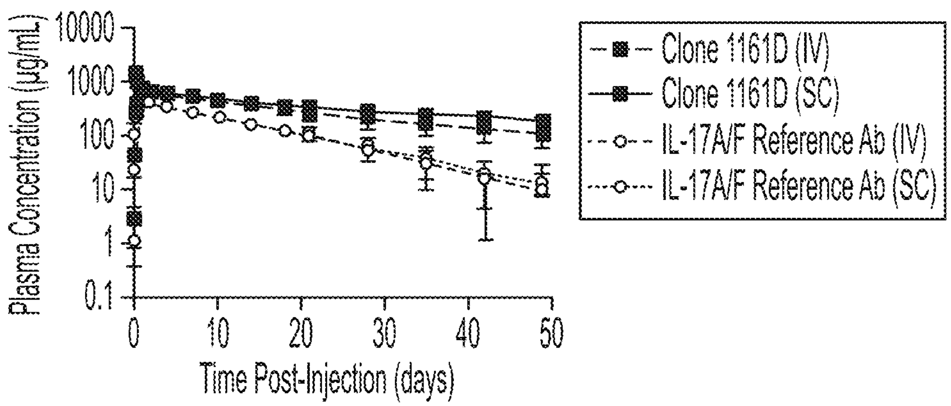
Figure 3F:
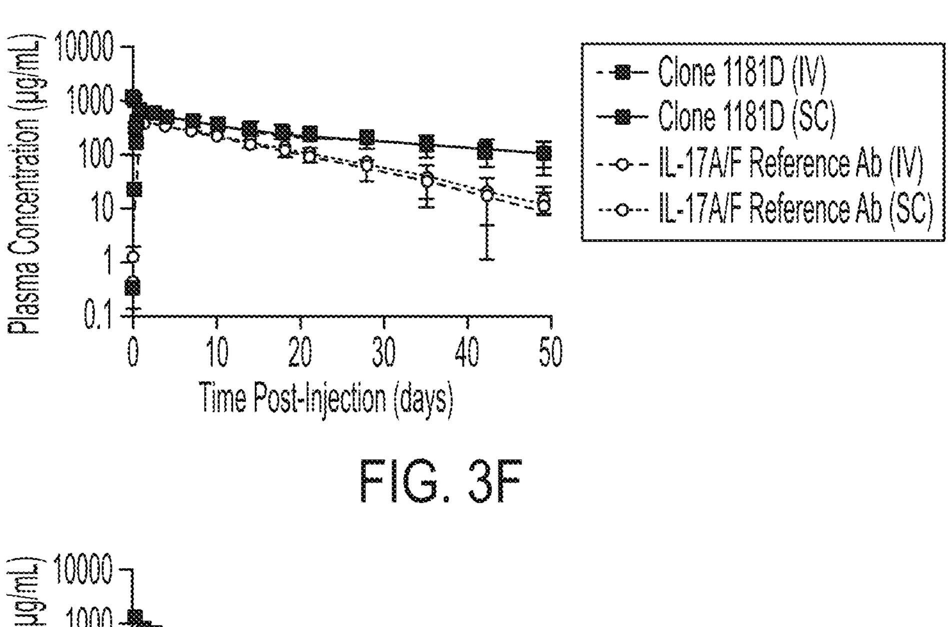
Figure 3G:
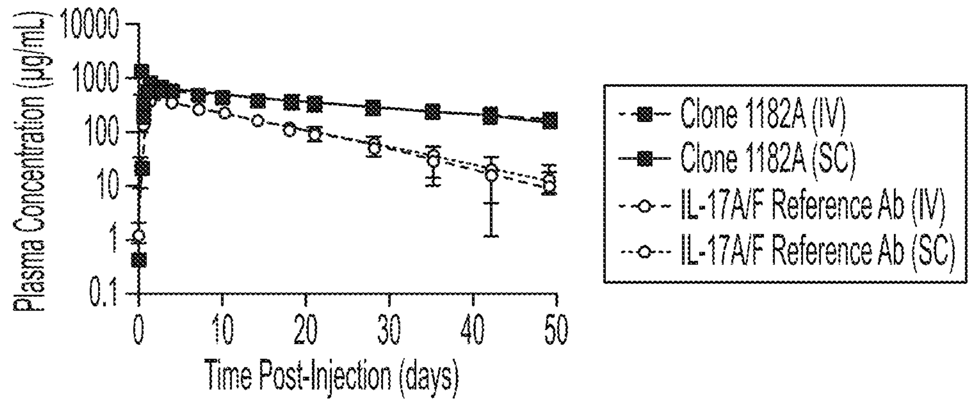
Figure 3H:
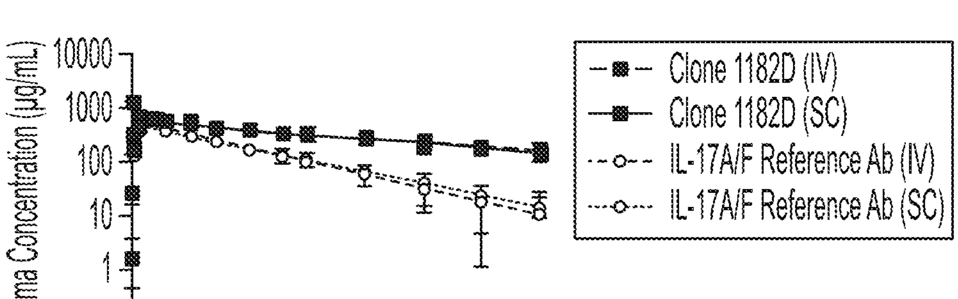
Figure 3I:
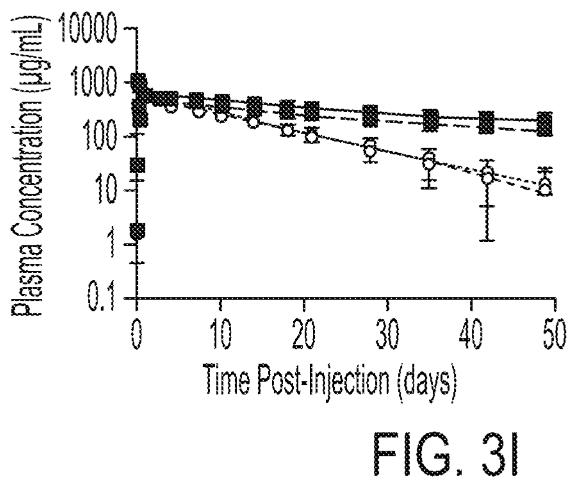
Figure 3I:
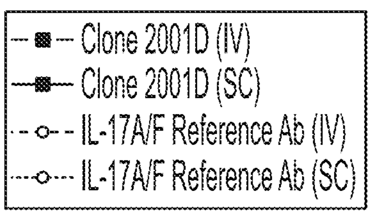
Figure 3J:
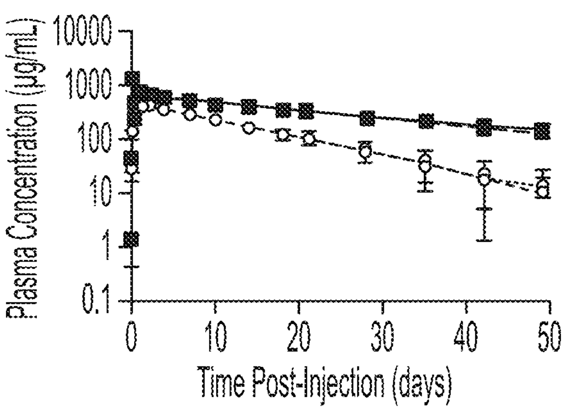
Figure 3J:
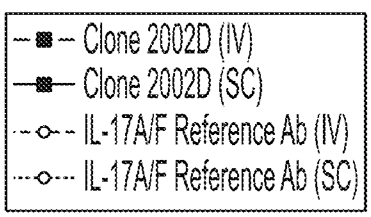

FIG. 3A (Clone 1011A), FIG. 3B (Clone 1011D), FIG. 3C (Clone 1114D), FIG. 3D (Clone 1161A), FIG. 3E (Clone 1161D), FIG. 3F (Clone 1181D), FIG. 3G (Clone 1182A), FIG. 3H (Clone 1182D), FIG. 3I (Clone 2001D), and FIG. 3J (Clone 2002D) show the half-life of the clones compared to the IL-17A/F Reference Antibody for both intravenous and subcutaneous administration. As shown in FIGS. 3A-3J and Table 10, the half-life of all of the clones was significantly extended in cynomolgus monkeys compared to the IL-17A/F Reference Antibody for both intravenous and subcutaneous administration. In particular, Clone 1182A demonstrated a half-life of over 30 days in cynomolgus monkeys, which exceeds that of the IL-17A/F Reference Antibody by over 3-fold, when the antibody is administered either intravenously or subcutaneously.

TABLE 10

Half-Life of Clones Versus IL-17A/F Reference Antibody

| Antibody | Half-Life (D) Following Intravenous Administration | Half-Life (D) Following Subcutaneous Administration |
|---|---|---|
| IL-17A/F Reference Antibody | 9.2 | 9.8 |
| Clone 1011A | 20.4 | 18.9 |
| Clone 1011D | 21.5 | 27.4 |
| Clone 1114D | 24.5 | 25.9 |
| Clone 1161A | 17.0 | 20.0 |
| Clone 1161D | 24.0 | 31.6 |
| Clone 1181D | 19.4 | 28.1 |
| Clone 1182A | 31.2 | 31.6 |
| Clone 1182D | 29.7 | 20.8 |
| Clone 2001D | 24.9 | 32.8 |
| Clone 2002D | 22.7 | 24.5 |

Based on allometric scaling of the clearance of the test IL-17A/F antibody observed in this study, predictive simulations of the test IL-17A/F antibody's pharmacokinetics in humans suggest that subcutaneous maintenance dosing every four to six months could be achieved while maintaining high antibody exposures.

Figure 4A:
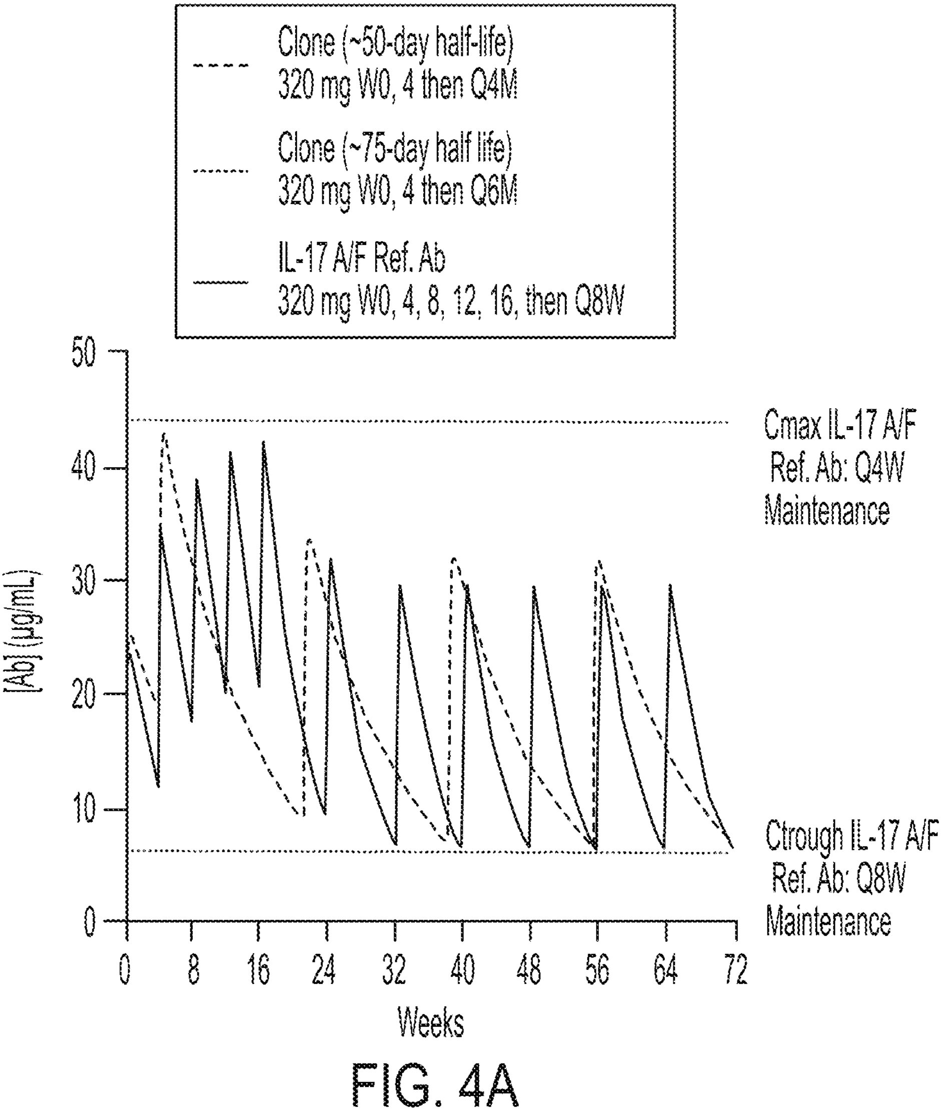
FIG. 4A (~50-day half-life) and FIG. 4B (~75-day half-life) are graphs depicting predictive simulations of the clone pharmacokinetics (PK) in humans versus the IL-17A/F Reference Antibody.
Figure 4B:
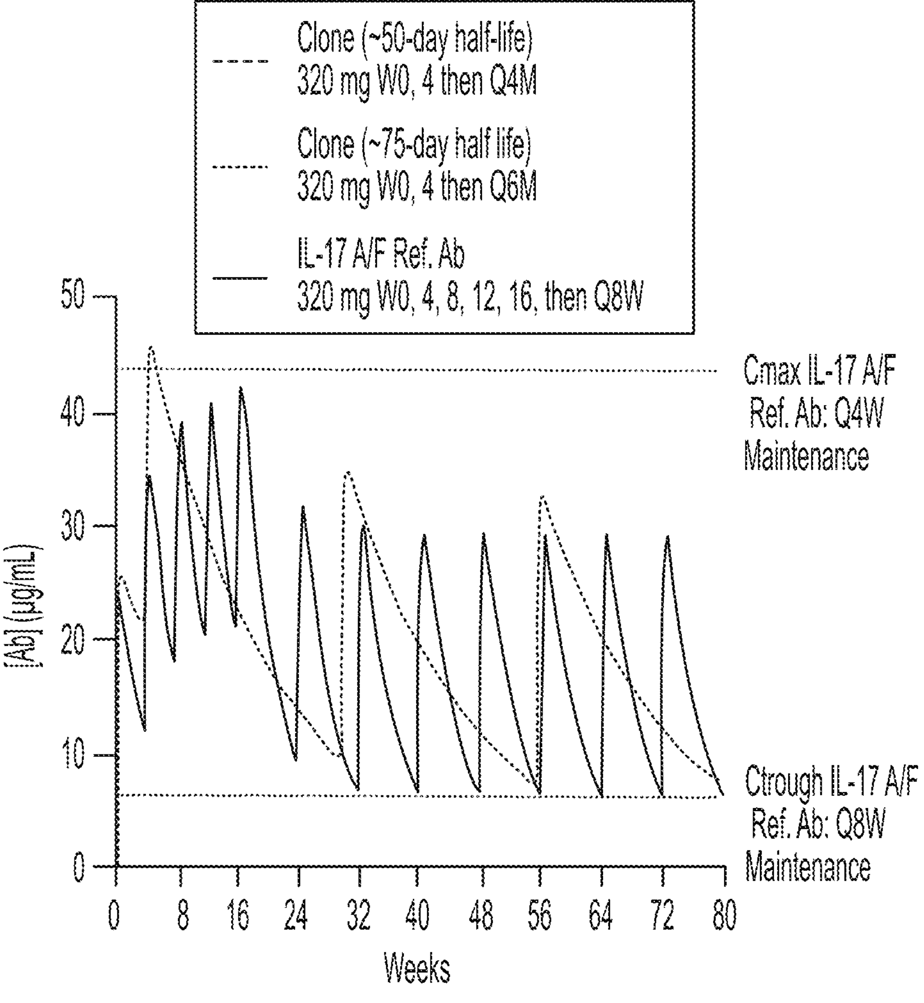

FIGS. 4A-4B are graphs depicting predictive simulations of the clone pharmacokinetics (PK) in humans versus the IL-17A/F Reference Antibody. Predictive simulations of the clone pharmacokinetics (PK) in humans suggest that a half-life of ~50 days (FIG. 4A) would enable subcutaneous maintenance dosing every 4 months (three times per year) and a half-life of ~75 days (FIG. 4B) would enable dosing every 6 months (twice a year) while maintaining trough antibody concentrations above the IL-17A/F Reference Antibody (SC).

Discussion Regarding Examples 1-6

The test IL-17A/F antibodies generated as described in Examples 1 and/or 2 exhibit high selectivity and affinity for IL-17A and IL-17F in vitro, potent inhibition of downstream cellular signaling ex vivo, and an extended half-life in non-human primates compared to the reference IL-17A/F antibody, providing potential for dosing every four months (three times a year) to six months (twice a year) with comparable or increased efficacy. In total, these data provide preclinical evidence of the test IL-17A/F antibody's clinical potential to improve upon currently available therapies for psoriatic disease and other inflammatory conditions. Clinical studies may further demonstrate this potential.

Example 7: Manufacturing of IL-17A/F Antibodies

Small-scale antibody production was carried out using CHO cells for each IL-17A/F antibody to assess the manufacturability of each antibody clone. The solubility, viscosity and stability of each IL-17A/F antibody was analyzed. As shown in Table 11, except for clone 1161D, all clones demonstrated comparable solubility, and exceeding the solubility of the Reference Antibody.

TABLE 11

Solubility of IL-17A/F Antibodies

| Antibody | Solubility (mg/mL) |
|---|---|
| Reference Antibody | 203.4 |
| 1182D | 263.2 |
| 1182A | 260.1 |
| 1011A | 254.5 |
| 1114D | 252.0 |
| 1011D | 244.8 |
| 2001D | 240.9 |
| 2002D | 239.6 |
| 1181D | 236.7 |
| 1161A | 215.9 |
| 1161D | 189.1 |

Figure 5:
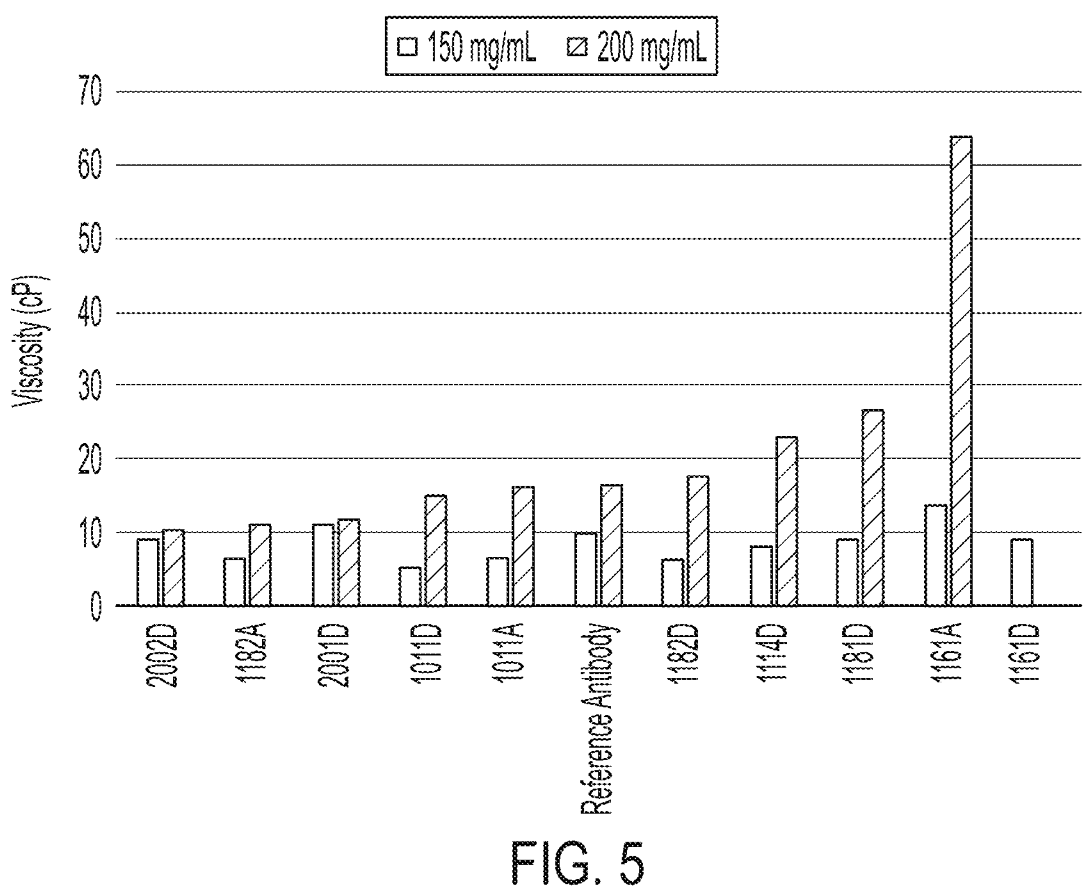
FIG. 5 shows a bar graph depicting viscosity (cP) of each IL-17A/F antibody preparation at two different concentrations.

Viscosity of each IL-17A/F antibody was assessed at the concentration of either 150 mg/mL or 200 mg/mL in a formulation with a pH of pH 6. Viscosity is a factor affecting drug product formulation, manufacturing, and delivery. As shown in FIG. 5, except for clone 1161A at the higher concentration of 200 mg/mL, all clones exhibited acceptable viscosity at either concentration. Among all the clones tested, clone 1011D shows the lowest viscosity at the lower concentration of 150 mg/mL, and clone 2002D shows the lowest viscosity at the higher concentration 200 mg/mL, while clones 1182A, 2001D, and 2002D all show favorable low viscosity at both concentrations.

We next assessed the stability of each antibody clone under stress conditions. In an experiment examining thermal stability, the antibody samples were incubated at 40° C. for 2 or 4 weeks and thereafter were subjected to imaged capillary isoelectric focusing (iCIEF) analysis to quantify the main peak and other charge variants. The data in Table 12 show that while most of the clones showed around 12.7%-26.9% decrease in main peak after the stress test, clone 1182A showed only an 8.8% decrease in main peak after 2 weeks and only a 19.6% decrease in main peak after 4 weeks under stress conditions, the lowest among all clones tested under the same conditions.

TABLE 12

Stability of IL-17A/F Antibodies

| Antibody | iCIEF Main Peak % | | |
|---|---|---|---|
| | T0 | 40° C. for 2 weeks | 40° C. for 4 weeks |
| Reference Antibody | 69.4 | 56.7 (12.7 ↓) | 47.6 (21.8 ↓) |
| 1011D | 67.0 | 49.6 (17.4 ↓) | 40.9 (26.1 ↓) |
| 1114D | 72.1 | 53.6 (18.5 ↓) | 45.2 (26.9 ↓) |
| 1161D | 64.0 | 45.4 (18.6 ↓) | 42.1 (21.9 ↓) |
| 1181D | 66.8 | 49.3 (17.5 ↓) | 43.2 (23.6 ↓) |
| 1182D | 71.6 | 58.4 (13.2 ↓) | 47.0 (24.6 ↓) |
| 1011A | 73.1 | 60.4 (12.7 ↓) | 47.4 (25.7 ↓) |
| 1161A | 63.6 | 47.2 (16.4 ↓) | 40.1 (23.5 ↓) |
| 1182A | 67.6 | 58.8 (8.8 ↓) | 48.0 (19.6 ↓) |
| 2001D | 72.1 | 57.3 (14.8 ↓) | 47.8 (24.3 ↓) |
| 2002D | 64.3 | 50.9 (13.4 ↓) | 42.5 (21.8 ↓) |

OTHER EMBODIMENTS

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features set forth herein.

What is claimed is:

1. An IL-17-binding protein comprising an immunoglobulin heavy chain variable domain ($V_H$) and an immunoglobulin light chain variable domain ($V_L$) comprising complementarity-determining regions:

(a) CDR-H1 comprising the amino acid sequence of SEQ ID NO: 55;
  CDR-H2 comprising the amino acid sequence of SEQ ID NO: 56;
  CDR-H3 comprising the amino acid sequence of SEQ ID NO: 57;
  CDR-L1 comprising the amino acid sequence of SEQ ID NO: 4;
  CDR-L2 comprising the amino acid sequence of SEQ ID NO: 5; and
  CDR-L3 comprising the amino acid sequence of SEQ ID NO: 58;

(b) CDR-H1 comprising the amino acid sequence of SEQ ID NO: 59;
  CDR-H2 comprising the amino acid sequence of SEQ ID NO: 60;
  CDR-H3 comprising the amino acid sequence of SEQ ID NO: 61;
  CDR-L1 comprising the amino acid sequence of SEQ ID NO: 10;
  CDR-L2 comprising the amino acid sequence LVS; and
  CDR-L3 comprising the amino acid sequence of SEQ ID NO: 58; or (c) CDR-H1 comprising the amino acid sequence of SEQ ID NO: 62;
  CDR-H2 comprising the amino acid sequence of SEQ ID NO: 63;
  CDR-H3 comprising the amino acid sequence of SEQ ID NO: 64;
  CDR-L1 comprising the amino acid sequence of SEQ ID NO: 14;
  CDR-L2 comprising the amino acid sequence LVS; and
  CDR-L3 comprising the amino acid sequence of SEQ ID NO: 65.

2. The IL-17-binding protein of claim 1, wherein the $V_H$ comprises an amino acid sequence that is at least 95% identical to the amino acid sequence of SEQ ID NO: 66 and the $V_L$ comprises an amino acid that is at least 95% identical to the amino acid sequence of SEQ ID NO: 67.

3. The IL-17-binding protein of claim 1, wherein the $V_H$ comprises an amino acid sequence that is at least 95% identical to the amino acid sequence of SEQ ID NO: 66 and the $V_L$ comprises an amino acid that is at least 95% identical to the amino acid sequence of SEQ ID NO: 68.

4. The IL-17-binding protein of claim 1, wherein the $V_H$ comprises an amino acid sequence that is at least 98% identical to the amino acid sequence of SEQ ID NO: 66 and the $V_L$ comprises an amino acid that is at least 98% identical to the amino acid sequence of SEQ ID NO: 67.

5. The IL-17-binding protein of claim 1, wherein the $V_H$ comprises an amino acid sequence that is at least 98% identical to the amino acid sequence of SEQ ID NO: 66 and the $V_L$ comprises an amino acid that is at least 98% identical to the amino acid sequence of SEQ ID NO: 68.

6. The IL-17-binding protein of claim 1, wherein the $V_H$ comprises the amino acid sequence of SEQ ID NO: 66 and the $V_L$ comprises the amino acid sequence of SEQ ID NO: 67 or 68.

7. The IL-17-binding protein of claim 1, wherein the IL-17-binding protein comprises an antibody or an antigen-binding fragment thereof.

8. The IL-17-binding protein of claim 7, wherein the antigen-binding fragment is a Fab, a F (ab') 2, a Fab', a single-chain Fv (scFv), a single-chain Fab (scFab), an Fv fragment, or an Fd fragment.

9. The IL-17-binding protein of claim 1, wherein the IL-17-binding protein comprises an Fc region.

10. The IL-17-binding protein of claim 9, wherein the Fc region comprises a half-life extending mutation or a set of half-life extending mutations.

11. The IL-17-binding protein of claim 10, wherein the Fc region comprises M252Y/S254T/T256E mutations and/or M428L/N434L mutations according to the EU numbering system.

12. The IL-17-binding protein of claim 1, comprising a heavy chain comprising an amino acid sequence that is at least 90% identical to the amino acid sequence of SEQ ID NO: 208 and a light chain comprising an amino acid sequence that is at least 90% identical to the amino acid sequence of SEQ ID NO: 209.

13. The IL-17-binding protein of claim 1, comprising a heavy chain comprising an amino acid sequence that is at least 95% identical to the amino acid sequence of SEQ ID NO: 208 and a light chain comprising an amino acid sequence that is at least 95% identical to the amino acid sequence of SEQ ID NO: 209.

14. The IL-17-binding protein of claim 1, comprising a heavy chain comprising an amino acid sequence that is at least 90% identical to the amino acid sequence of SEQ ID NO: 300 and a light chain comprising an amino acid sequence that is at least 90% identical to the amino acid sequence of SEQ ID NO: 301.

15. The IL-17-binding protein of claim 1, comprising a heavy chain comprising an amino acid sequence that is at least 95% identical to the amino acid sequence of SEQ ID NO: 300 and a light chain comprising an amino acid sequence that is at least 95% identical to the amino acid sequence of SEQ ID NO: 301.

16. An isolated nucleic acid encoding the IL-17-binding protein of claim 1.

17. An expression vector comprising the isolated nucleic acid of claim 16.

18. An isolated host cell comprising the isolated nucleic acid of claim 16.

19. A method of making an IL-17-binding protein comprising the step of culturing the host cell of claim 18 under suitable conditions to produce the IL-17-binding protein.

20. A composition comprising the IL-17-binding protein of claim 1 and a pharmaceutically acceptable carrier.

21. A method of producing the IL-17-binding protein of claim 1, comprising the steps of introducing a nucleic acid encoding the IL-17-binding protein into a host cell, and culturing the host cell under suitable conditions to produce the IL-17-binding protein.

* * * * *